(12) United States Patent
Kim et al.

(10) Patent No.: US 10,039,841 B2
(45) Date of Patent: Aug. 7, 2018

(54) GENE THERAPY VECTOR SYSTEM AND PRODRUG GENES

(71) Applicant: The Industry & Academic Cooperation in Chungnam National University (IAC), Daejeon (KR)

(72) Inventors: Yeon Soo Kim, Daejeon (KR); Moonkyung Kang, Daejeon (KR); Min Jeong Baek, Daejeon (KR)

(73) Assignee: THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 33 days.

(21) Appl. No.: 15/365,117

(22) Filed: Nov. 30, 2016

(65) Prior Publication Data

US 2018/0147299 A1     May 31, 2018

Related U.S. Application Data

(63) Continuation of application No. PCT/KR2016/013881, filed on Nov. 29, 2016.

(51) Int. Cl.
| | | |
|---|---|---|
| *A01N 63/00* | (2006.01) | |
| *A61K 48/00* | (2006.01) | |
| *A61K 31/495* | (2006.01) | |
| *A61K 31/513* | (2006.01) | |
| *A61K 38/50* | (2006.01) | |
| *A61K 35/768* | (2015.01) | |
| *C12N 9/78* | (2006.01) | |
| *C12N 9/12* | (2006.01) | |
| *C12N 15/86* | (2006.01) | |
| *C12N 7/00* | (2006.01) | |

(52) U.S. Cl.
CPC ............ *A61K 48/0058* (2013.01); *C12N 7/00* (2013.01); *C12N 9/1211* (2013.01); *C12N 9/78* (2013.01); *C12N 15/86* (2013.01); *C12Y 305/04001* (2013.01); *C12N 2740/10043* (2013.01); *C12N 2740/10052* (2013.01); *C12N 2740/13022* (2013.01); *C12N 2740/13043* (2013.01)

(58) Field of Classification Search
None
See application file for complete search history.

(56) References Cited

U.S. PATENT DOCUMENTS

| | | |
|---|---|---|
| 2013/0130986 A1 | 5/2013 | Gruber et al. |
| 2013/0323301 A1 | 12/2013 | Gruber et al. |
| 2014/0242033 A1 | 8/2014 | Gruber et al. |
| 2015/0273029 A1 | 10/2015 | Gruber et al. |
| 2016/0053232 A1 | 2/2016 | Gruber et al. |

FOREIGN PATENT DOCUMENTS

KR   10-2013-0103954 A   9/2013

OTHER PUBLICATIONS

M. Takahashi, et al; Radiosensitization of gliomas by intracellular generation of 5-fluorouracil potentiates prodrug activator gene therapy with a retroviral replicating vector; Cander Gene Ther.; No. 10; 2014; pp. 405-410.

Synergistic Anticancer Effects of Ganciclovir/Thymidine Kinase and 5-Fluorocytosine/Cytosine Deaminase Gene Therapies, J Natl Cancer Inst. Mar. 4, 1998;90(5):370-80.

*Primary Examiner* — Robert M Kelly
(74) *Attorney, Agent, or Firm* — Lucas & Mercanti, LLP

(57) ABSTRACT

The present invention relates to a replication retrovirus vector system comprising thymidine kinase (HSV-TK) gene and cytosine deaminase (CD) gene which make gene transfer to cancer cell tissue for the efficient treatment of cancer. Particularly, the HSV-TK/CD combined self-replicating retrovirus vector system of the present invention characteristically contains both HSV-TK and CD genes; has no worries about losing a therapeutic gene because recombination does not occur in this system during virus infection; and has an excellent stability, and also is able to induce cancer cell death by using the prodrug GCV or 5-FC and can apply a therapeutic gene or a prodrug thereof selectively to such cancer that shows resistance against cancer treatment using either TK or CD, so that this system of the invention can be advantageously used as a pharmaceutical composition for the treatment of cancer.

15 Claims, 84 Drawing Sheets

[Fig. 1a]
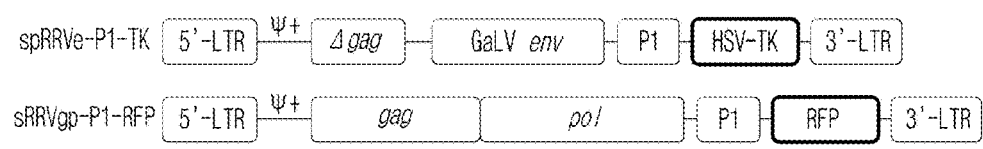
[Fig. 1b]

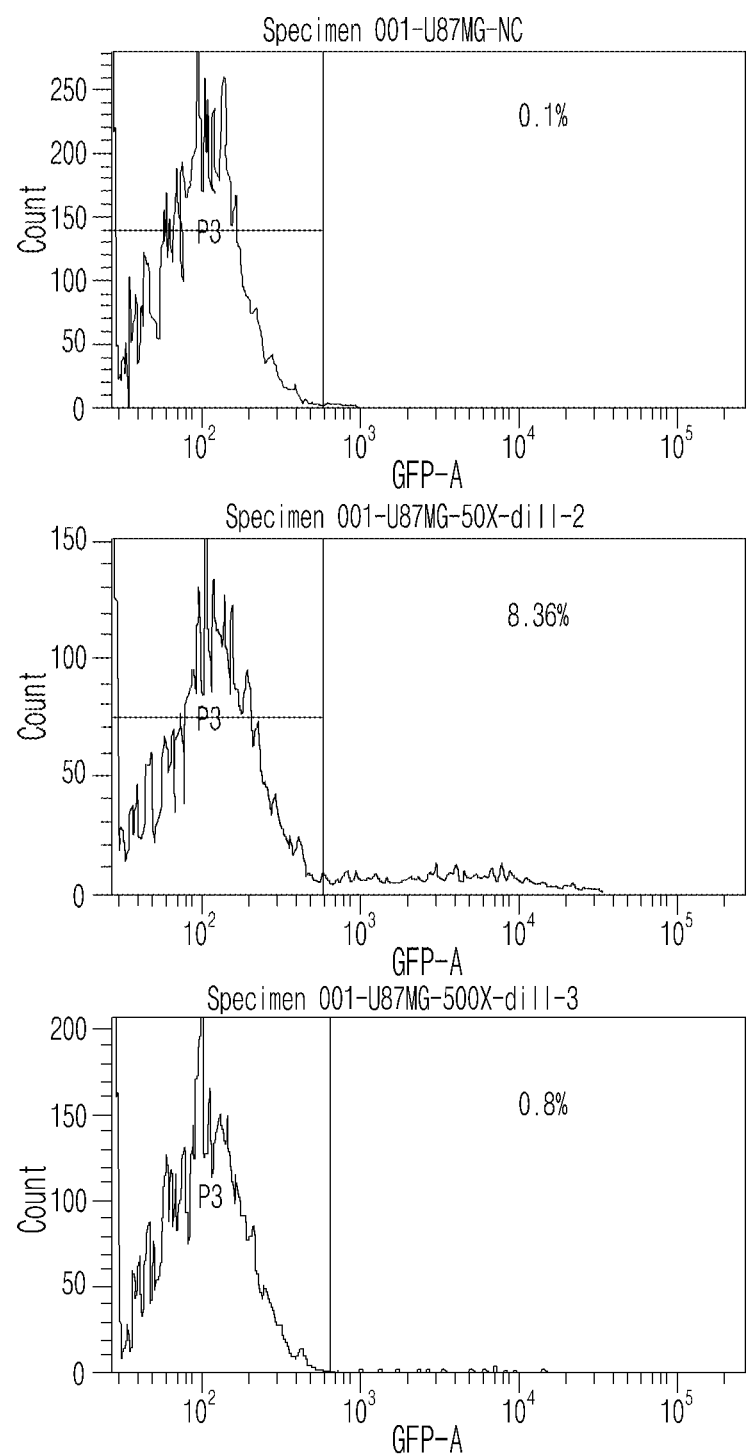
[Fig. 2a]

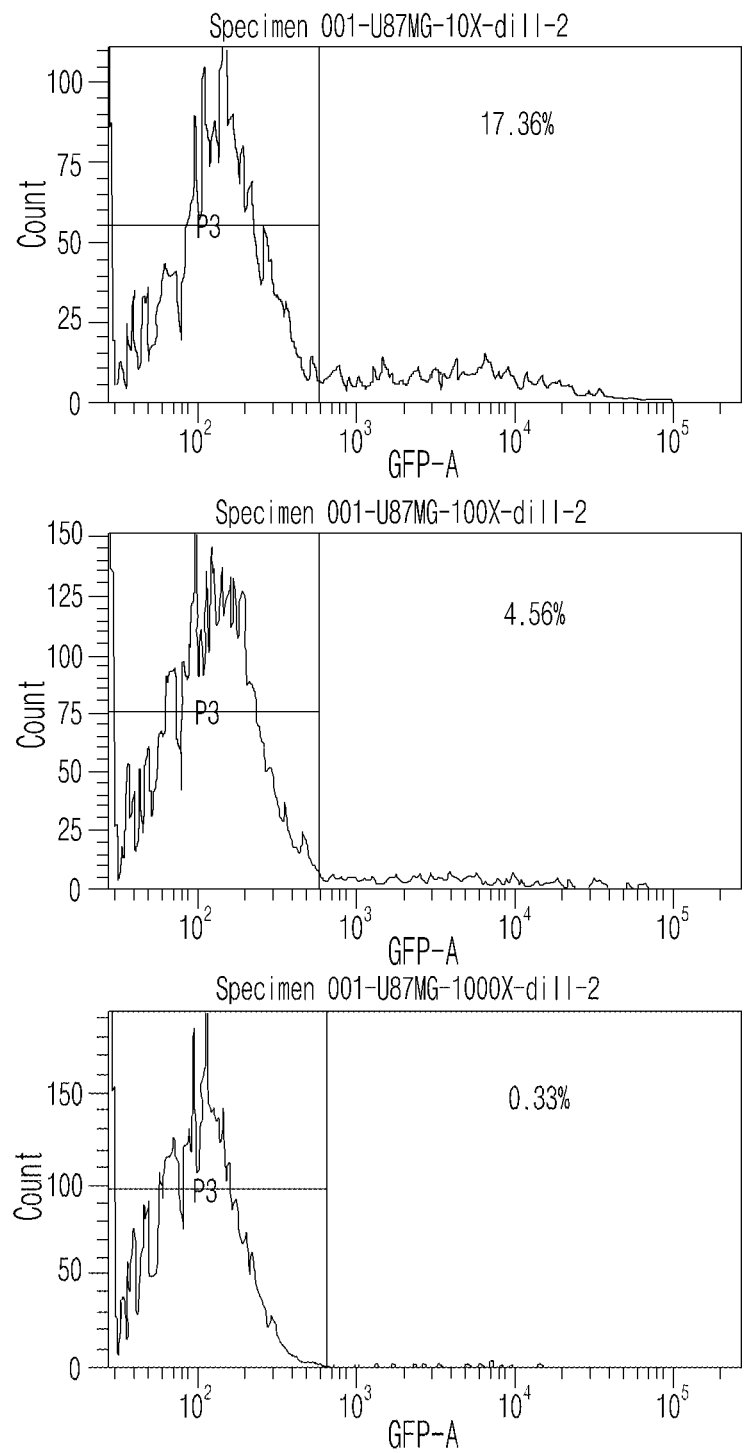
[Fig. 2b]

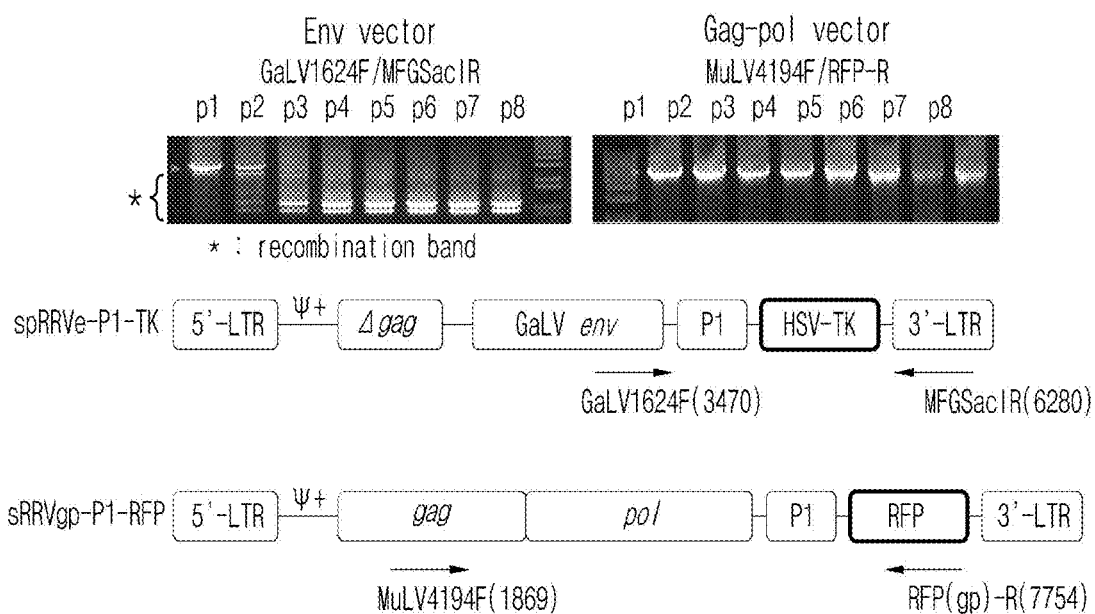

[Fig. 3b]
spRRVe-P1-GFP / sRRVgp-P1-TK
Env vector
GaLV1624F/MFGSacIR
p1 p2 p3 p4 p5 p6 p7 p8
Gag-pol vector
MuLV4194F/MFGSacIR
p1 p2 p3 p4 p5 p6 p7 p8
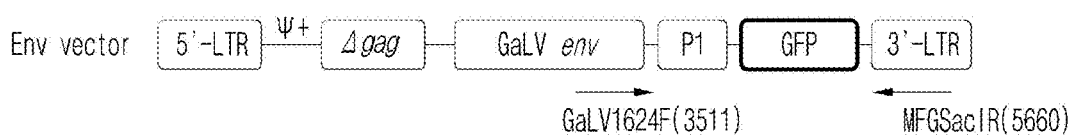
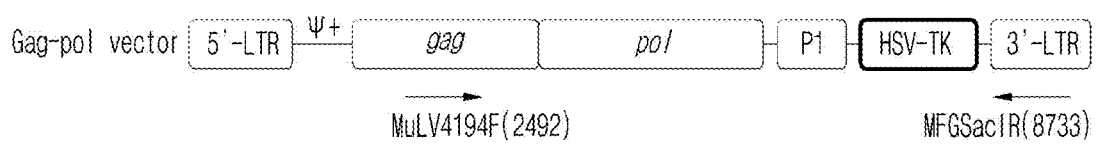

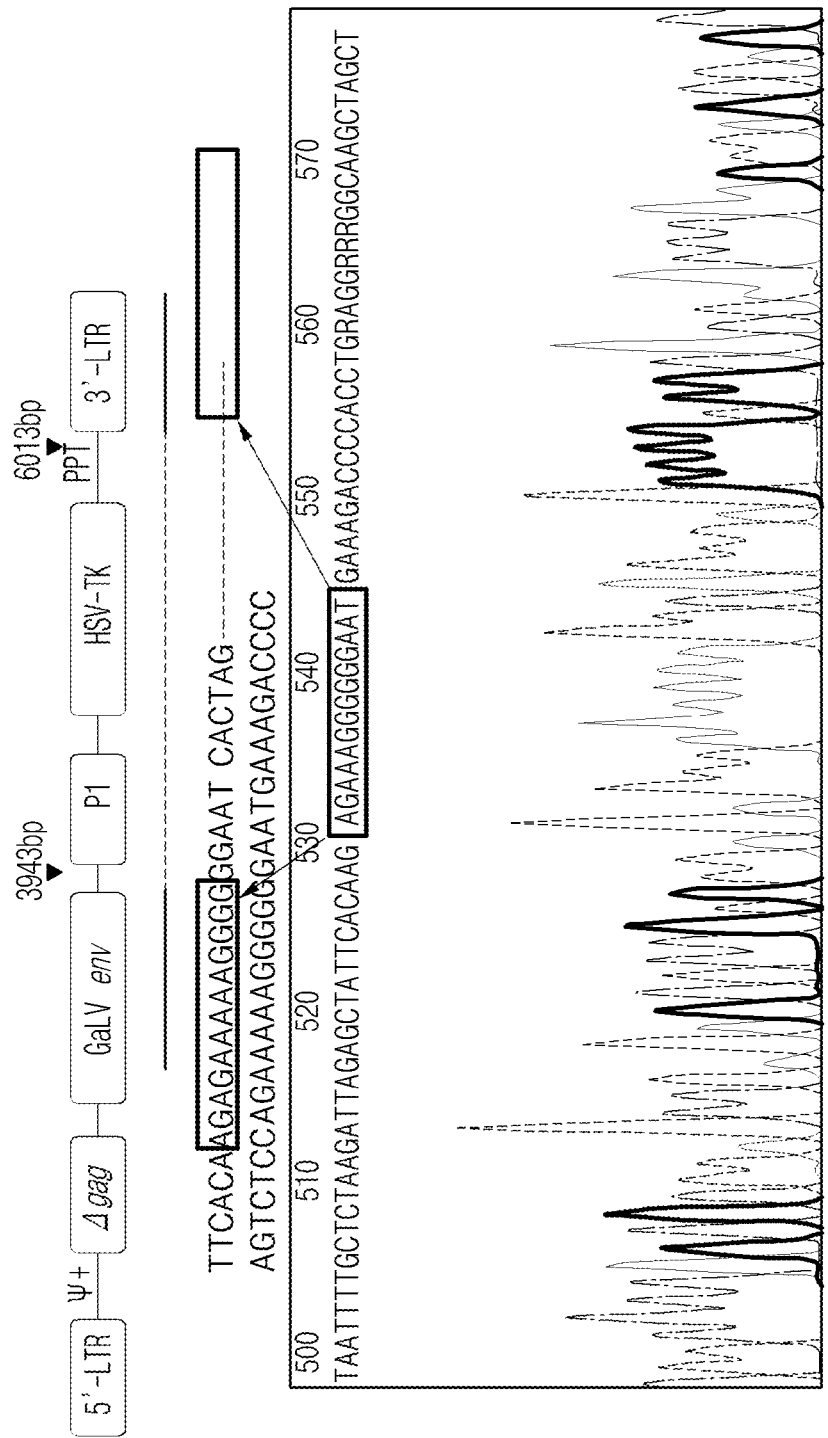
[Fig. 4]

[Fig. 5]
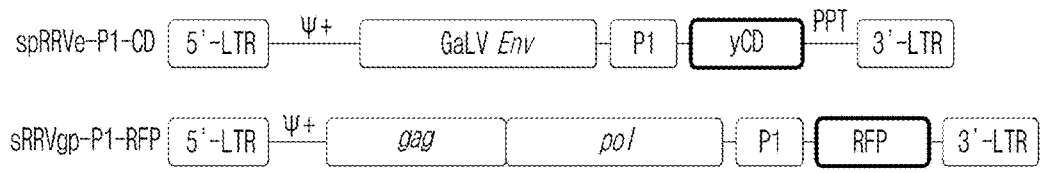
[Fig. 6]
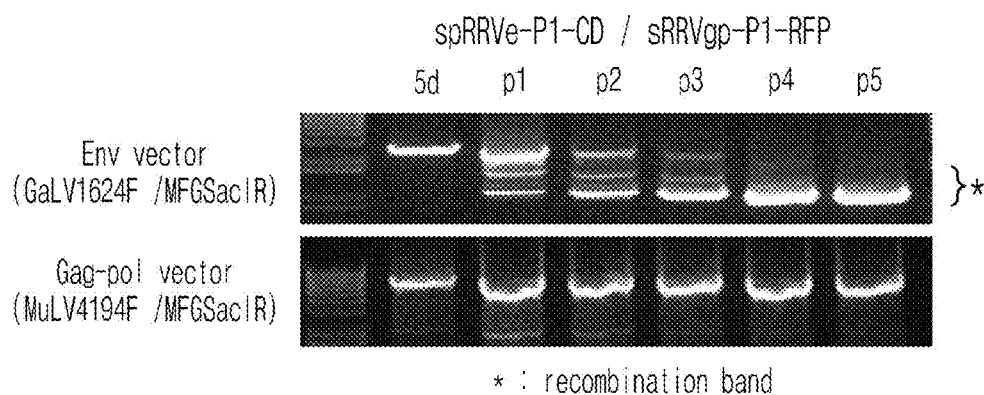
[Fig. 7]
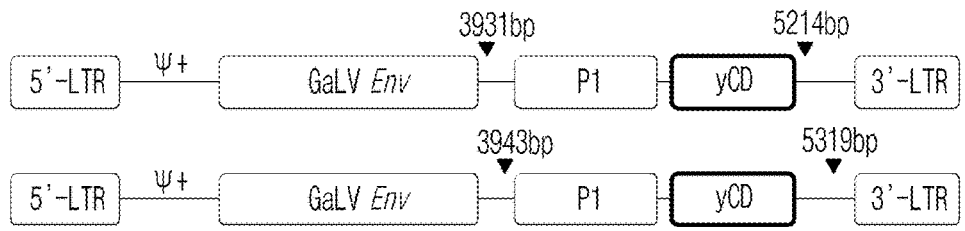

[Fig. 8]
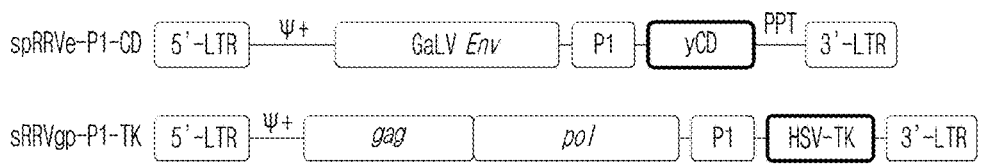
[Fig. 9]
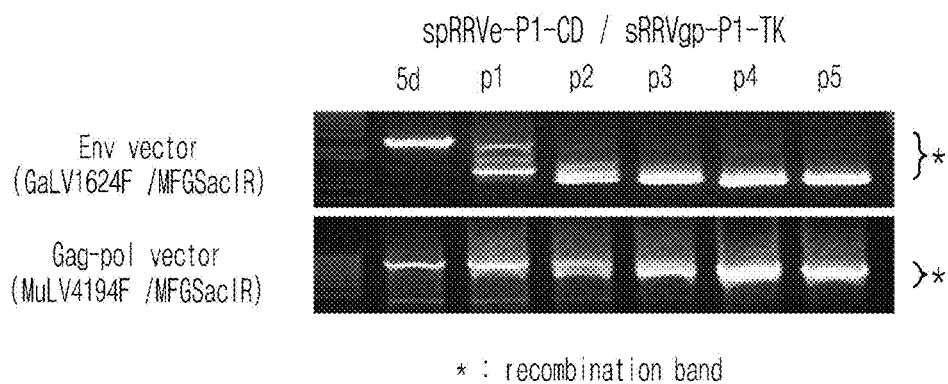
[Fig. 10]
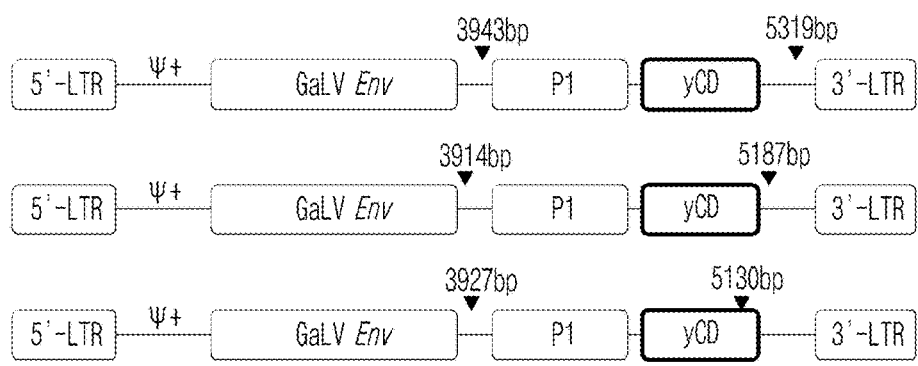

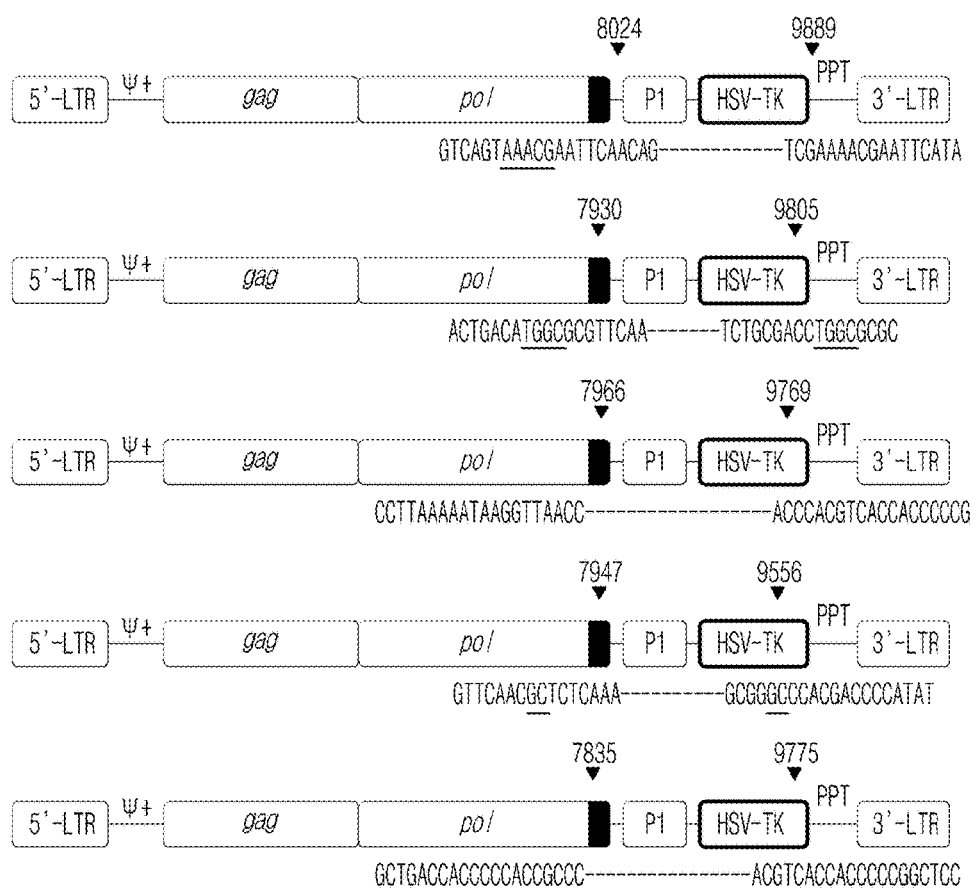
[Fig. 11]

[Fig. 12]

spRRVe-P1-CD/sRRVgp-P1-TK

[Fig. 13]
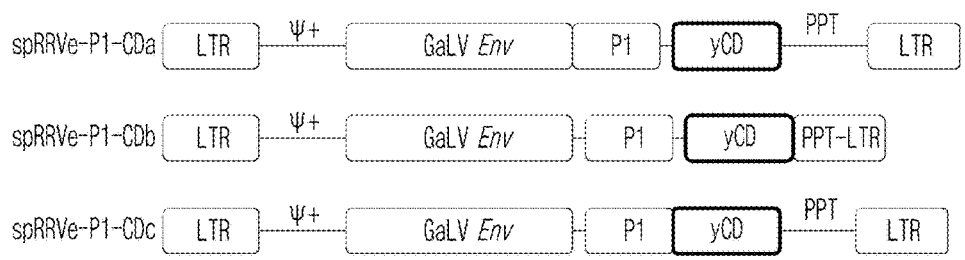
[Fig. 14]
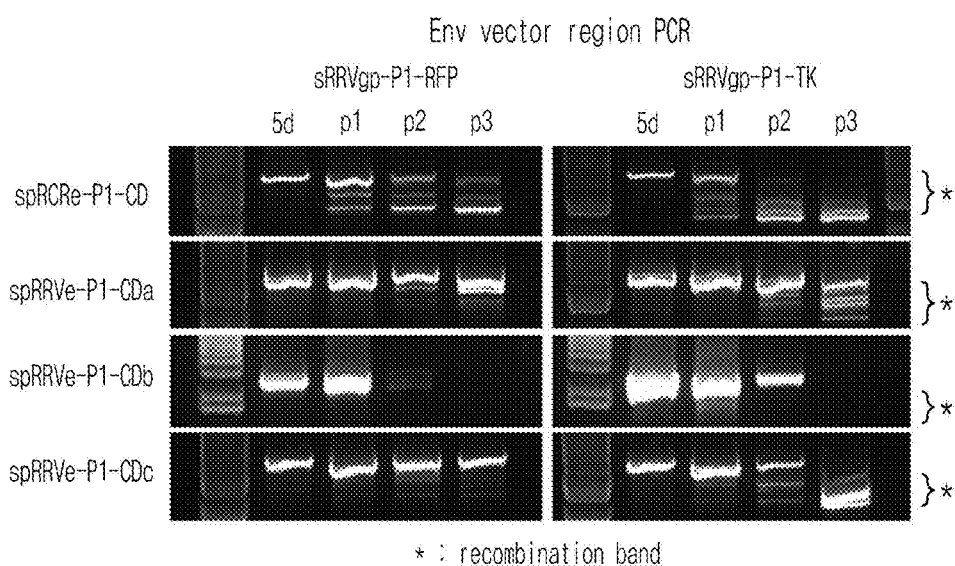

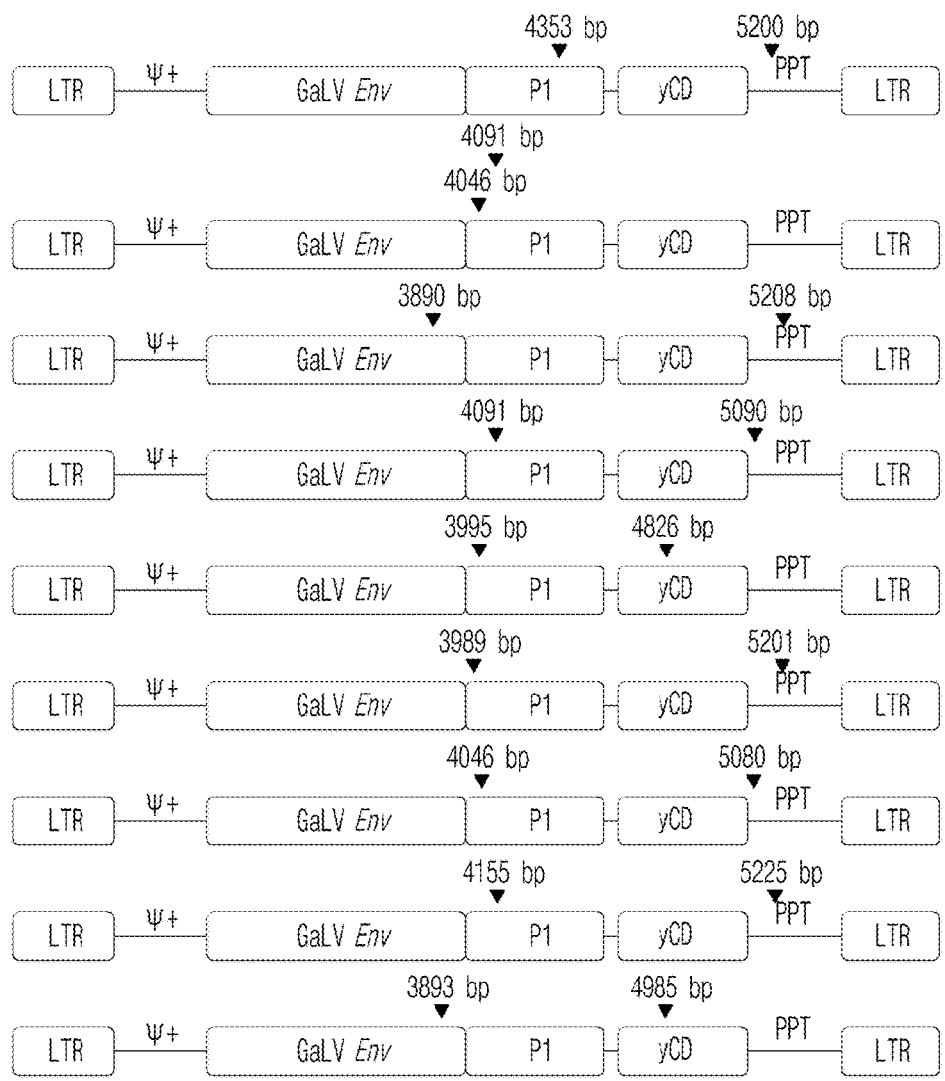
[Fig. 15]

[Fig. 16]
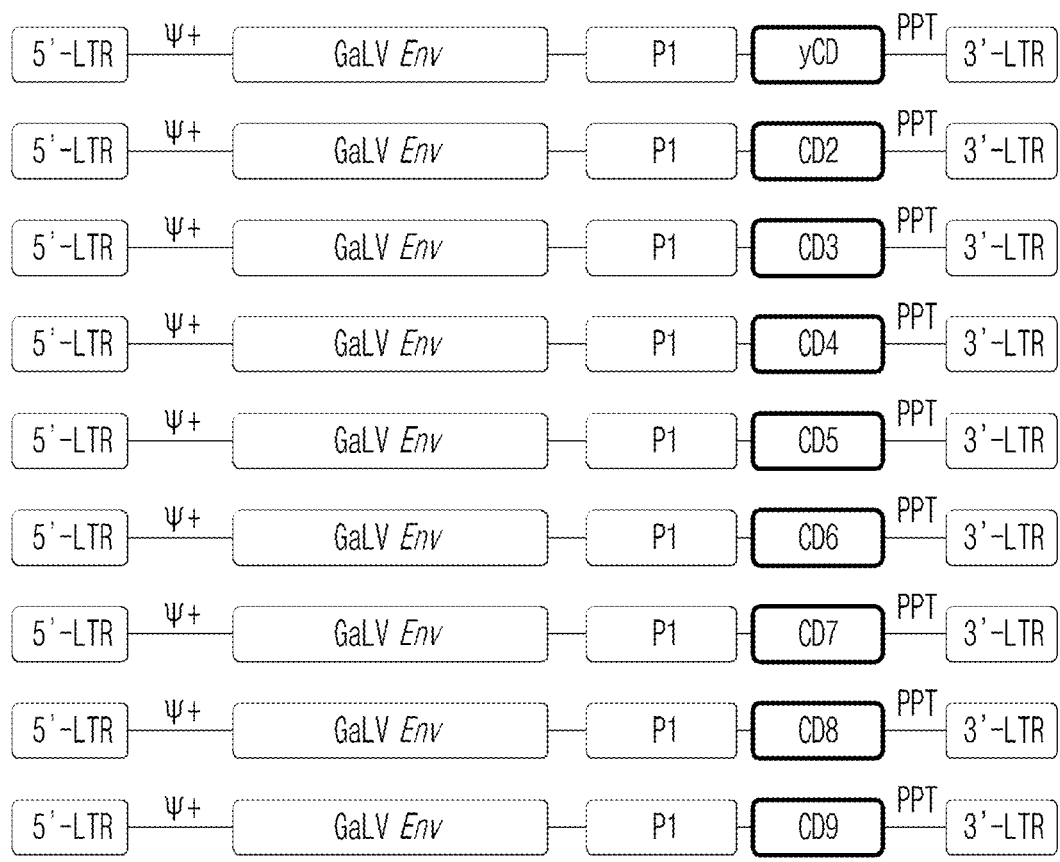

[Fig. 17a]
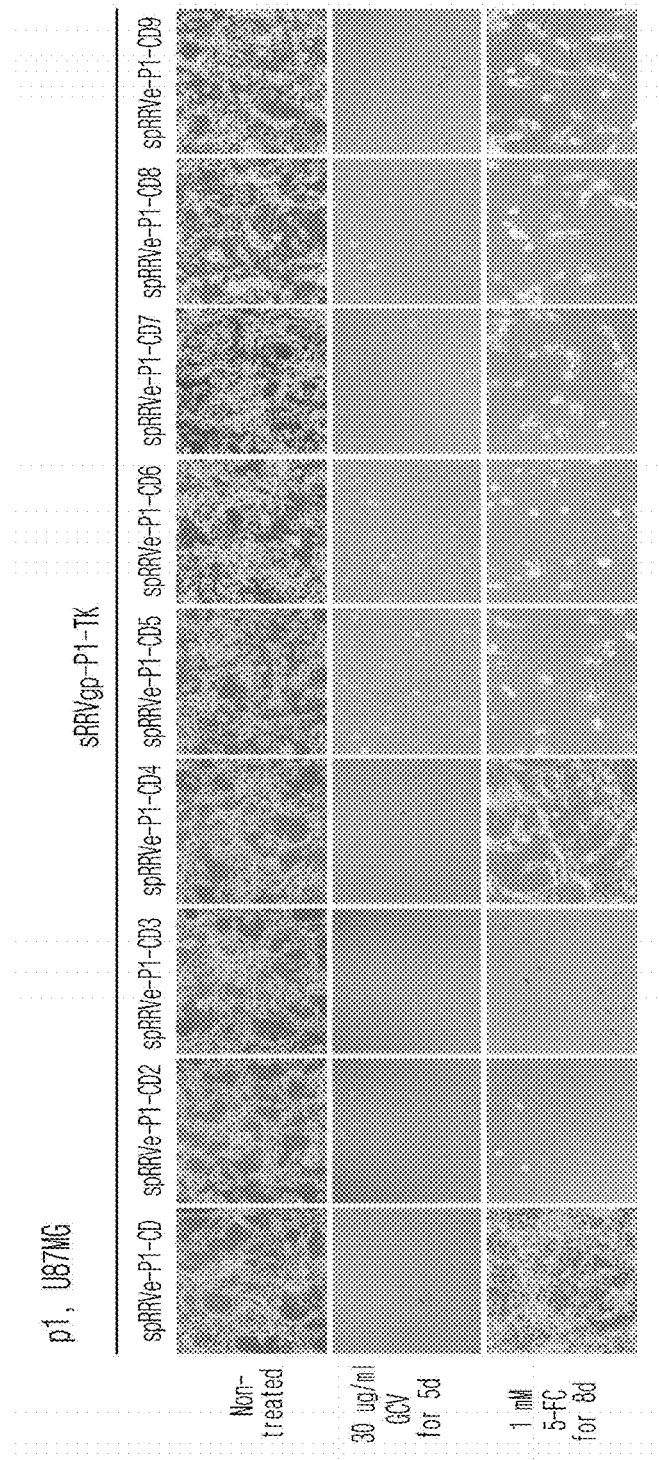

[Fig. 17d]
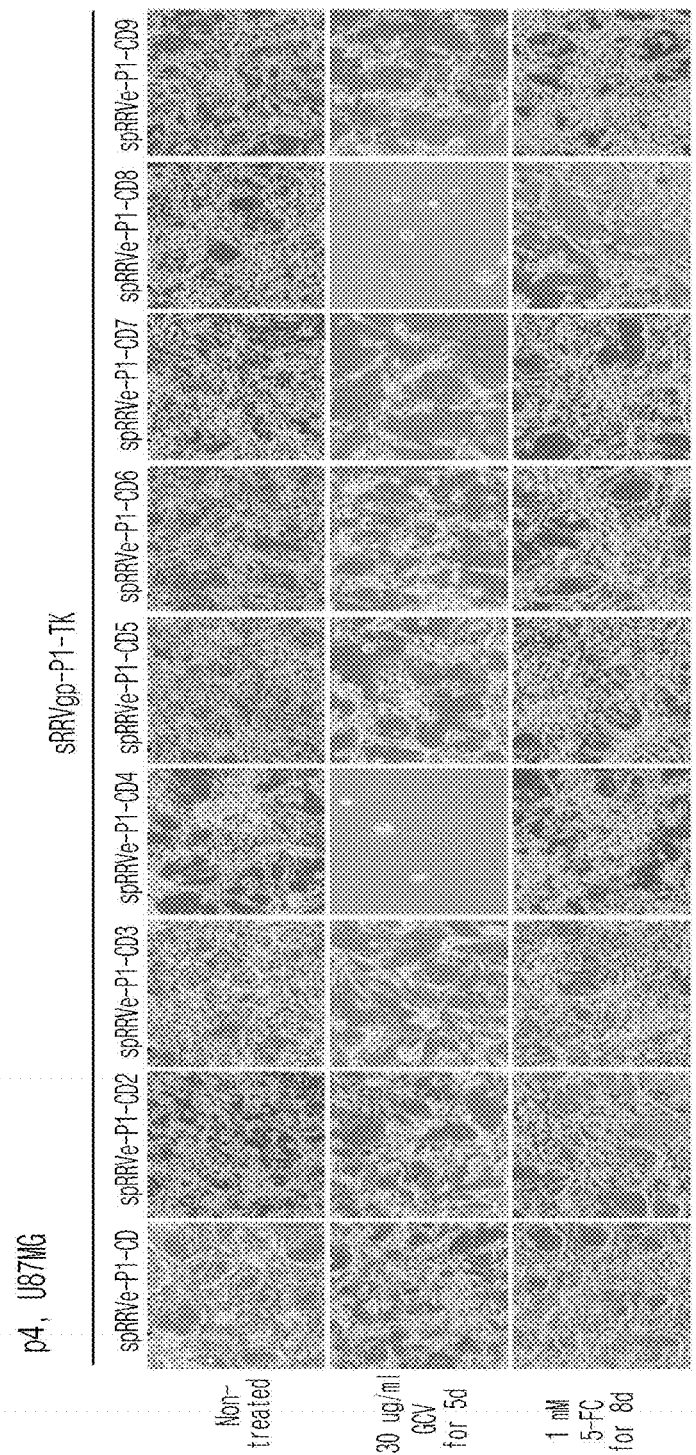

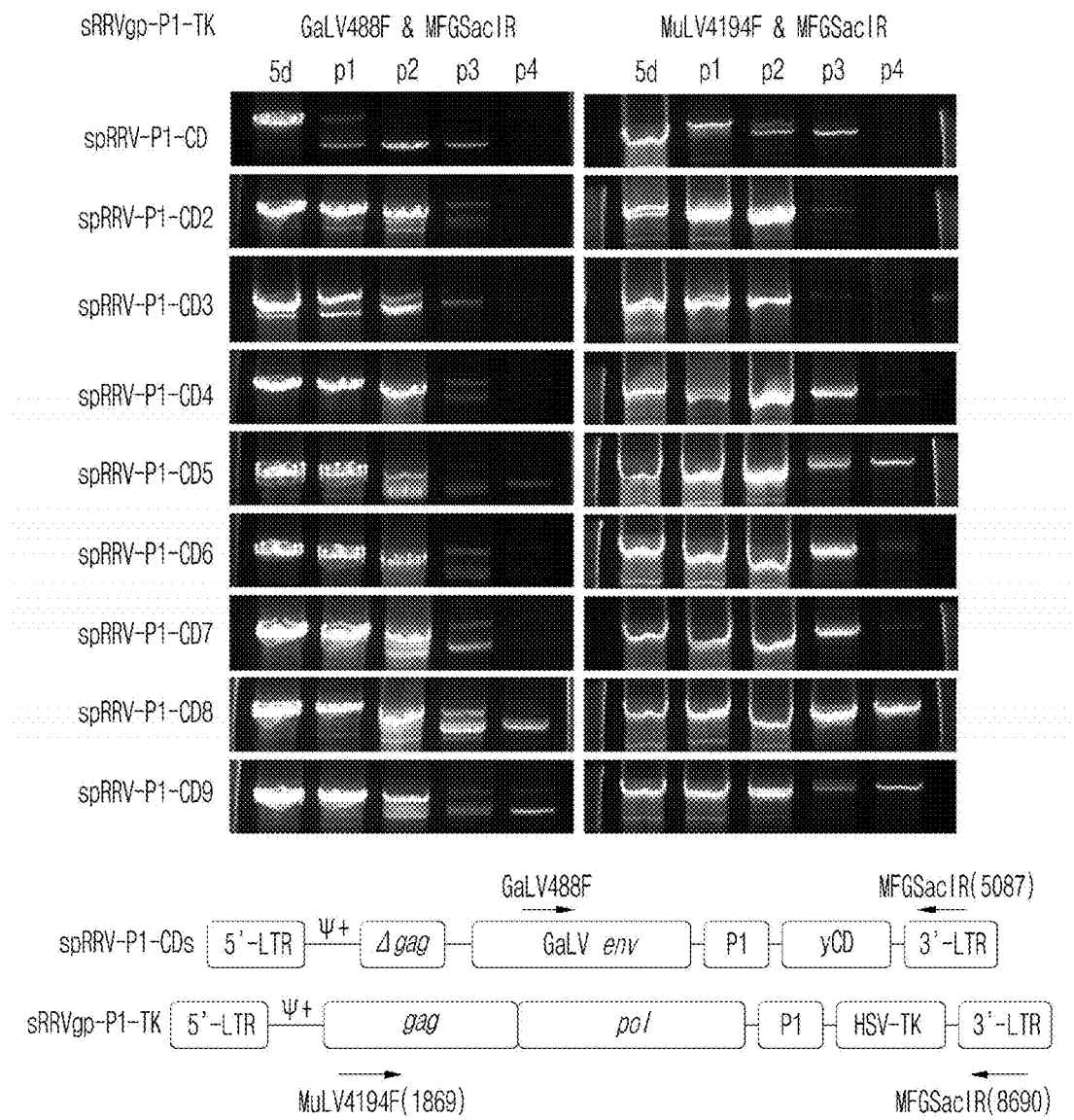
[Fig. 18]

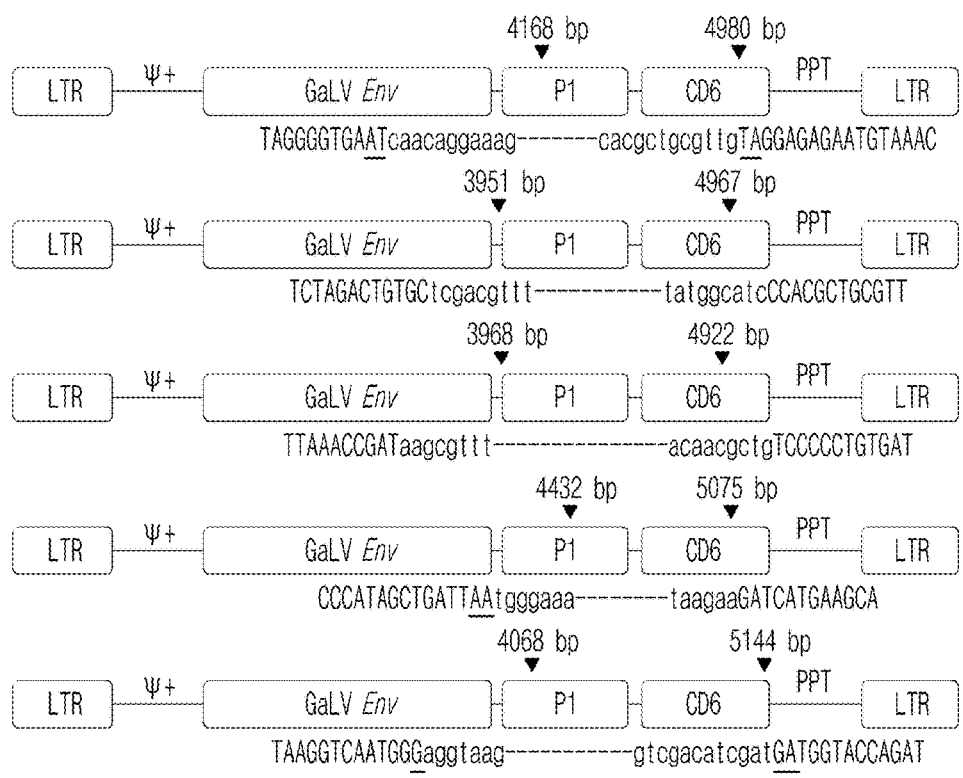
[Fig. 19a]

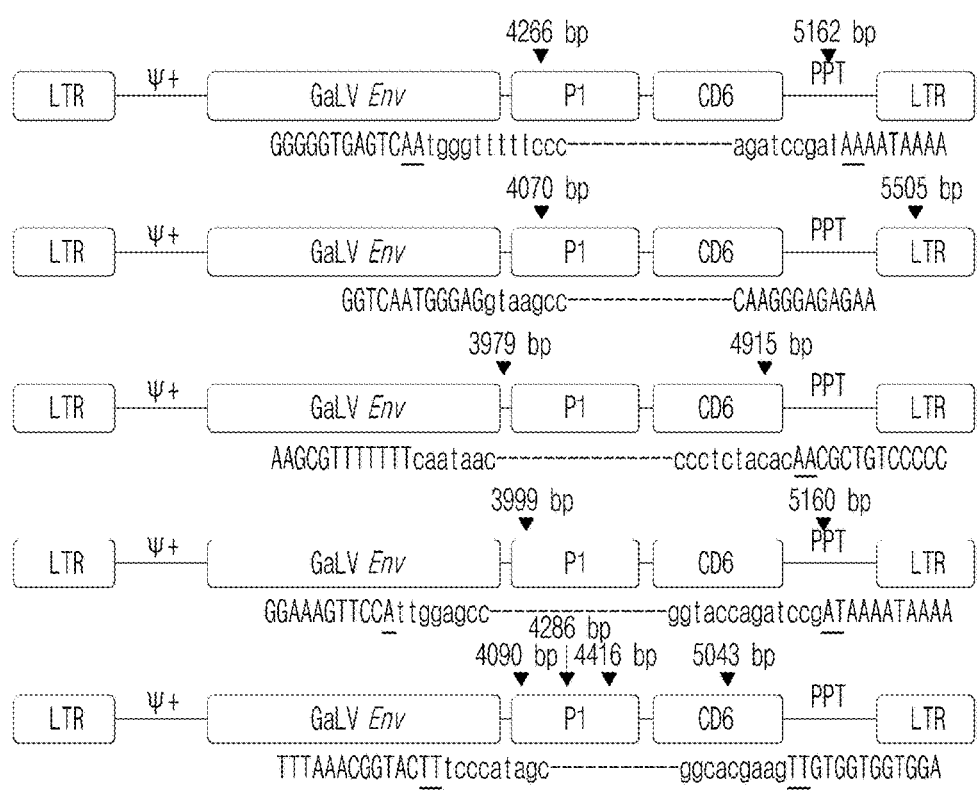
[Fig. 19b]

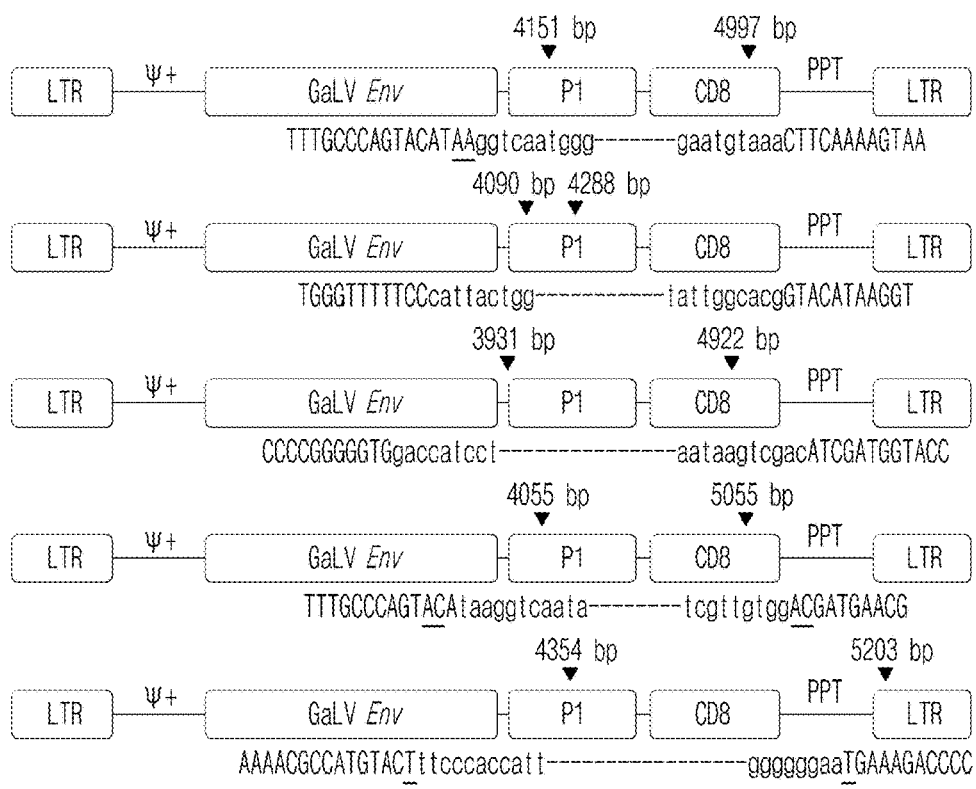
[Fig. 20a]

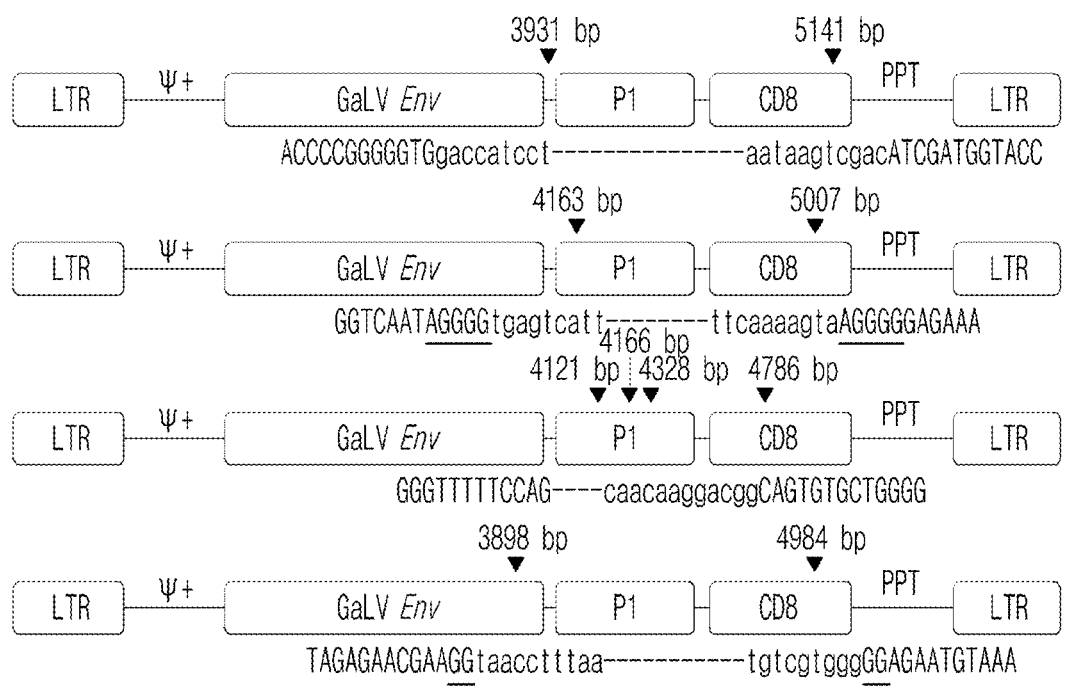
[Fig. 20b]

[Fig. 21]
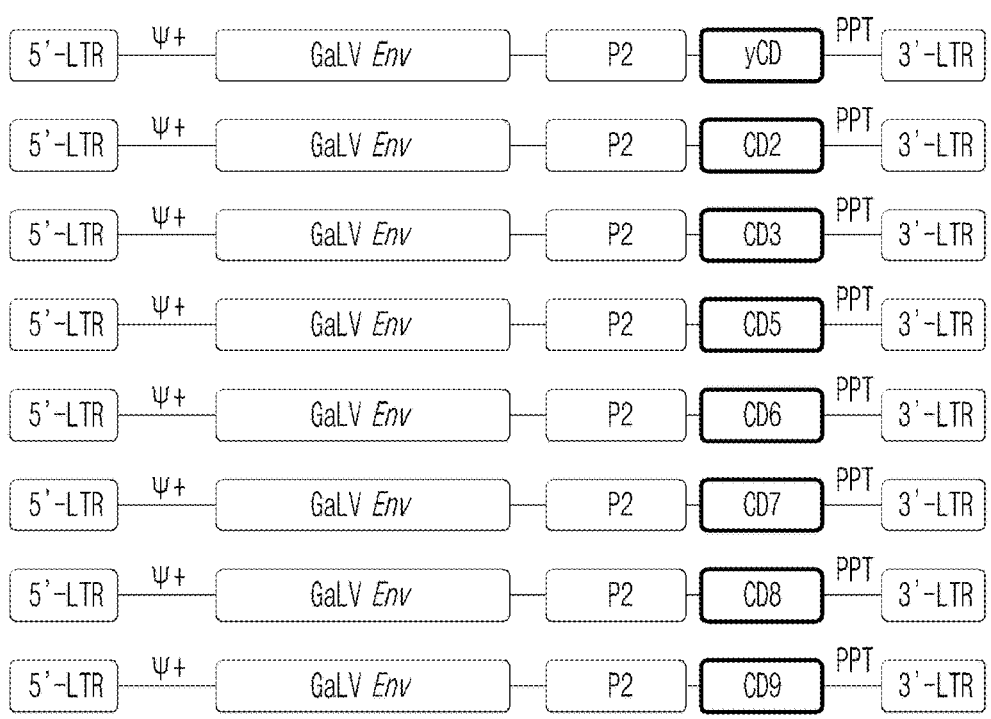

[Fig. 22f]
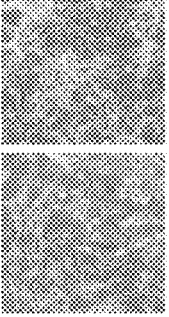

[Fig. 23]
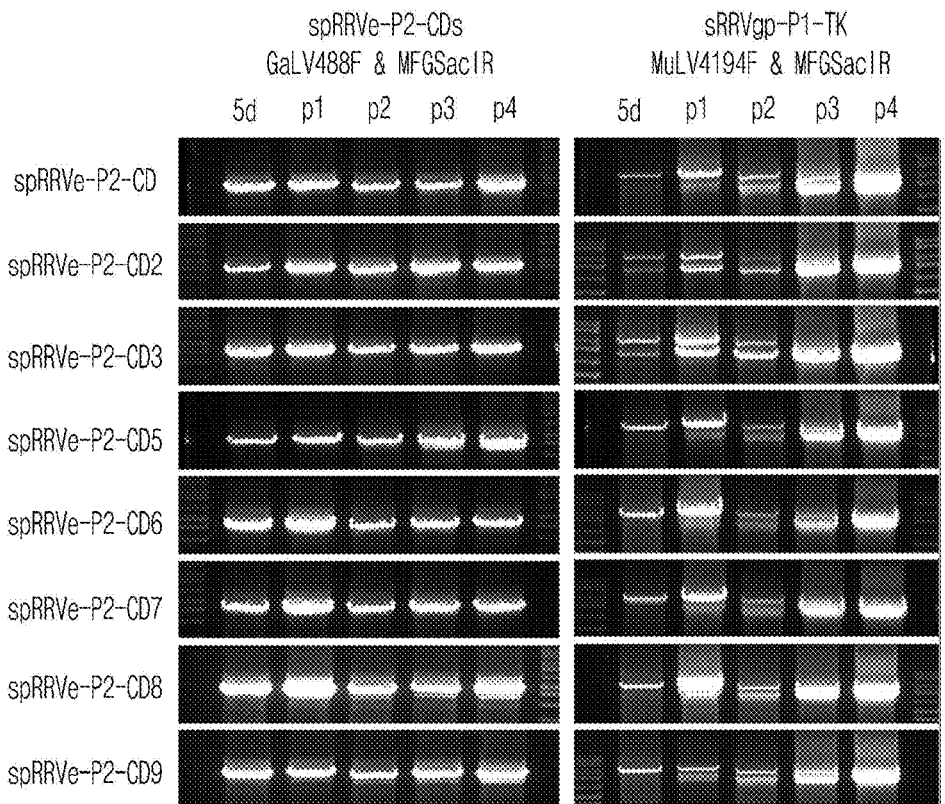
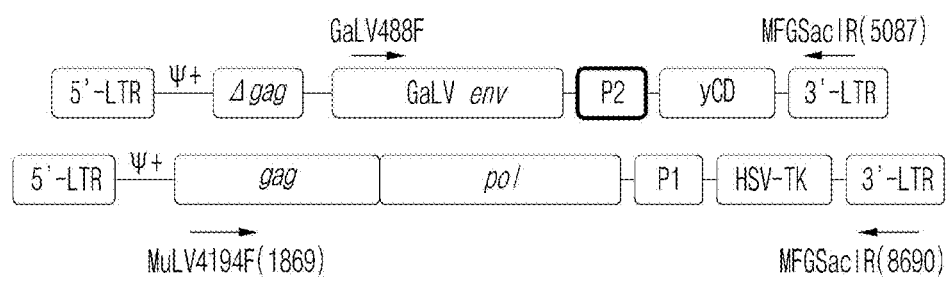

[Fig. 24]
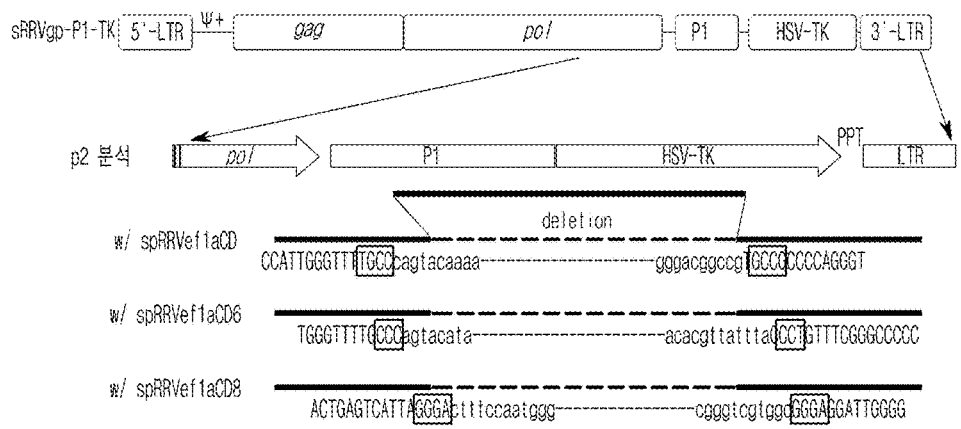
[Fig. 25]
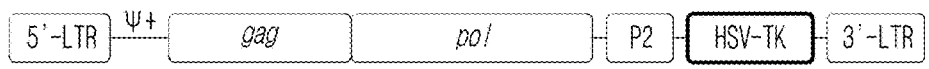

[Fig. 26a]
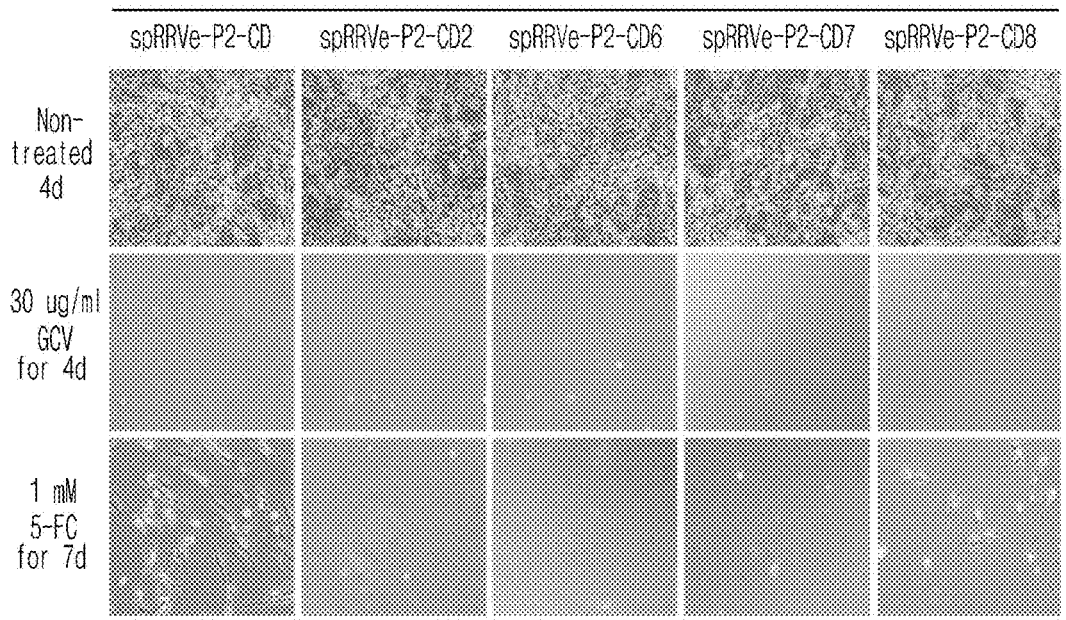
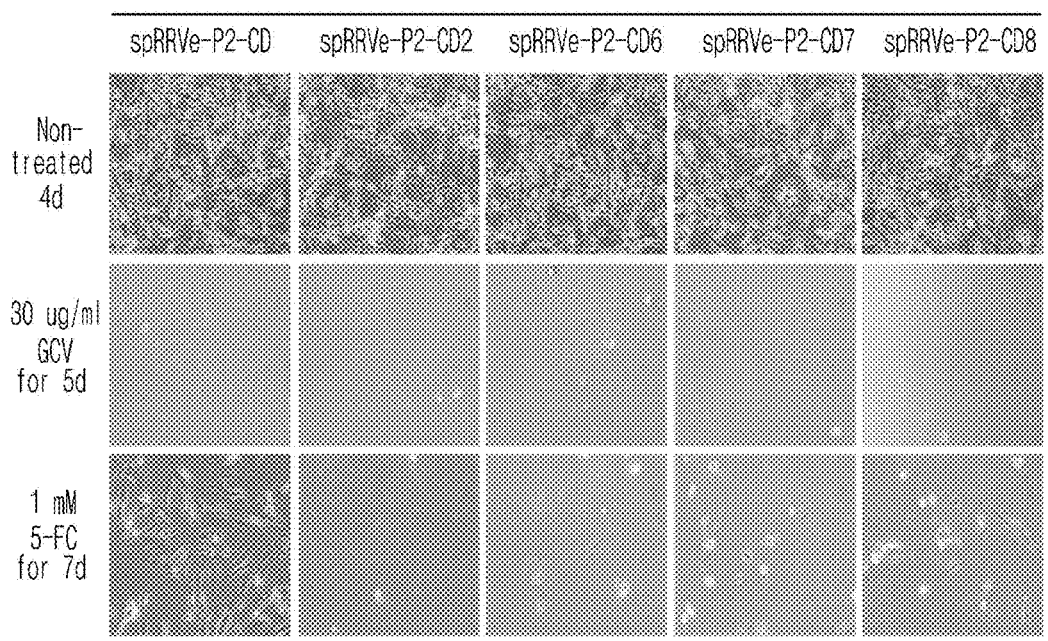

[Fig. 26b]
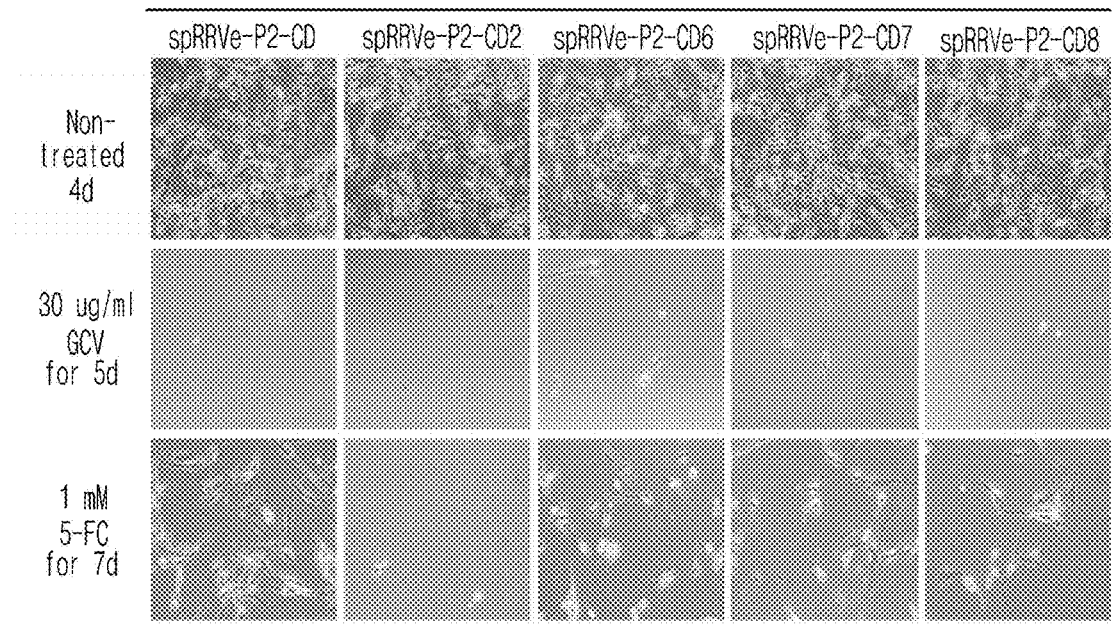
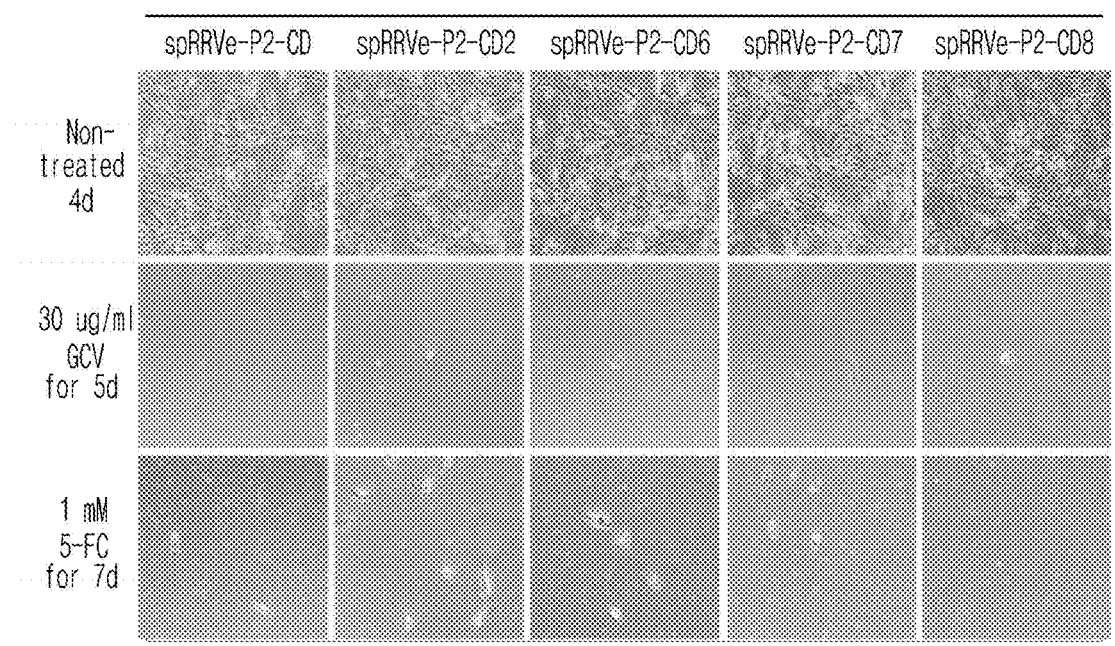

[Fig. 26c]

p9, U87MG sRRVgp-P2-TK

| | spRRVe-P2-CD | spRRVe-P2-CD2 | spRRVe-P2-CD6 | spRRVe-P2-CD7 | spRRVe-P2-CD8 |
|---|---|---|---|---|---|
| Non-treated 4d | | | | | |
| 30 ug/ml GCV for 5d | | | | | |
| 1 mM 5-FC for 7d | | | | | | p11, U87MG sRRVgp-P2-TK

| | spRRVe-P2-CD | spRRVe-P2-CD2 | spRRVe-P2-CD6 | spRRVe-P2-CD7 | spRRVe-P2-CD8 |
|---|---|---|---|---|---|
| Non-treated 4d | | | | | |
| 30 ug/ml GCV for 5d | | | | | |
| 1 mM 5-FC for 7d | | | | | |

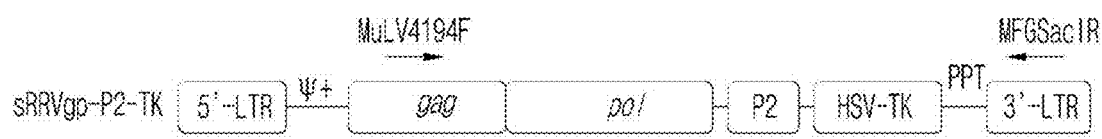

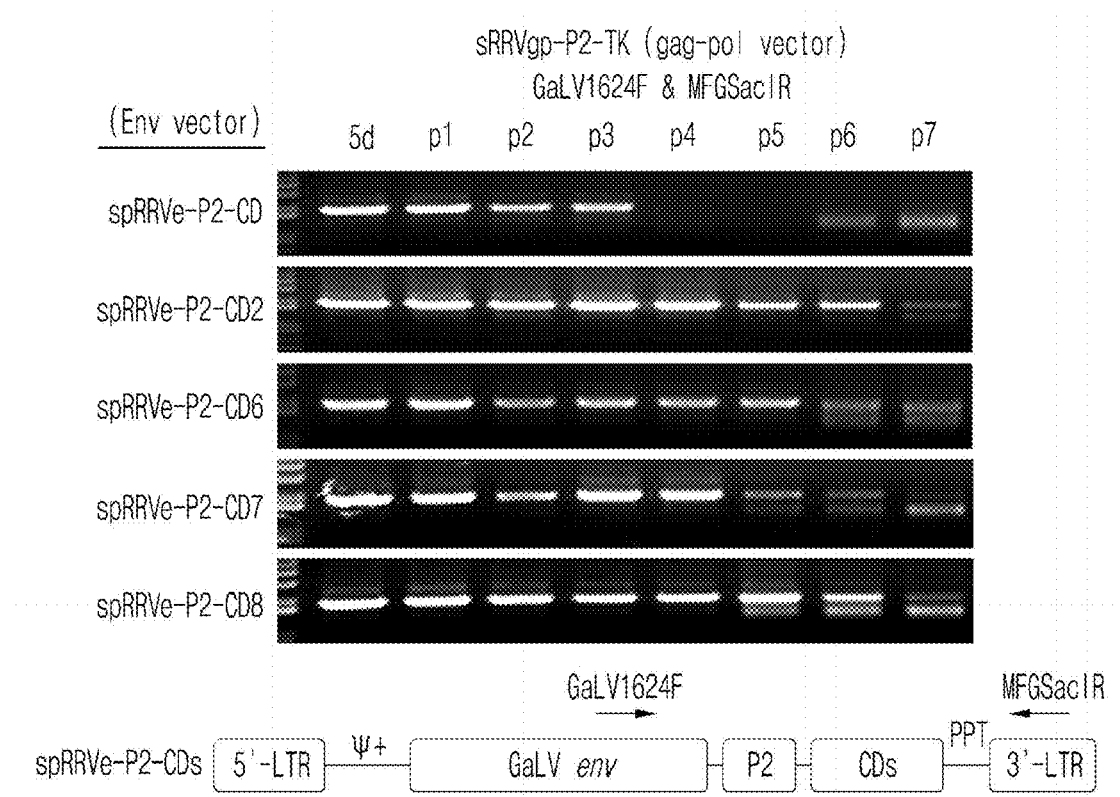
[Fig. 27b]

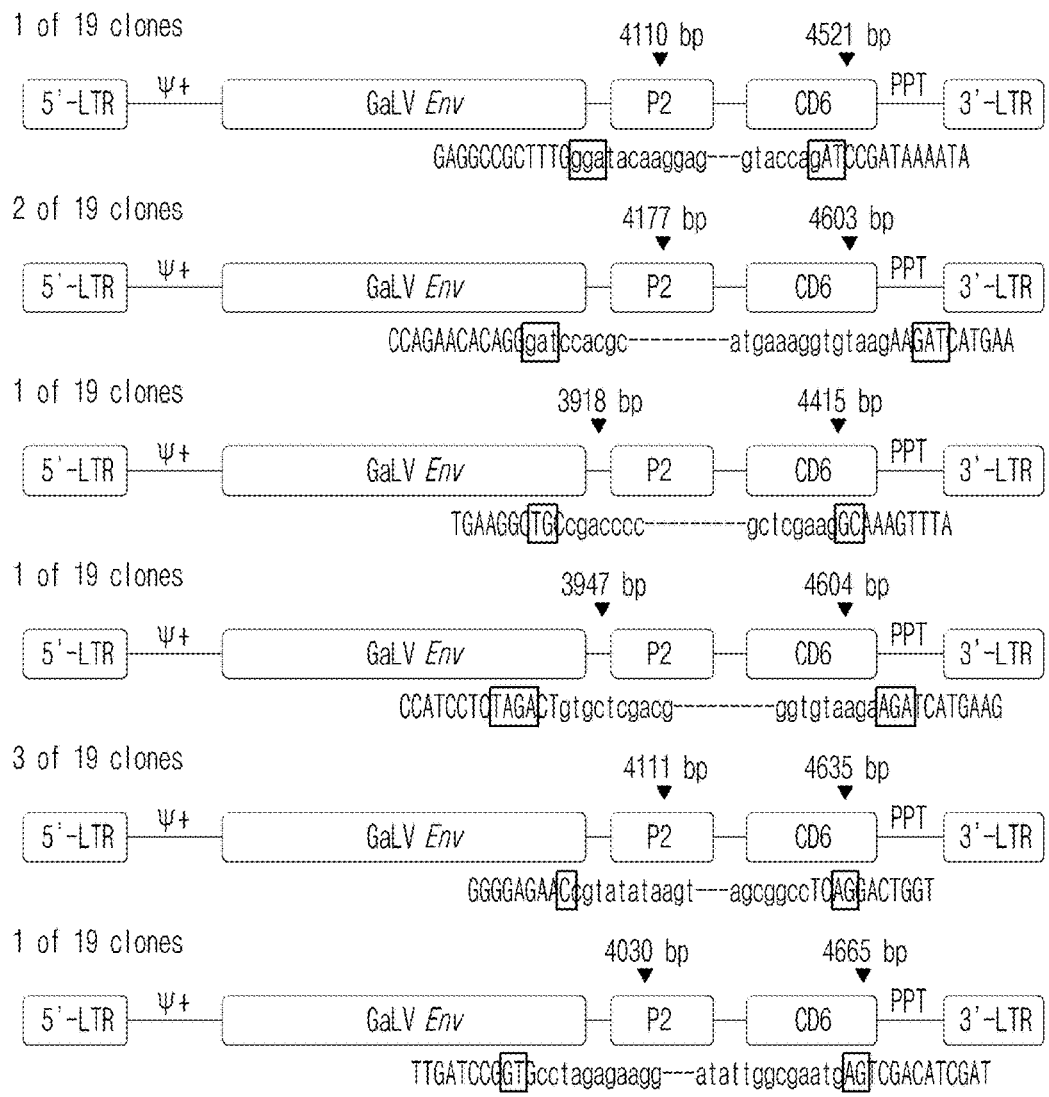
[Fig. 28a]

[Fig. 28b]
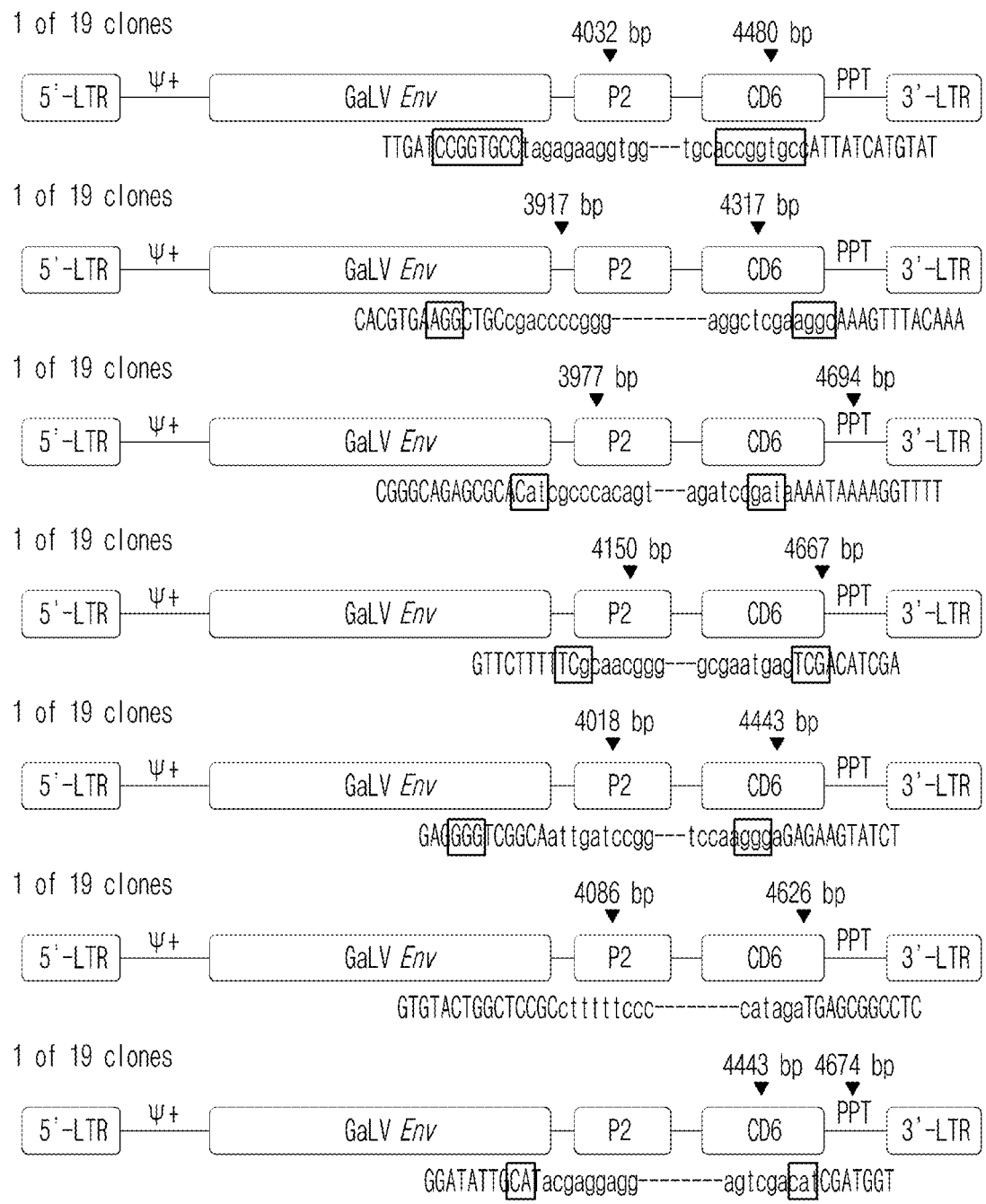

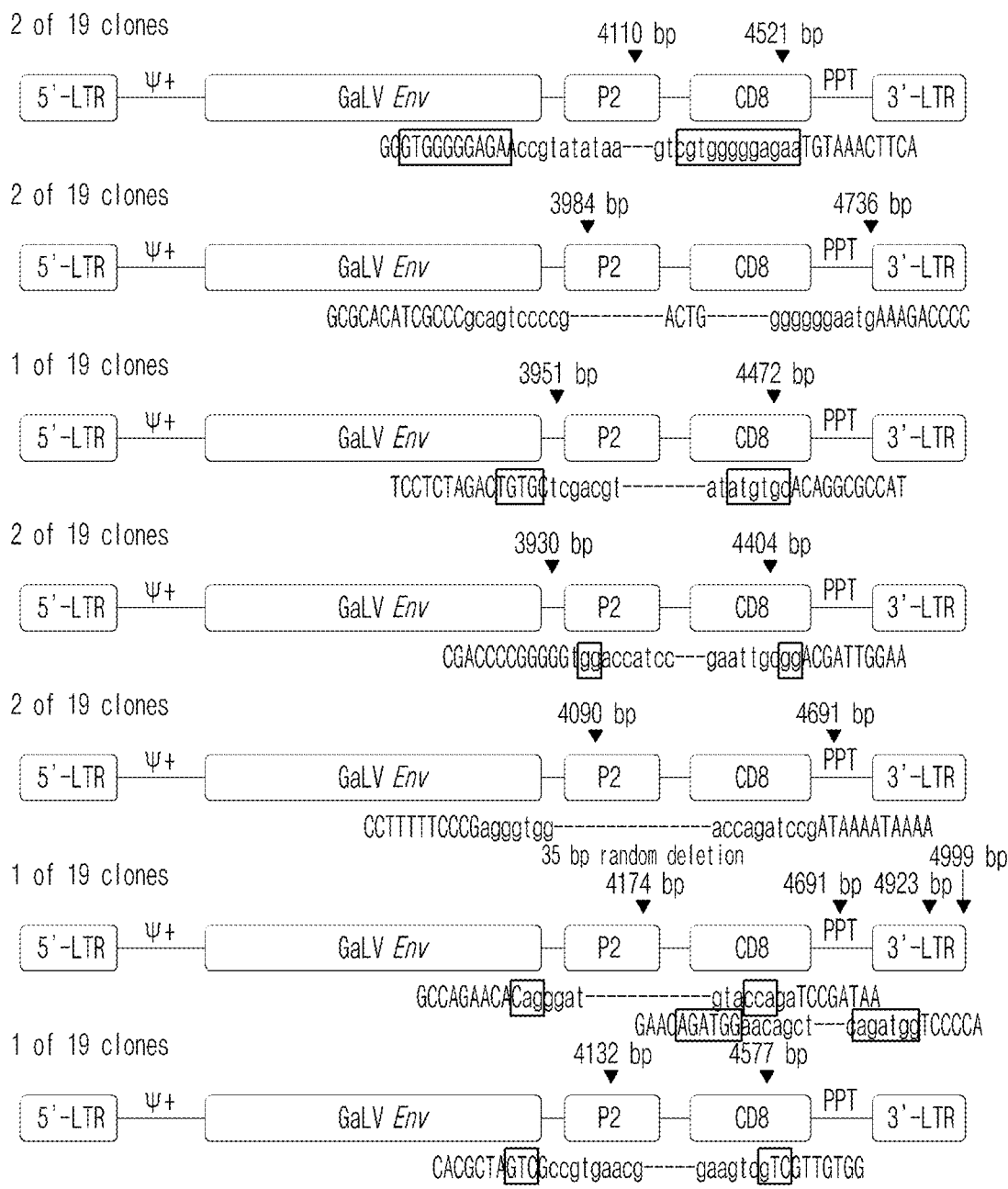
[Fig. 29a]

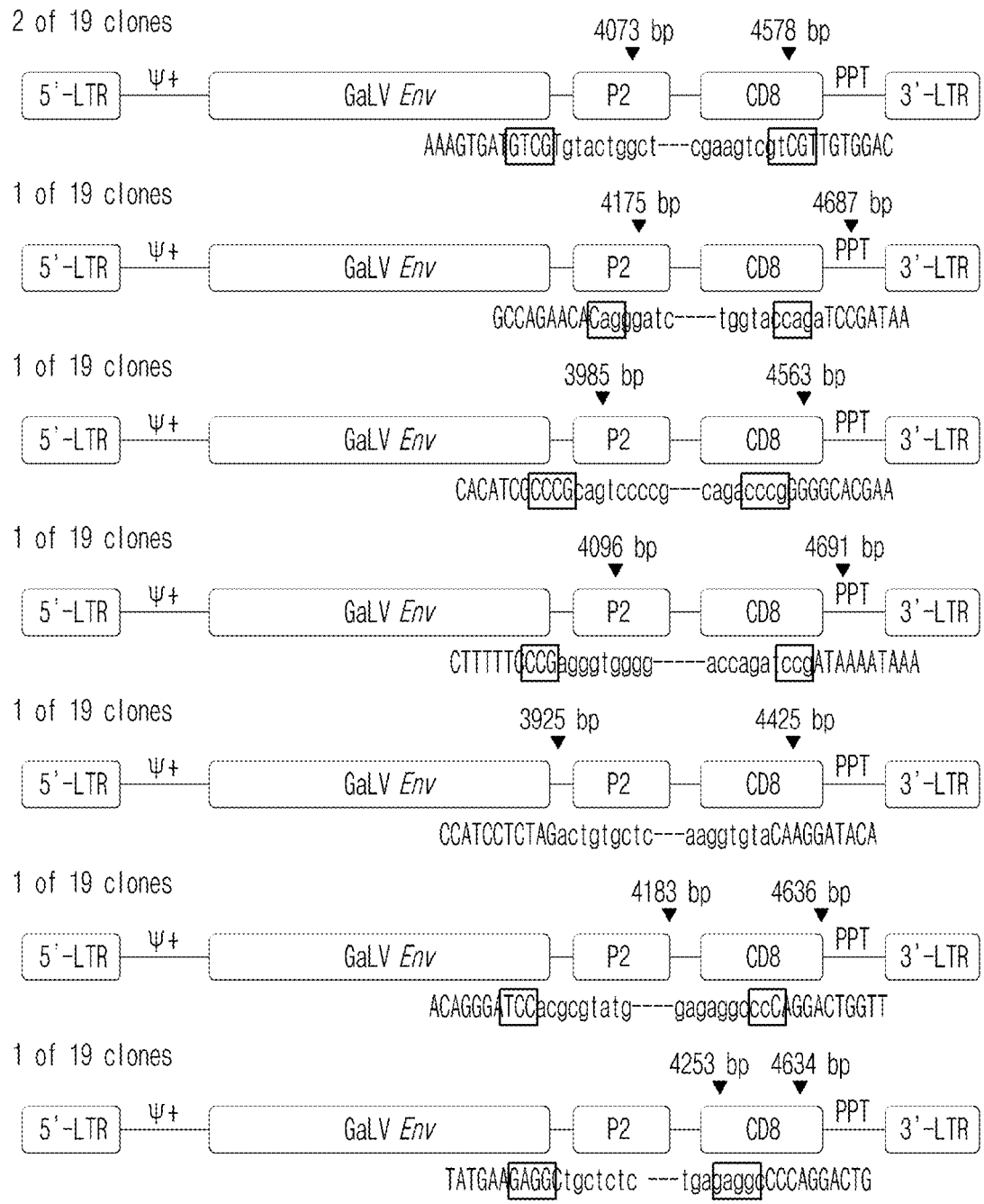
[Fig. 29b]

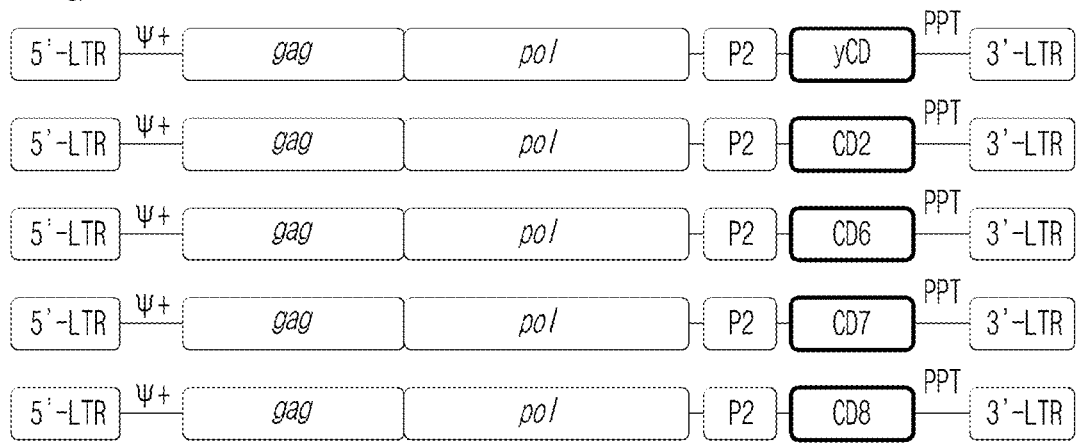

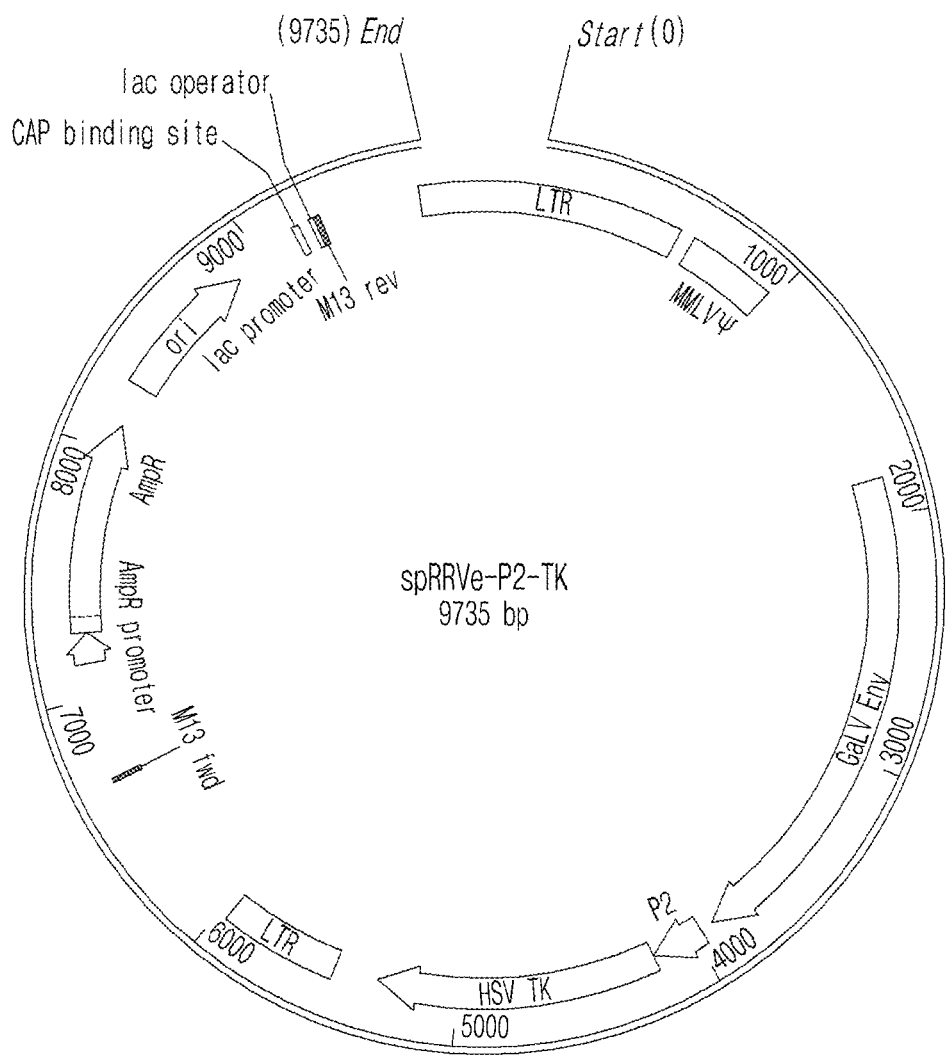
[Fig. 32]

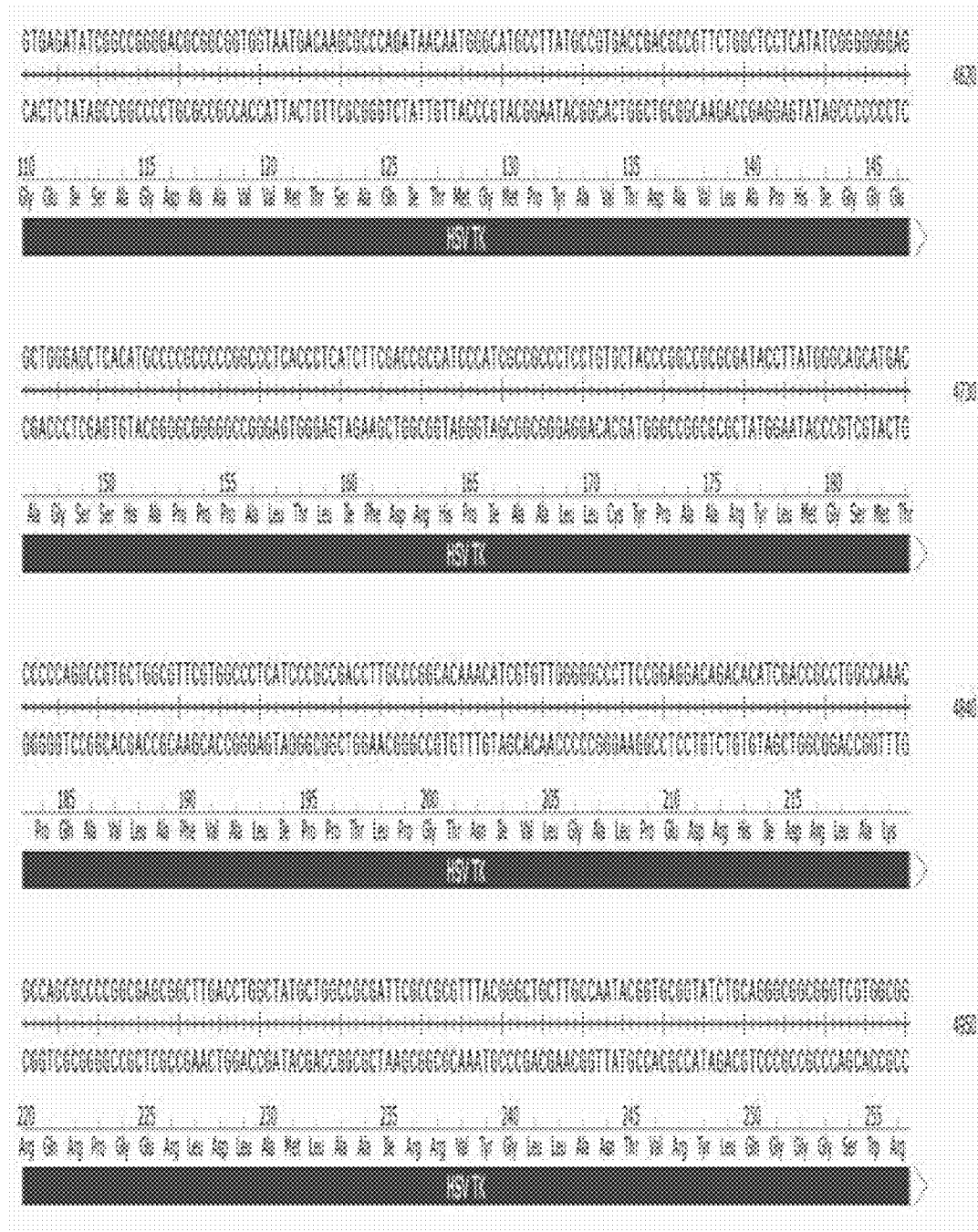
[Fig. 33i]

[Fig. 33n]
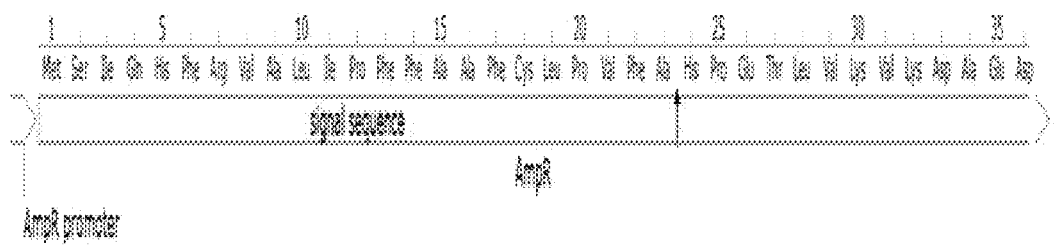
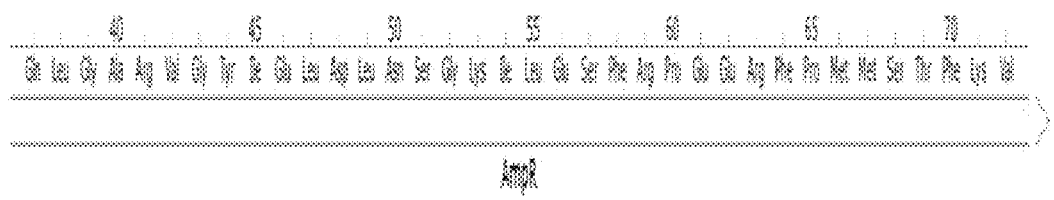
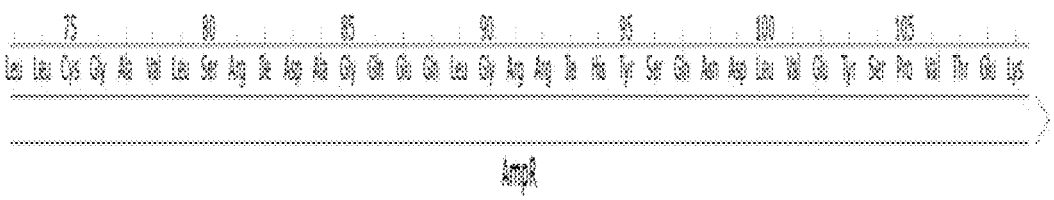

[Fig. 34]
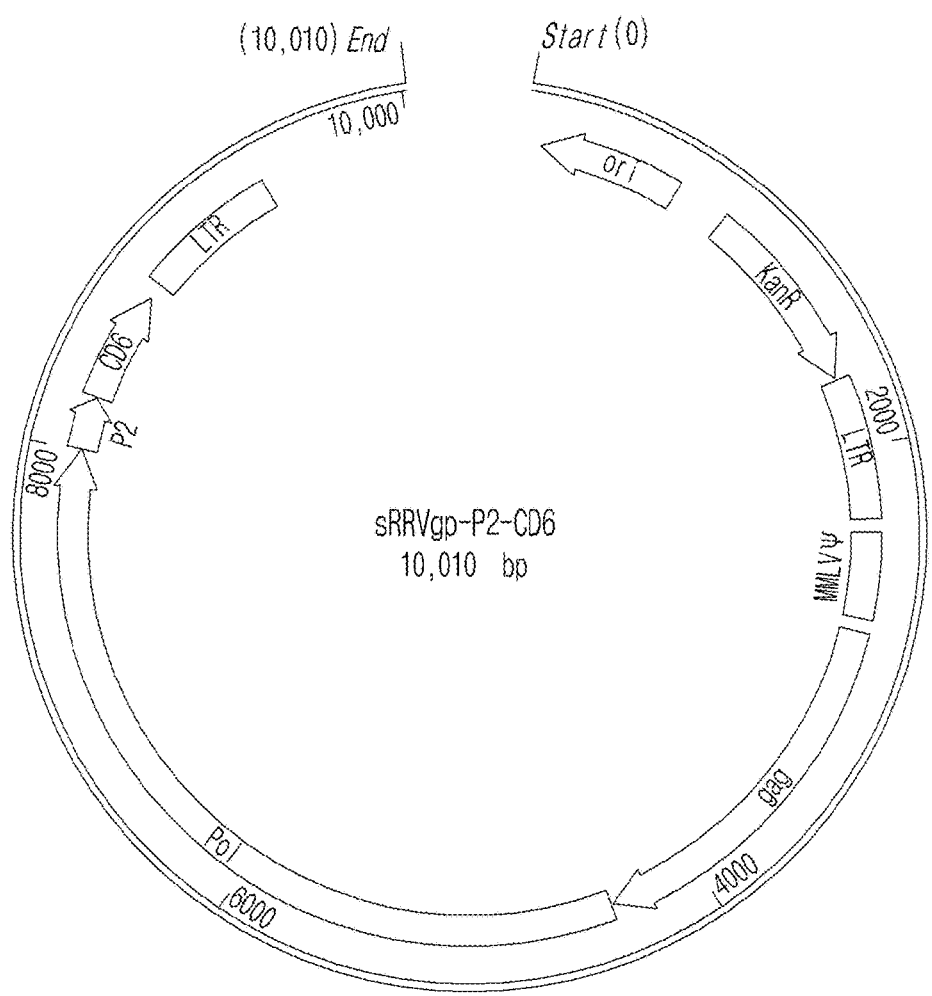

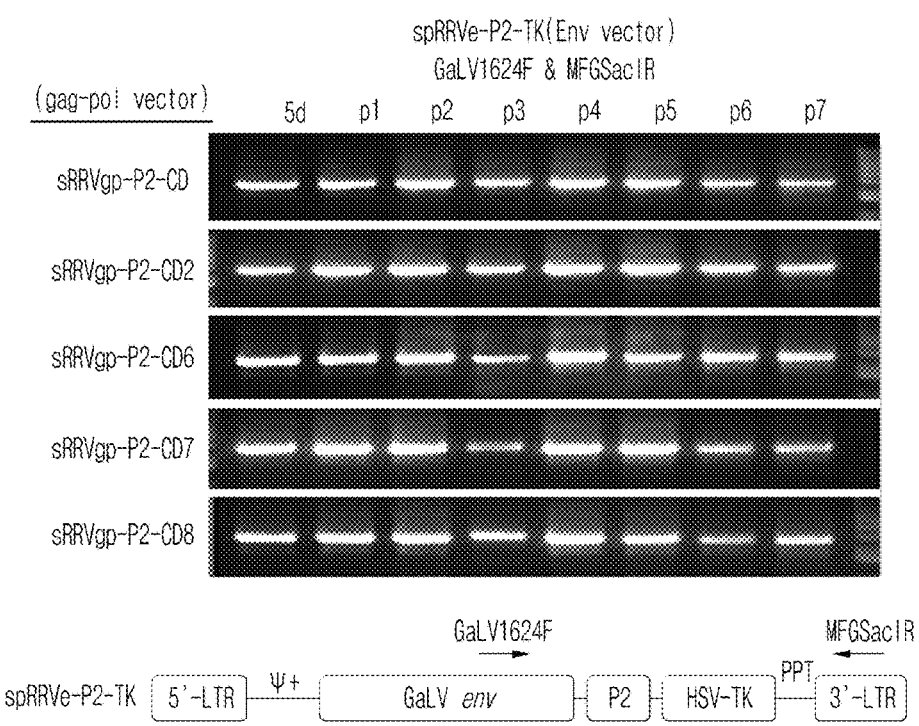
[Fig. 36a]

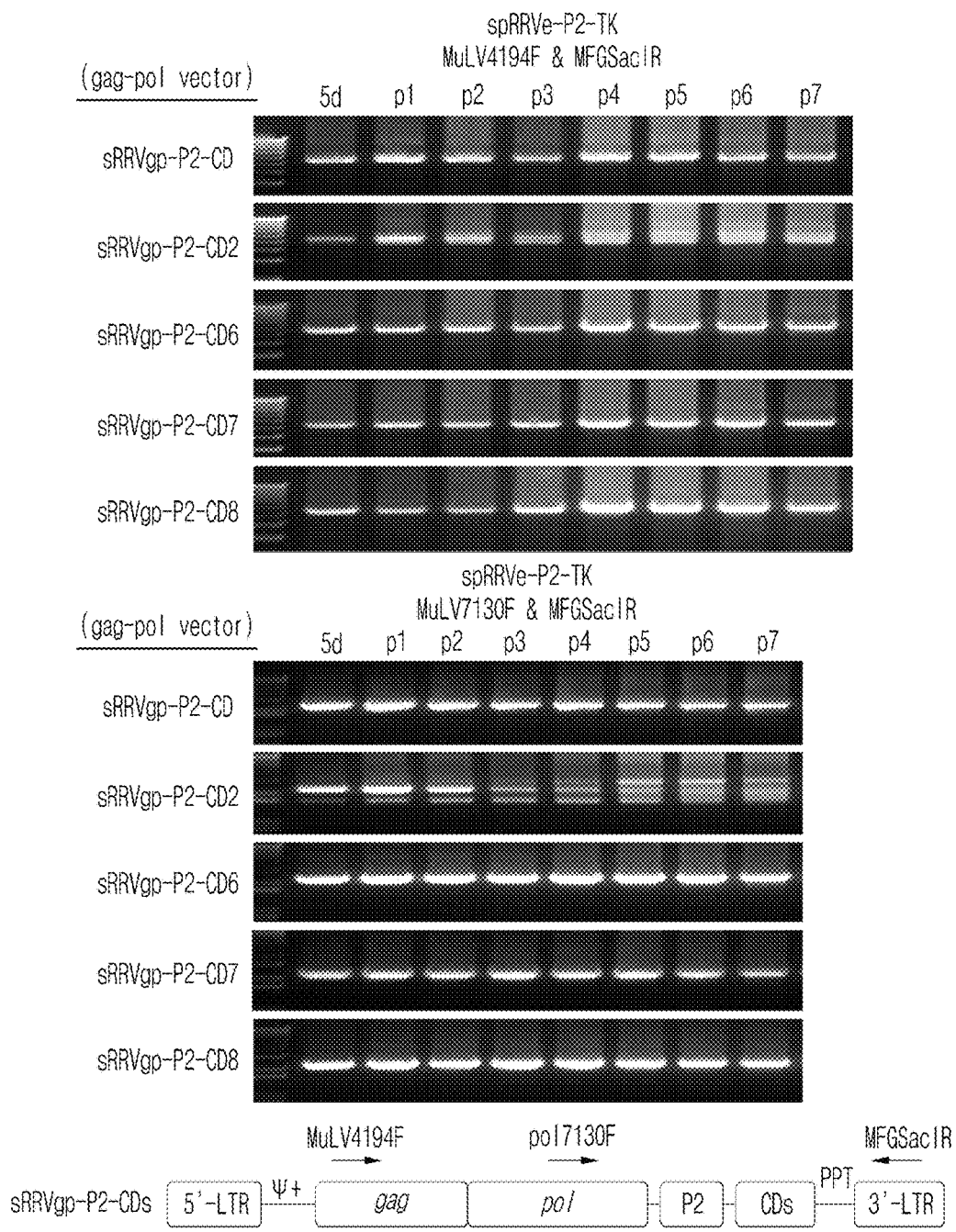
[Fig. 36b]

[Fig. 37a]
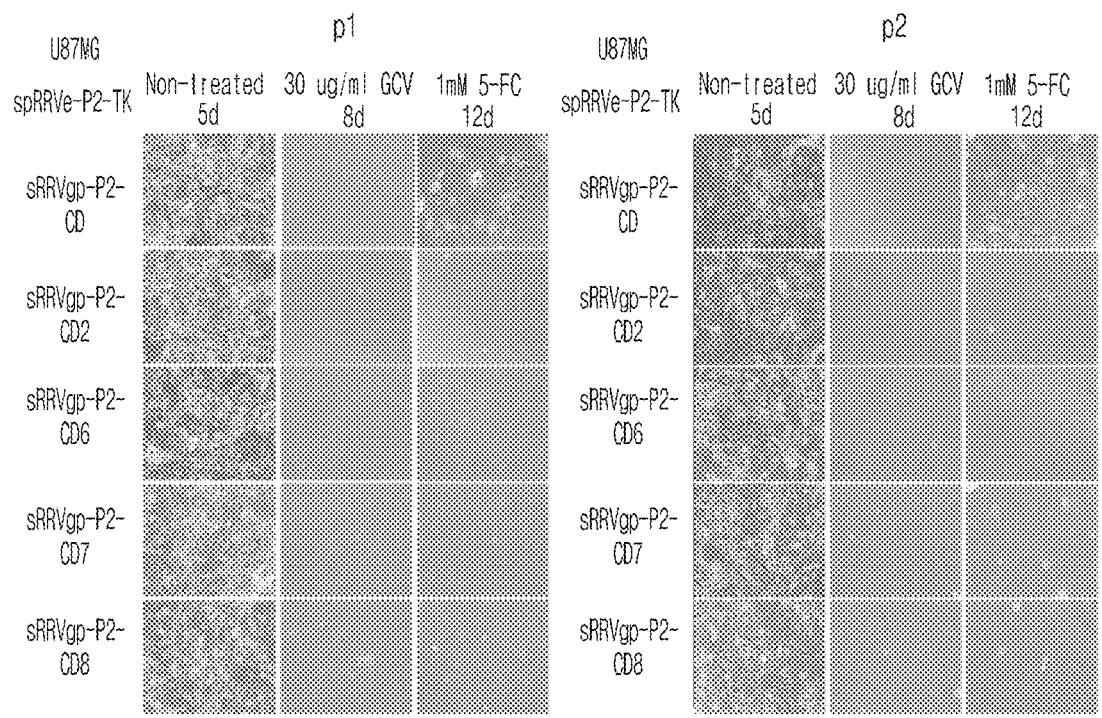

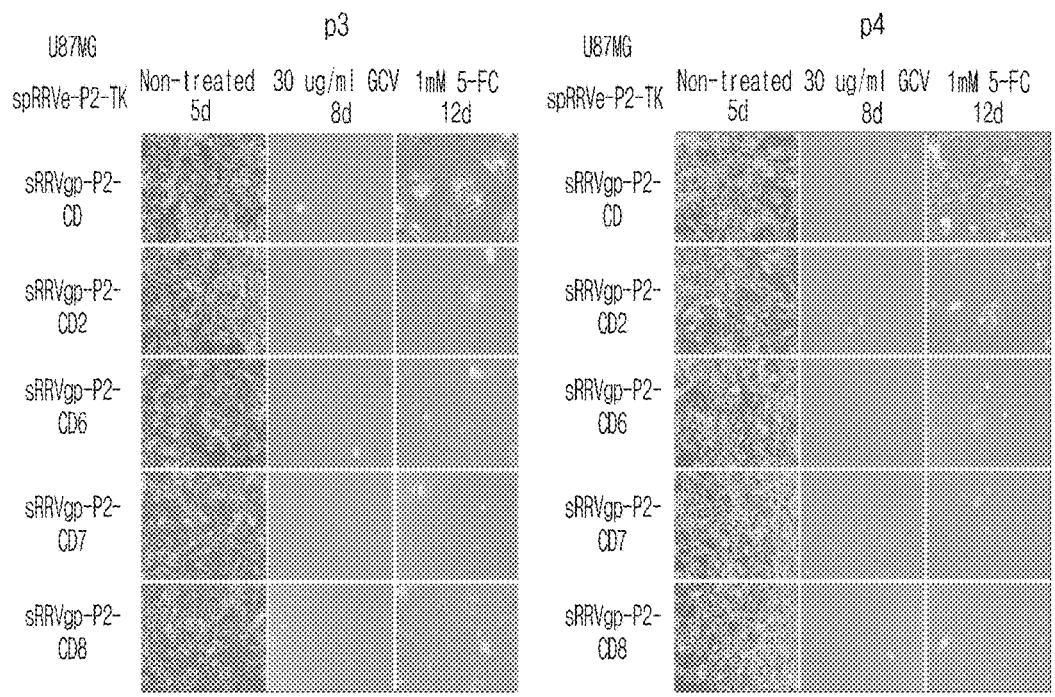
[Fig. 37b]

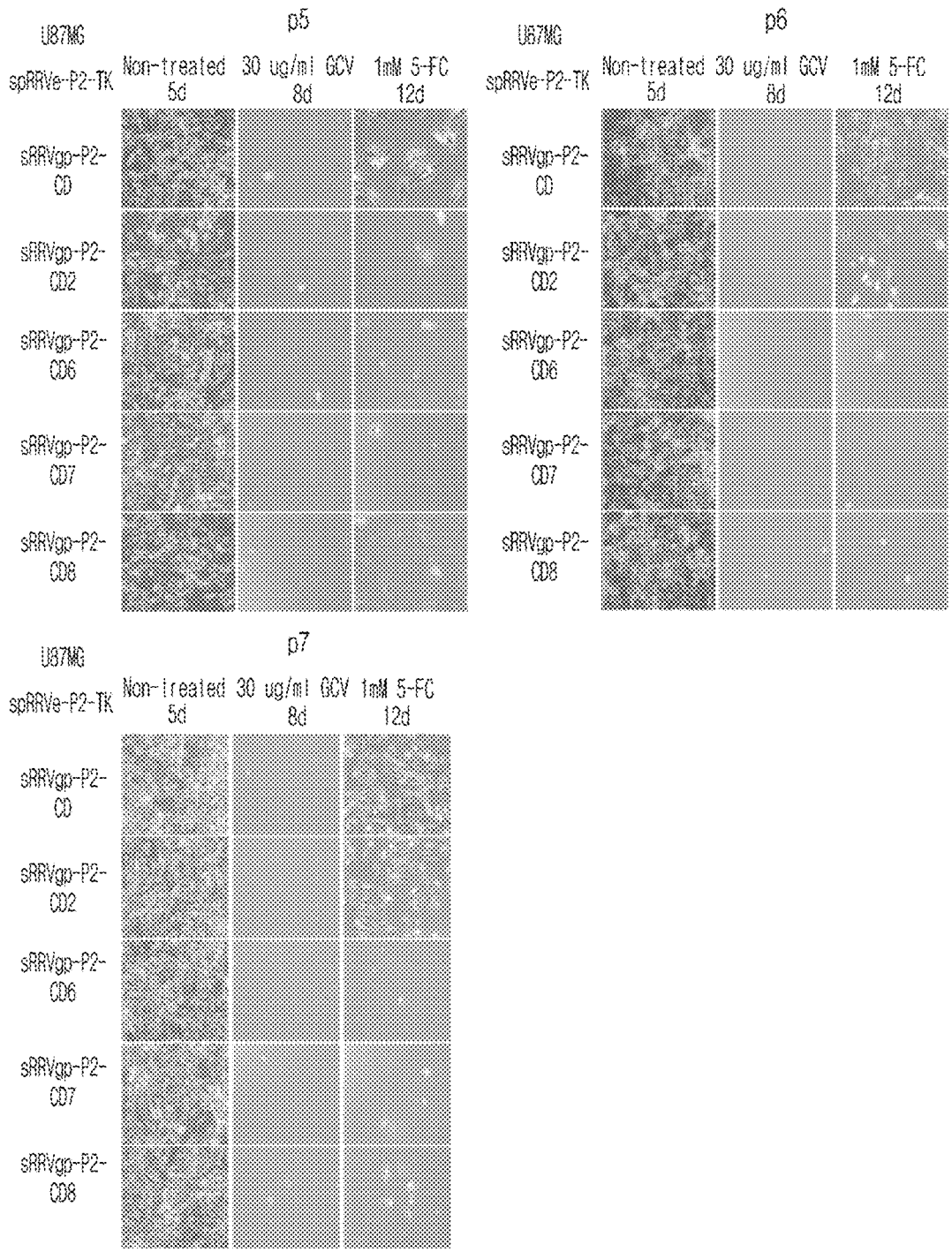
[Fig. 37c]

SEQUENCE LISTING

```
<160> NUMBER OF SEQ ID NOS: 45

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
cggaattcat ggcttcgtac cccggcca                                        28

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
gcgaattctc agtagcctcc cccatctc                                        28

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
cggcacgtga tggtattgct gcctggg                                         27

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
gcccacgtgt taaaggttac cttcgtt                                         27

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
agcaagctat tggccactg                                                  19
```

```
<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gactcagtca gcaagttaga g                                            21

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
caatcggagg actggcgccc cgagtga                                      27

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
gaaggtaacc tttaattcaa taacaggaaa g                                 31

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
ctttcctgtt attgaattaa aggttacctt c                                 31

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ggctagaatc cctatatgta                                              20

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
cgggatccat ggcttcgtac ccctgccat                                    29

<210> SEQ ID NO 12
<211> LENGTH: 29
<212> TYPE: DNA
<213> ORGANISM: Artificial Sequence
<220> FEATURE:
<223> OTHER INFORMATION: primer
```

<400> SEQUENCE: 12
cggtcgactc agttagcctc ccccatctc           29

<210> SEQ ID NO 13
<211> LENGTH: 9735
<212> TYPE: DNA
<213> ORGANISM: Artificial Sequence
<220> FEATURE:
<223> OTHER INFORMATION: vector

<400> SEQUENCE: 13

```
aacgccattt tgcaaggcat ggaaaaatac ataactgaga atagaaaagt tcagatcaag    60
gtcaggaaca gatggaacag ctgaatatgg gccaaacagg atatctgtgg taagcagttc   120
ctgccccggc tcaggccaa gaacagatgg aacagctgaa tatgggccaa acaggatatc   180
tgtggtaagc agttcctgcc ccggctcagg gccaagaaca gatggtcccc agatgcggtc   240
cagccctcag cagtttctag aaccatca gatgtttcca gggtgcccca aggacctgaa   300
atgaccctgt gccttatttg aactaaccaa tcagttcgct tctcgcttct gttcgcgcgc   360
ttatgctccc cgagctcaat aaaagagccc acaaccctc actcggggcg ccagtcctcc   420
gattgactga gtcgcccggg tacccgtgta tccaataaac cctcttgcag ttgcatccga   480
cttgtggtct cgctgttcct tgggagggtc tcctctgagt gattgactac ccgtcagcgg   540
gggtctttca tttgggggct cgtccggat cgggagaccc ctgccagg accaccgacc   600
caccaccggg aggtaagctg gccagcaact tatctgtgtc tgtccgattg tctagtgtct   660
atgactgatt ttatgcgcct gcgtcggtac tagttagcta actagctctg tatctggcgg   720
acccgtggtg gaactgacga gttcggaaca cccggccgca accctgggag acgtcccagg   780
gacttcgggg gccgttttttg tggcccgacc tgagtcctaa aatcccgatc gtttaggact   840
cttttggtgca ccccccttag aggagggata tgtggttctg gtaggagacg agaacctaaa   900
acagttcccg cctccgtctg aatttttgct ttcggtttgg gaccgaagcc gcgccgcgcg   960
tcttgtctgc tgcagcatcg ttctgtgttg tctctgtctg actgtgtttc tgtatttgtc  1020
tgaaaatatg ggccccgggct agcctgttac cactcccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagcttg gcttttgacc cccctccctg  1320
ggtcaagccc tttgtacacc ctaagcctcc gcctcctctt cctccatccg cccgtctct  1380
cccccttgaa cctcctcgtt cgaccccgcc tcgatcctcc ctttatccag ccctcactcc  1440
ttctctaggc gccccatat ggccatatga gatcttatat gggcacccc cgccccttgt  1500
aaacttccct gacccctgaca tgacaagagt tactaacagc ccctctctcc aagctcactt  1560
acaggctctc tacttagtcc agcacagaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
caccccacc gccctcaaag tagacggcat cgcagcttgg atacacgccg cccacaattc  1800
gatcatacct ggtgttgctg actccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
```

```
aataagaacc cccaccagcc catgaccctc acttggcagg tactgtccca aactggagac    2040
gttgtctggg atacaaaggc agtccagccc ccttggactt ggtggcccac acttaaacct    2100
gatgtatgtg ccttggcggc tagtcttgag tcctgggata tcccgggaac cgatgtctcg    2160
tcctctaaac gagtcagacc tccggactca gactatactg ccgcttataa gcaaatcacc    2220
tggggagcca tagggtgcag ctaccctcgg gctaggacta aatggcaag ctctaccttc     2280 tacgtatgtc cccgggatgg ccggacccctt cagaagcta aaggtgcgg ggggctagaa     2340 tccctatact gtaaagaatg ggattgtgag accacgggga ccggttattg gctatctaaa    2400
tcctcaaaag acctcataac tgtaaaatgg gaccaaaata gcgaatggac tcaaaaattt    2460
caacagtgtc accagaccgg ctggtgtaac ccccttaaaa tagatttcac agacaaagga    2520
aaattatcca aggactggat aacgggaaaa acctggggat taagattcta tgtgtctgga    2580
catccaggcg tacagttcac cattcgctta aaaatcacca acatgccagc tgtggcagta    2640
ggtcctgacc tcgtccttgt ggaacaagga cctcctagaa cgtccctcgc tctcccacct    2700
cctcttcccc caagggaagc gccaccgcca tctctcccg actctaactc cacagccctg     2760
gcgactagtg cacaaactcc cacggtgaga aaaacaattg ttaccctaaa cactccgcct    2820
cccaccacag gcgacagact ttttgatctt gtgcagggg ccttcctaac cttaaatgct     2880
accaacccag gggccactga gtcttgctgg cttttgtttgg ccatgggccc ccttattat    2940 gaagcaatag cctcatcagg agaggtcgcc tactccaccg accttgaccg gtgccgctgg    3000
gggacccaag gaaagctcac cctcactgag gtctcaggac acgggttgtg cataggaaag    3060
gtgcccttta cccatcagca tctctgcaat cagaccctat ccatcaattc ctccggagac    3120
catcagtatc tgctcccctc caaccatagc tggtgggctt gcagcactgg cctcacccct    3180
tgcctctcca cctcagtttt taatcagact agagatttct gtatccaggt ccagctgatt    3240
cctcgcatct attactatcc tgaagaagtt ttgttacagg cctatgacaa ttctcacccc    3300
aggactaaaa gagaggctgt ctcacttacc ctagctgttt tactggggtt gggaatcacg    3360
gcgggaatag gtactggttc aactgcctta attaaaggac ctatagacct ccagcaaggc    3420
ctgacaagcc tccagatcgc catagatgct gacctccggg ccctccaaga ctcagtcagc    3480
aagttagagg actcactgac ttccctgtcc gaggtagtgc tccaaaatag gagaggcctt    3540
gacttgctgt ttctaaaaga aggtggcctc tgtgcggccc taaaggaaga gtgctgtttt    3600
tacatagacc actcaggtgc agtacgggac tccatgaaaa aactcaaaga aaaactggat    3660
aaaagacagt tagagcgcca gaaaagccaa aactggtatg aaggatggtt caataactcc    3720
ccttggttca ctaccctgct atcaaccatc gctgggcccc tattactcct ccttctgttg    3780
ctcatcctcg ggccatgcat catcaataag ttagttcaat tcatcaatga taggataagt    3840
gcagttaaaa ttctggtcct tagacaaaaa tatcaggccc tagagaacga aggtaacctt    3900
taacacgtga aggctgccga cccccgggggt ggaccatcct ctagactgtg ctcgacgttt    3960
aaacgggcag agcgcacatc gcccacagtc cccgagaagt tgggggggagg ggtcggcaat    4020 tgatccggtg cctagagaag gtggcgcggg gtaaactggg aaagtgatgt cgtgtactgg    4080
ctccgccttt ttccccgaggg tgggggagaa ccgtatataa gtgcagtagt cgccgtgaac    4140 gttcttttc gcaacgggtt tgccgccaga acacagggat ccatggcttc gtaccctgc     4200 catcaacacg cgtctgcgtt cgaccaggct gcgcgttctc gcggccatag caaccgacgt    4260
acggcgttgc gccctcgccg gcagcaagaa gccacggaag tccgcctgga gcagaaaatg    4320
```

-continued

```
cccacgctac tgcgggttta tatagacggt cctcacggga tggggaaaac caccaccacg    4380
caactgctgg tggccctggg ttcgcgcgac gatatcgtct acgtacccga gccgatgact    4440
tactggcagg tgctgggggc ttccgagaca atcgcgaaca tctacaccac acaacaccgc    4500
ctcgaccagg gtgagatatc ggccggggac gcggcggtgg taatgacaag cgcccagata    4560
acaatgggca tgccttatgc cgtgaccgac gccgttctgg ctcctcatat cggggggggag   4620 gctgggagct cacatgcccc gccccggcc ctcaccctca tcttcgaccg ccatcccatc     4680
gccgccctcc tgtgctaccc ggccgcgcga taccttatgg gcagcatgac cccccaggcc   4740
gtgctggcgt tcgtggccct catcccgccg accttgcccg gcacaaacat cgtgttgggg   4800
gcccttccgg aggacagaca catcgaccgc ctggccaaac gccagcgccc cggcgagcgg   4860
cttgacctgg ctatgctggc cgcgattcgc cgcgtttacg ggctgcttgc caatacggtg   4920
cggtatctgc agggcggcgg gtcgtggcgg gaggattggg gacagctttc ggggacggcc   4980
gtgccgcccc agggtgccga gccccagagc aacgcgggcc cacgacccca tatcggggac   5040
acgttattta ccctgtttcg ggcccccgag ttgctggccc caacggcga cctgtacaac    5100 gtgtttgcct gggccttgga cgtcttggcc aaacgcctcc gtcccatgca cgtctttatc   5160
ctggattacg accaatcgcc cgccggctgc cgggacgccc tgctgcaact tacctccggg   5220
atggtccaga cccacgtcac cacccccggc tccataccga cgatctgcga cctggcgcgc   5280
acgtttgccc gggagatggg ggaggctaac tgagtcgaca tcgatggtac cagatccgat   5340
aaaataaaag gttttatttta gtctcctgaa aagggggga atgaaagacc ccacctgtag   5400
gtttggcaag ctagcttaag taacgccatt ttgcaaggca tggaaaaata cataactgag   5460
aatagagaag ttcagatcaa ggtcaggaac agatggaaca gctgaatatg gccaaacag    5520 gatatctgtg gtaagcagtt cctgcccccgg ctcagggcca agaacagatg gaacagctga   5580
atatgggcca acaggatat ctgtggtaag cagttcctgc cccggctcag ggccaagaac     5640
agatggtccc cagatgcggt ccagccctca gcagtttcta gagaaccatc agatgtttcc   5700
agggtgcccc aaggacctga atgaccctg tgccttattt gaactaacca atcagttcgc     5760
ttctcgcttc tgttcgcgcg cttctgctcc ccgagctcaa taaaagagcc cacaaccccct   5820 cactcggggc gccagtcctc cgattgactg agtcgcccgg gtaccgtgt atccaataaa    5880 ccctcttgca gttgcatccg acttgtggtc tcgctgttcc ttgggagggt ctcctctgag   5940
tgattgacta cccgtcagcg ggggtctttc acacatgcag catgtatcaa aattaatttg   6000
gttttttttc ttaagtattt acattaaatg gccatagtac ttaaagttac attggcttcc   6060
ttgaaataaa catggagtat tcagaatgtg tcataaatat ttctaatttt aagatagtat   6120
ctccattggc tttctacttt ttcttttatt ttttttttgtc ctctgtcttc catttgttgt   6180
tgttgttgtt tgtttgtttg tttgttggtt ggttggttaa tttttttttta aagatcctac   6240 actatagttc aagctagact attagctact ctgtaaccca gggtgacctt gaagtcatgg   6300
gtagcctgct gttttagcct tcccacatct aagattacag gtatgagcta tcattttggg   6360
tatatgattg attgattgat tgatgtgtgt gtgtgtgatt tgtttgtgt gtgtgactgt     6420 gaaaatgtgt gtatgggtgt gtgtgaatgt gtgtatgtat gtgtgtgtgt gagtgtgtgt   6480
gtgtgtgtgt gcatgtgtgt gtgtgtgact gtgtctatgt gtatgactgt gtgtgtgtgt   6540
gtgtgtgtgt gtgtgtgtgt gtgtgtgtgt gtgttgtgaa aaatatattct atggtagtga  6600 gagccaacgc tccggctcag gtgtcaggtt ggttttttgag acagagtctt tcacttagct   6660
tggaattcac tggccgtcgt tttacaacgt cgtgactggg aaaaccctgg cgttacccaa   6720
```

```
cttaatcgcc ttgcagcaca tcccccttc gccagctggc gtaatagcga agaggcccgc   6780
accgatcgcc cttcccaaca gttgcgcagc ctgaatggcg aatggcgcct gatgcggtat   6840
tttctcctta cgcatctgtg cggtatttca caccgcatat ggtgcactct cagtacaatc   6900
tgctctgatg ccgcatagtt aagccagccc cgacacccgc caacacccgc tgacgcgccc   6960
tgacgggctt gtctgctccc ggcatccgct tacagacaag ctgtgaccgt ctccgggagc   7020
tgcatgtgtc agaggttttc accgtcatca ccgaaacgcg cgagacgaaa gggcctcgtg   7080
atacgcctat ttttataggt taatgtcatg ataataatgg tttcttagac gtcaggtggc   7140
acttttcggg gaaatgtgcg cggaaccccct atttgtttat ttttctaaat acattcaaat   7200
atgtatccgc tcatgagaca ataaccctga taaatgcttc aataatattg aaaaaggaag   7260
agtatgagta ttcaacattt ccgtgtcgcc cttattccct tttttgcggc attttgcctt   7320
cctgttttg ctcacccaga aacgctggtg aaagtaaaag atgctgaaga tcagttgggt   7380
gcacgagtgg gttacatcga actggatctc aacagcggta agatccttga gagttttcgc   7440
cccgaagaac gttttccaat gatgagcact tttaaagttc tgctatgtgg cgcggtatta   7500
tcccgtattg acgccgggca agagcaactc ggtcgccgca tacactattc tcagaatgac   7560
ttggttgagt actcaccagt cacagaaaag catcttacgg atggcatgac agtaagagaa   7620
ttatgcagtg ctgccataac catgagtgat aacactgcgg ccaacttact tctgacaacg   7680
atcggaggac cgaaggagct aaccgctttt ttgcacaaca tgggggatca tgtaactcgc   7740
cttgatcgtt gggaaccgga gctgaatgaa gccataccaa acgacgagcg tgacaccacg   7800
atgcctgtag caatggcaac aacgttgcgc aaactattaa ctggcgaact acttactcta   7860
gcttcccggc aacaattaat agactggatg gaggcggata agttgcagg accacttctg   7920
cgctcggccc ttccggctgg ctggtttatt gctgataaat ctggagccgg tgagcgtggg   7980
tctcgcggta tcattgcagc actggggcca gatggtaagc cctcccgtat cgtagttatc   8040
tacacgacgg ggagtcaggc aactatggat gaacgaaata gacagatcgc tgagataggt   8100
gcctcactga ttaagcattg gtaactgtca gaccaagttt actcatatat actttagatt   8160
gatttaaaac ttcatttta atttaaaagg atctaggtga agatccttt tgataatctc   8220
atgaccaaaa tcccttaacg tgagtttcg ttccactgag cgtcagaccc cgtagaaaag   8280
atcaaaggat cttcttgaga tccttttttt ctgcgcgtaa tctgctgctt gcaaacaaaa   8340
aaaccaccgc taccagcggt ggtttgtttg ccggatcaag agctaccaac tcttttccg   8400
aaggtaactg gcttcagcag agcgcagata ccaaatactg ttcttctagt gtagccgtag   8460
ttaggccacc acttcaagaa ctctgtagca ccgcctacat acctcgctct gctaatcctg   8520
ttaccagtgg ctgctgccag tggcgataag tcgtgtctta ccgggttgga ctcaagacga   8580
tagttaccgg ataaggcgca gcggtcgggc tgaacggggg gttcgtgcac acagcccagc   8640
ttggagcgaa cgacctacac cgaactgaga tacctacagc gtgagctatg agaaagcgcc   8700
acgcttcccg aagggagaaa ggcggacagg tatccggtaa gcggcagggt cggaacagga   8760
gagcgcacga gggagcttcc agggggaaac gcctggtatc tttatagtcc tgtcgggttt   8820
cgccacctct gacttgagcg tcgatttttg tgatgctcgt caggggggcg gagcctatgg   8880
aaaaacgcca gcaacgcggc ctttttacgg ttcctggcct tttgctggcc ttttgctcac   8940
atgttctttc ctgcgttatc ccctgattct gtggataacc gtattaccgc ctttgagtga   9000
gctgataccg ctcgccgcag ccgaacgacc gagcgcagcg agtcagtgag cgaggaagcg   9060
```

-continued

| | |
|---|---|
| gaagagcgcc caatacgcaa accgcctctc cccgcgcgtt ggccgattca ttaatgcagc | 9120 |
| tggcacgaca ggtttcccga ctggaaagcg ggcagtgagc gcaacgcaat taatgtgagt | 9180 |
| tagctcactc attaggcacc ccaggcttta cactttatgc ttccggctcg tatgttgtgt | 9240 |
| ggaattgtga gcggataaca atttcacaca ggaaacagct atgaccatga ttacgccaag | 9300 |
| ctttgctcct aggagtttcc taatacttcc caaactcaaa tatataaagc atttgacttg | 9360 |
| ttctatgccc taggggcgg ggggaagcta agccagcttt ttttaacatt taaaatgtta | 9420 |
| attccatttt aaatgcacag atgttttat ttcataaggg tttcaatgtg catgaatgct | 9480 |
| gcaatattcc tgttaccaaa gctagtataa ataaaaatag ataaacgtgg aaattactta | 9540 |
| gagtttctgt cattaacgtt tccttcctca gttgacaaca taaatgcgct gctgagcaag | 9600 |
| ccagtttgca tctgtcagga tcaatttccc attatgccag tcatattaat tactagtcaa | 9660 |
| ttagttgatt tttattttg acatatacat gtgaatgaaa gaccccacct gtaggtttgg | 9720 |
| caagctagct taagt | 9735 |

<210> SEQ ID NO 14
<211> LENGTH: 10010
<212> TYPE: DNA
<213> ORGANISM: Artificial Sequence
<220> FEATURE:
<223> OTHER INFORMATION: vector

<400> SEQUENCE: 14

| | |
|---|---|
| catgtgagca aaaggccagc aaaaggccag gaaccgtaaa aaggccgcgt tgctggcgtt | 60 |
| tttccatagg ctccgccccc ctgacgagca tcacaaaaat cgacgctcaa gtcagaggtg | 120 |
| gcgaaacccg acaggactat aaagatacca ggcgtttccc cctggaagct ccctcgtgcg | 180 |
| ctctcctgtt ccgaccctgc cgcttaccgg atacctgtcc gcctttctcc cttcgggaag | 240 |
| cgtggcgctt tctcatagct cacgctgtag gtatctcagt tcggtgtagg tcgttcgctc | 300 |
| caagctgggc tgtgtgcacg aaccccccgt tcagcccgac cgctgcgcct tatccggtaa | 360 |
| ctatcgtctt gagtccaacc cggtaagaca cgacttatcg ccactggcag cagccactgg | 420 |
| taacaggatt agcagagcga ggtatgtagg cggtgctaca gagttcttga agtggtggcc | 480 |
| taactacggc tacactagaa ggacagtatt tggtatctgc gctctgctga agccagttac | 540 |
| cttcggaaaa agagttggta gctcttgatc cggcaaacaa accaccgctg gtagcggtgg | 600 |
| tttttttgtt tgcaagcagc agattacgcg cagaaaaaaa ggatctcaag aagatccttt | 660 |
| gatcttttct acggggtctg acgctcagtg gaacgaaaac tcacgttaag ggattttggt | 720 |
| catgagatta tcaaaaagga tcttcaccta gatcctttta aattaaaaat gaagttttaa | 780 |
| atcaatctaa agtatatatg agtaacctga tcaggactct tccttttcat gaacaataaa | 840 |
| actgtctgct tacataaaca gtaatacaag gggtgttatg agccatattc aacgggaaac | 900 |
| gtcttgctct aggccgcgat taaattccaa catggatgct gatttatatg ggtataaatg | 960 |
| ggctcgcgat aatgtcgggc aatcaggtgc gacaatctat cgattgtatg ggaagcccga | 1020 |
| tgcgccagag ttgtttctga acatggcaa aggtagcgtt gccaatgatg ttacagatga | 1080 |
| gatggtcaga ctaaactggc tgacggaatt tatgcctctt ccgaccatca agcatttat | 1140 |
| ccgtactcct gatgatgcat ggttactcac cactgcgatc cccgggaaaa cagcattcca | 1200 |
| ggtattagaa gaatatcctg attcaggtga aaatattgtt gatgcgctgg cagtgttcct | 1260 |
| gcgccggttg cattcgattc ctgtttgtaa ttgtcctttt aacagcgatc gcgtatttcg | 1320 |
| tctcgctcag gcgcaatcac gaatgaataa cggtttggtt gatgcgagtg attttgatga | 1380 |

```
cgagcgtaat ggctggcctg ttgaacaagt ctggaaagaa atgcataaac ttttgccatt    1440
ctcaccggat tcagtcgtca ctcatggtga tttctcactt gataacctta tttttgacga    1500
ggggaaatta ataggttgta ttgatgttgg acgagtcgga atcgcagacc gataccagga    1560
tcttgccatc ctatggaact gcctcggtga gttttctcct tcattacaga aacggctttt    1620
tcaaaaatat ggtattgata atcctgatat gaataaattg cagtttcatt tgatgctcga    1680
tgagtttttc taagaatttg tgaatgaaag accccacctg taggtttggc aagctagctt    1740
aagtaacgcc attttgcaag gcatggaaaa atacataact gagaatagaa aagttcagat    1800
caaggtcagg aacagatgga acagctgaat atgggccaaa caggatatct gtggtaagca    1860
gttcctgccc cggctcaggg ccaagaacag atggaacagc tgaatatggg ccaaacagga    1920
tatctgtggt aagcagttcc tgccccggct cagggccaag aacagatggt ccccagatgc    1980
ggtccagccc tcagcagttt ctagagaacc atcagatgtt tccagggtgc cccaaggacc    2040
tgaaatgacc ctgtgcctta tttgaactaa ccaatcagtt cgcttctcgc ttctgttcgc    2100
gcgcttatgc tccccgagct caataaaaga gcccacaacc cctcactcgg ggcgccagtc    2160
ctccgattga ctgagtcgcc cgggtacccg tgtatccaat aaaccctctt gcagttgcat    2220
ccgacttgtg gtctcgctgt tccttgggag ggtctcctct gagtgattga ctacccgtca    2280 gcggggtct ttcatttggg ggctcgtccg ggatcgggag accccctgccc agggaccacc    2340 gacccaccac cggaggtaa gctggccagc aacttatctg tgtctgtccg attgtctagt    2400
gtctatgact gattttatgc gcctgcgtcg gtactagtta gctaactagc tctgtatctg    2460
gcggacccgt ggtggaactg acgagttcgg aacacccggc cgcaaccctg ggagacgtcc    2520
cagggacttc gggggccgtt tttgtggccc gacctgagtc caaaaatccc gatcgttttg    2580
gactctttgg tgcacccccc ttagaggagg gatatgtggt tctggtagga gacgagaacc    2640
taaaacagtt cccgcctccg tctgaatttt tgctttcggt ttgggaccga agccgcgccg    2700
cgcgtcttgt ctgctgcagc atcgttctgt gttgtctctg tctgactgtg tttctgtatt    2760
tgtctgagaa tatgggccag actgttacca ctcccttaag tttgacctta ggtcactgga    2820
aagatgtcga gcggatcgct cacaaccagt cggtagatgt caagaagaga cgttgggtta    2880
ccttctgctc tgcagaatgg ccaaccttta acgtcggatg ccgcgagac ggcacctta    2940 accgagacct catcacccag gttaagatca aggtctttc acctggcccg catggacacc    3000
cagaccaggt ccctacatc gtgacctggg aagccttggc ttttgacccc cctccctggg    3060
tcaagccctt tgtacaccct aagcctccgc ctcctcttcc tccatccgcc ccgtctctcc    3120
cccttgaacc tcctcgttcg accccgcctc gatcctccct ttatccagcc ctcactcctt    3180
ctctaggcgc caaacctaaa cctcaagttc tttctgacag tggggggccg ctcatcgacc    3240
tacttacaga agacccccg ccttataggg acccaagacc accccttcc gacagggacg    3300 gaaatggtgg agaagcgacc cctgcgggag aggcaccgga cccctcccca atggcatctc    3360
gcctacgtgg gagacgggag cccccctgtgg ccgactccac tacctcgcag gcattccccc    3420
tccgcgcagg aggaaacgga cagcttcaat actggccgtt ctcctcttct gacctttaca    3480
actggaaaaa taataaccct tcttttttctg aagatccagg taaactgaca gctctgatcg    3540
agtctgttct catcacccat cagcccacct gggacgactg tcagcagctg ttggggactc    3600
tgctgaccga agaagaaaaa caacgggtgc tcttagaggc tagaaaggcg gtgcggggcg    3660
atgatgggcg ccccactcaa ctgcccaatg aagtcgatgc cgcttttccc ctcgagcgcc    3720
```

```
cagactggga ttacaccacc caggcaggta ggaaccacct agtccactat cgccagttgc    3780
tcctagcggg tctccaaaac gcgggcagaa gccccaccaa tttggccaag gtaaaaggaa    3840
taacacaagg gcccaatgag tctccctcgg ccttcctaga gagacttaag gaagcctatc    3900
gcaggtacac tccttatgac cctgaggacc cagggcaaga aactaatgtg tctatgtctt    3960
tcatttggca gtctgcccca gacattggga gaaagttaga gaggttagaa gatttaaaaa    4020
acaagacgct tggagatttg gttagagagg cagaaaagat ctttaataaa cgagaaaccc    4080
cggaagaaag agaggaacgt atcaggagag aaacagagga aaagaagaa cgccgtagga     4140
cagaggatga gcagaaagag aaagaaagag atcgtaggag acatagagag atgagcaagc    4200
tattggccac tgtcgttagt ggacagaaac aggatagaca gggaggagaa cgaaggaggt    4260
cccaactcga tcgcgaccag tgtgcctact gcaaagaaaa ggggcactgg gctaaagatt    4320
gtcccaagaa accacgagga cctcggggac caagacccca gacctccctc ctgaccctag    4380
atgactaggg aggtcagggt caggagcccc cccctgaacc caggataacc ctcaaagtcg    4440
gggggcaacc cgtcaccttc ctggtagata ctggggccca acactccgtg ctgacccaaa    4500
atcctggacc cctaagtgat aagtctgcct gggtccaagg ggctactgga ggaaagcggt    4560
atcgctggac cacggatcgc aaagtacatc tagctaccgg taaggtcacc cactcttcc    4620
tccatgtacc agactgtccc tatcctctgt taggaagaga tttgctgact aaactaaaag    4680
cccaaatcca ctttgaggga tcaggagctc aggttatggg accaatgggg cagccctgc    4740
aagtgttgac cctaaatata gaagatgagc atcggctaca tgagacctca aaagagccag    4800
atgtttctct agggtccaca tggctgtctg attttcctca ggcctgggcg gaaaccgggg    4860
gcatgggact ggcagttcgc caagctcctc tgatcatacc tctgaaagca acctctaccc    4920
ccgtgtccat aaaacaatac cccatgtcac aagaagccag actggggatc aagcccaca    4980
tacagagact gttggaccag ggaatactgg taccctgcca gtccccctgg aacacgcccc    5040
tgctacccgt taagaaaacca gggactaatg attataggcc tgtccaggat ctgagagaag    5100
tcaacaagcg ggtggaagac atccacccca ccgtgcccaa cccttacaac ctcttgagcg    5160
ggctcccacc gtcccaccag tggtacactg tgcttgattt aaaggatgcc ttttctgcc     5220
tgagactcca ccccaccagt cagcctctct tcgcctttga gtggagagat ccagagatgg    5280
gaatctcagg acaattgacc tggaccagac tcccacaggg tttcaaaaac agtcccaccc    5340
tgtttgatga ggcactgcac agagacctag cagacttccg gatccagcac ccagacttga    5400
tcctgctaca gtacgtggat gacttactgc tggccgccac ttctgagcta gactgccaac    5460
aaggtactcg ggccctgtta caaaccctag ggaacctcgg gtatcgggcc tcggccaaga    5520
aagcccaaat ttgccagaaa caggtcaagt atctgggta tcttctaaaa gagggtcaga    5580
gatggctgac tgaggccaga aaagagactg tgatggggca gcctactccg aagacccctc    5640
gacaactaag ggagttccta gggacggcag gcttctgtcg cctctggatc cctgggttg    5700
cagaaatggc agccccttg taccctctca ccaaaacggg gactctgttt aattggggcc    5760
cagaccaaca aaaggcctat caagaaatca agcaagctct tctaactgcc ccagccctgg    5820
ggttgccaga tttgactaag ccctttgaac tctttgtcga cgagaagcag ggctacgcca    5880
aaggtgtcct aacgcaaaaa ctgggacctt ggcgtcggcc ggtggcctac ctgtccaaaa    5940
agctagaccc agtagcagct gggtggcccc cttgcctacg gatggtagca gccattgccg    6000
tactgacaaa ggatgcaggc aagctaacca tgggacagcc actagtcatt ctggcccccc    6060
atgcagtaga ggcactagtc aaacaacccc ccgaccgctg gctttccaac gcccggatga    6120
```

```
ctcactatca ggccttgctt ttggacacgg accgggtcca gttcggaccg gtggtagccc    6180
tgaacccggc tacgctgctc ccactgcctg aggaagggct gcaacacaac tgccttgata    6240
tcctggccga agcccacgga acccgacccg acctaacgga ccagccgctc ccagacgccg    6300
accacacctg gtacacggat ggaagcagtc tcttacaaga gggacagcgt aaggcgggag    6360
ctgcggtgac caccgagacc gaggtaatct gggctaaagc cctgccagcc gggacatccg    6420
ctcagcgggc tgaactgata gcactcaccc aggccctaaa gatggcagaa ggtaagaagc    6480
taaatgttta tactgatagc cgttatgctt ttgctactgc ccatatccat ggagaaatat    6540
acagaaggcg tgggttgctc acatcagaag gcaaagagat caaaaataaa gacgagatct    6600
tggccctact aaaagccctc tttctgccca aaagacttag cataatccat tgtccaggac    6660
atcaaaaggg acacagcgcc gaggctagag gcaaccggat ggctgaccaa gcggcccgaa    6720
aggcagccat cacagagact ccagacacct ctaccctcct catagaaaat tcatcaccct    6780
acacctcaga acattttcat tacacagtga ctgatataaa ggacctaacc aagttggggg    6840
ccatttatga taaaacaaag aagtattggg tctaccaagg aaaacctgtg atgcctgacc    6900
agtttacttt tgaattatta gactttcttc atcagctgac tcacctcagc ttctcaaaaa    6960
tgaaggctct cctagagaga agccacagtc cctactacat gctgaaccgg atcgaacac    7020 tcaaaaatat cactgagacc tgcaaagctt gtgcacaagt caacgccagc aagtctgccg    7080
ttaaacaggg aactagggtc gcgggcatc ggcccggcac tcattgggag atcgatttca    7140
ccgagataaa gcccggattg tatggctata aatatcttct agtttttata gatacctttt    7200
ctggctggat agaagccttc ccaaccaaga agaaaccgc caaggtcgta accaagaagc    7260
tactagagga gatcttcccc aggttcggca tgcctcaggt attgggaact gacaatgggc    7320
ctgccttcgt ctccaaggtg agtcagacag tggccgatct gttggggatt gattggaaat    7380
tacattgtgc atacagaccc caaagctcag gccaggtaga agaatgaat agaaccatca    7440 aggagacttt aactaaatta acgcttgcaa ctggctctag agactgggtg ctcctactcc    7500
ccttagccct gtaccgagcc cgcaacacgc cgggccccca tggcctcacc ccatatgaga    7560
tcttatatgg ggcaccccg ccccttgtaa acttccctga ccctgacatg acaagagtta    7620
ctaacagccc ctctctccaa gctcacttac aggctctcta cttagtccag cacgaagtct    7680
ggagacctct ggcggcagcc taccaagaac aactggaccg accggtggta cctcacccttt    7740 accgagtcgg cgacacagtg tgggtccgcc gacaccagac taagaaccta gaacctcgct    7800
ggaaaggacc ttacacagtc ctgctgacca ccccaccgc cctcaaagta gacggcatcg    7860
cagcttggat acacgccgcc cacgtgaagg ctgccgaccc cggggtgga ccatcctcta    7920 gactgacatg gcgcgttcaa cgctctcaaa acccccttaaa aataaggtta acccgcgagg    7980 cccccctaatc cccttaattc ttctgatgct cagagggtc agtaaacgaa ttcgggcaga    8040
gcgcacatcg cccgcagtcc ccgagaagtt gggggaggg tcggcaatt gatccggtgc    8100 ctagagaagg tggcgcgggg taaactggga aagtgatgtc gtgtactggc tccgcctttt    8160
tcccgagggt gggggagaac cgtatataag tgcagtagtc gccgtgaacg ttctttttcg    8220
caacgggttt gccgccagaa cacaggcggc cgccgatggt tactgagggg atggccagta    8280
aatgggacca gaagggtatg gatattgcat acgaggaggc cgctttggga tacaaggagg    8340
ggggtgtccc tataggcggt tgcctgatca ataataaaga cggctctgtc ttgggaagag    8400
gacacaatat gcgctttcag aagggaagcg ccaccctgca tggagagatc tctaccctcg    8460
```

```
aaaattgcgg aaggctcgaa ggcaaagttt acaaagatac caccctctac acaacgctgt    8520
ccccctgtga tatgtgcacc ggtgccatta tcatgtatgg catcccacgc tgcgttgtag    8580
gagagaatgt aaacttcaaa tccaagggag agaagtatct ccagacccga gggcacgaag    8640
ttgtggtggt ggacgatgaa aggtgtaaga agatcatgaa gcagttcata gatgagcggc    8700
ctcaggactg gttcgaggat attggcgaat gagtttaaac gaattcataa aataaaagat    8760
tttatttagt ctccagaaaa aggggggaat gaaagacccc acctgtaggt ttggcaagct    8820
agcttaagta acgccatttt gcaaggcatg gaaaatacaa taactgagaa tagagaagtt    8880
cagatcaagg tcaggaacag atggaacagc tgaatatggg ccaaacagga tatctgtggt    8940
aagcagttcc tgccccggct cagggccaag aacagatgga acagctgaat atgggccaaa    9000
caggatatct gtggtaagca gttcctgccc cggctcaggg ccaagaacag atggtcccca    9060
gatgcggtcc agccctcagc agtttctaga gaaccatcag atgtttccag ggtgcccaa     9120 ggacctgaaa tgaccctgtg ccttatttga actaaccaat cagttcgctt ctcgcttctg    9180
ttcgcgcgct tctgctcccc gagctcaata aaagagccca caaccccctca ctcggggcgc   9240 cagtcctccg attgactgag tcgcccgggt accgtgtat ccaataaacc ctcttgcagt     9300
tgcatccgac ttgtggtctc gctgttcctt ggagggtct cctctgagtg attgactacc     9360
cgtcagcggg ggtctttcat tgttacttaa agttacattg gcttccttga aataaacatg    9420
gagtattcag aatgtgtcat aaatatttct aattttaaga tagtatctcc attggctttc    9480
tactttttct tttatttttt tttgtcctct gtcttccatt tgttgttgtt gttgtttgtt    9540
tgtttgtttg ttggttggtt ggttaatttt tttttaaaga tcctacacta tagttcaagc    9600
tagactatta gctactctgt aacccagggt gaccttgaag tcatgggtag cctgctgttt    9660
tagccttccc acatctaaga ttacaggtat gagctatcat ttttggtata ttgattgatt    9720
gattgattga tgtgtgtgtg tgtgattgtg tttgtgtgtg tgactgtgaa atgtgtgta     9780 tgggtgtgtg tgaatgtgtg tatgtatgtg tgtgtgtgag tgtgtgtgtg tgtgtgtgca    9840
tgtgtgtgtg tgtgactgtg tctatgtgta tgactgtgtg tgtgtgtgtg tgtgtgtgtg    9900
tgtgtgtgtg tgtgtgtgtg ttgtgaaaaa atattctatg gtagtgagag ccaacgctcc    9960
ggctcaggtg tcaggttggt ttttgagaca gagtctttca cttagcttgg                10010
```

<210> SEQ ID NO 15
<211> LENGTH: 1131
<212> TYPE: DNA
<213> ORGANISM: human herpesvirus 1

<400> SEQUENCE: 15

```
atggcttcgt accctgcca tcaacacgcg tctgcgttcg accaggctgc gcgttctcgc      60
ggccatagca accgacgtac ggcgttgcgc cctcgccggc agcaagaagc cacggaagtc     120
cgcctggagc agaaaatgcc cacgctactg cgggtttata tagacggtcc tcacgggatg     180
ggaaaaacca ccaccacgca actgctggtg ccctgggtt cgcgcgacga tatcgtctac      240
gtacccgagc cgatgactta ctggcaggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccggccct caccctcatc      480 ttcgaccgcc atcccatcgc cgccctcctg tgctacccgg ccgcgcgata ccttatgggc    540
agcatgaccc cccaggccgt gctggcgttc gtggccctca tccgccgac cttgcccggc    600
```

```
acaaacatcg tgttgggggc ccttccggag acagacaca tcgaccgcct ggccaaacgc      660
cagcgccccg gcgagcggct tgacctggct atgctggccg cgattcgccg cgtttacggg      720
ctgcttgcca atacggtgcg gtatctgcag ggcggcgggt cgtggcggga ggattgggga      780
cagctttcgg ggacggccgt gccgcccag ggtgccgagc cccagagcaa cgcgggccca       840
cgaccccata tcggggacac gttatttacc ctgtttcggg ccccgagtt gctggccccc       900 aacggcgacc tgtacaacgt gtttgcctgg gccttggacg tcttggccaa acgcctccgt      960
cccatgcacg tctttatcct ggattacgac caatcgcccg ccggctgccg ggacgccctg     1020
ctgcaactta cctccgggat ggtccagacc cacgtcacca cccccggctc ataccgacg      1080 atctgcgacc tggcgcgcac gtttgcccgg gagatggggg aggctaactg a              1131
```

<210> SEQ ID NO 16
<211> LENGTH: 406
<212> TYPE: DNA
<213> ORGANISM: Saccharomyces cerevisiae

<400> SEQUENCE: 16

```
atggtgacag ggggaatggc aagcaagtgg gatcagaagg gtatggacat tgcctatgag       60
gaggcggcct taggttacaa agagggtggt gttcctattg gcggatgtct tatcaataac      120
aaagacggaa gtgttctcgg tcgtggtcac aacatgagat ttcaaaaggg atccgccaca      180
ctacatggtg agatctccac tttggaaaac tgtgggagat tagagggcaa agtgtacaaa      240
gataccactt tgtatacgac gctgtctcca tgcgacatgt gtacaggtgc catcatcatg      300
tatggtattc cacgctgtgt tgtcggtgag aacgttaatt tcaaaagtaa gggcgagaaa      360
tatttacaaa ctagaggtca cgaggttgtt gttgttgacg atgaga                   406
```

<210> SEQ ID NO 17
<211> LENGTH: 477
<212> TYPE: DNA
<213> ORGANISM: Artificial Sequence
<220> FEATURE:
<223> OTHER INFORMATION: CD2

<400> SEQUENCE: 17

```
atggtgaccg gcggcatggc ctccaagtgg gatcaaaagg gcatggatat cgcttacgag       60
gaggccctgc tgggctacaa ggagggcggc gtgcctatcg gcggctgtct gatcaacaac      120
aaggacggca gtgtgctggg caggggccac aacatgaggt tccagaaggg ctccgccacc      180
ctgcacggcg agatctccac cctggagaac tgtggcaggc tggagggcaa ggtgtacaag      240
gacaccaccc tgtacaccac cctgtcccct tgtgacatgt gtaccggcgc tatcatcatg      300
tacggcatcc ctaggtgtgt gatcggcgag aacgtgaact tcaagtccaa gggcgagaag      360
tacctgcaaa ccagggggcca cgaggtggtg gttgttgacg atgagaggtg taagaagctg      420
atgaagcagt tcatcgacga gaggcctcag gactggttcg aggatatcgg cgagtaa        477
```

<210> SEQ ID NO 18
<211> LENGTH: 477
<212> TYPE: DNA
<213> ORGANISM: Artificial Sequence
<220> FEATURE:
<223> OTHER INFORMATION: CD3 gene

<400> SEQUENCE: 18

```
atggtgaccg gcggcatggc ctccaagtgg gaccaaaagg gcatggatat cgcttacgag       60
```

```
gaggccctgc tgggctacaa ggagggcggc gtgcccatcg gcggctgcct gatcaacaac    120
aaggacggca gcgtgctggg caggggccac aacatgaggt tccagaaggg ctccgccacc    180
ctgcacggcg agatctccac cctggagaac tgcggcaggc tggagggcaa ggtgtacaag    240
gacaccaccc tgtacaccac cctgtcccct tgtgacatgt gcaccggcgc tatcatcatg    300
tacggcatcc ctaggtgcgt gatcggcgag aacgtgaact tcaagtccaa gggcgagaag    360
tacctgcaga ccaggggcca cgaggtggtg gtggtggacg acgagaggtg caagaagctg    420
atgaagcagt tcatcgacga gaggccccag gactggttcg aggacatcgg cgagtaa       477

<210> SEQ ID NO 19
<211> LENGTH: 477
<212> TYPE: DNA
<213> ORGANISM: Artificial Sequence
<220> FEATURE:
<223> OTHER INFORMATION: CD4 gene

<400> SEQUENCE: 19
atggtgacag ggggaatggc aagcaagtgg gatcagaagg gtatggacat tgcctatgag     60
gaggcggcct taggttacaa agagggtggt gttcctattg gcggatgtct tatcaataac    120
aaagacggaa gtgttctcgg tcgtggtcac aacatgagat ttcaaaaggg atccgccaca    180
ctacatggtg agatctccac tttggagaac tgcggcaggc tggaaggcaa ggtgtacaaa    240
gataccactc tgtacaccac cctgtctcca tgcgacatgt gtacaggtgc catcatcatg    300
tatggtattc cacgctgtgt tgtcggtgag aacgttaatt tcaaaagtaa gggcgagaaa    360
tacttgcaaa ccaggggcca cgaggtggtg gttgttgacg atgagaggtg taaaaagatc    420
atgaaacaat tatcgatga agacctcag gactggttcg aggacatcgg cgagtaa        477

<210> SEQ ID NO 20
<211> LENGTH: 477
<212> TYPE: DNA
<213> ORGANISM: Artificial Sequence
<220> FEATURE:
<223> OTHER INFORMATION: CD5 gene

<400> SEQUENCE: 20
atggtgactg gcggcatggc atccaagtgg gaccagaagg ggatggacat agcatatgaa     60
gaggccgcgt tgggatataa ggagggcggt gtaccaatcg ggggctgcct cattaacaat    120
aaagatggct ccgttctggg tcgcggccac aacatgaggt ttcagaaggg cagtgcgacg    180
ctccacggag aaatcagcac actggaaaat tgtgggcgat tggaggggaa agtgtataag    240
gatacaactc tctacaccac tctcagcccc tgcgatatgt gcacaggcgc aatcataatg    300
tacggcattc cccgatgcgt ggtgggggag aacgtgaact tcaagagcaa aggagagaaa    360
tatcttcaga ccagaggaca cgaagtagtg gtggtggatg atgaacgctg caagaaaatc    420
atgaaacagt ttatagatga acgaccacaa gactggttcg aggatatcgg cgaatag      477

<210> SEQ ID NO 21
<211> LENGTH: 477
<212> TYPE: DNA
<213> ORGANISM: Artificial Sequence
<220> FEATURE:
<223> OTHER INFORMATION: CD6 gene

<400> SEQUENCE: 21
atggttactg gagggatggc cagtaaatgg gaccagaagg gtatggatat tgcatacgag     60
gaggccgctt tgggatacaa ggaggggggt gtccctatag gcggttgcct gatcaataat    120
```

```
aaagacggct ctgtcttggg aagaggacac aatatgcgct ttcagaaggg aagcgccacc    180
ctgcatggag agatctctac cctcgaaaat tgcggaaggc tcgaaggcaa agtttacaaa    240
gataccaccc tctacacaac gctgtccccc tgtgatatgt gcaccggtgc cattatcatg    300
tatggcatcc cacgctgcgt tgtaggagag aatgtaaact tcaaatccaa gggagagaag    360
tatctccaga cccgagggca cgaagttgtg gtggtggacg atgaaaggtg taagaagatc    420
atgaagcagt tcatagatga gcggcctcag gactggttcg aggatattgg cgaatga      477

<210> SEQ ID NO 22
<211> LENGTH: 477
<212> TYPE: DNA
<213> ORGANISM: Artificial Sequence
<220> FEATURE:
<223> OTHER INFORMATION: CD7 gene

<400> SEQUENCE: 22
atggtaactg gtggcatggc ctcaaagtgg gatcagaaag gaatggacat cgcttacgag     60
gaggccgcac tgggctataa ggagggcggc gtccctatag gcggttgcct gattaacaat    120
aaagacggct cagtgctggg aaggggcac aacatgagat tcagaaagg cagcgcaact    180 ctgcacggcg aaatctccac tctggagaac tgcgggcggc tggagggaaa ggtttataaa    240
gatactacct tgtatacaac tctgtccccc tgcgatatgt gcaccggcgc catcataatg    300
tacggaatac ccaggtgcgt ggtgggagag aacgtgaatt ttaagtcaaa aggtgagaag    360
tacctgcaga ctcgcggcca tgaggtggtt gttgttgacg atgaaaggtg caagaagatt    420
atgaagcagt tcattgatga agaccccag gactggtttg aggatatcgg agagtag       477

<210> SEQ ID NO 23
<211> LENGTH: 477
<212> TYPE: DNA
<213> ORGANISM: Artificial Sequence
<220> FEATURE:
<223> OTHER INFORMATION: CD8 gene

<400> SEQUENCE: 23
atggttactg ggggaatggc atctaagtgg gatcagaaag gtatggacat cgcttatgaa     60
gaggctgctc tcggctacaa agagggtgga gtgcctatcg agggtgcct gatcaacaac    120 aaggacggca gtgtgctggg gaggggccac aatatgaggt tccaaaaagg ctccgccact    180
ctccacgggg aaattagtac cctcgagaat tgcggacgat tggaagggaa ggtgtacaag    240
gatacaacac tgtacaccac cctgtcaccc tgtgatatgt gcacaggcgc cattatcatg    300
tacggaatcc ctagatgtgt cgtggggag aatgtaaact tcaaaagtaa ggggagaaa    360 tatctccaga cccgggggca cgaagtcgtc gttgtggacg atgaacggtg taagaagatc    420
atgaagcagt ttatcgatga gaggccccag gactggttcg aagacatcgg gaataa       477

<210> SEQ ID NO 24
<211> LENGTH: 477
<212> TYPE: DNA
<213> ORGANISM: Artificial Sequence
<220> FEATURE:
<223> OTHER INFORMATION: CD9 gene

<400> SEQUENCE: 24
atggttacag ggggaatggc aagtaaatgg gatcaaaaag ggatggatat agcctatgag     60
gaagcggcgc tgggctataa agagggaggg gtgccgatag gtggctgtct tattaataac    120
```

```
aaagacggga gtgtgttggg cagaggccac aatatgcgat ttcaaaaagg gtccgcgaca    180
ttgcacggag agatcagcac cctggagaat tgcggaaggt tggagggaaa agtgtataag    240
gacaccaccc tctataccac actgtctcca tgtgatatgt gtaccggtgc catcataatg    300
tacgggattc ctcgctgcgt agtgggagag aatgttaact ttaaaagcaa gggagagaag    360
tatttgcaaa cccgggccca cgaagtggtg gtggtggacg acgagcgatg taagaaaatc    420
atgaagcaat ttatcgatga gcggcctcaa gattggttcg aagatatcgg cgagtga      477
```

<210> SEQ ID NO 25
<211> LENGTH: 477
<212> TYPE: DNA
<213> ORGANISM: Artificial Sequence
<220> FEATURE:
<223> OTHER INFORMATION: CD10 gene

<400> SEQUENCE: 25

```
atggtaaccg gaggtatggc atccaagtgg gaccaaaaag gaatggacat agcatatgaa     60
gaagcagccc tgggctacaa ggaggagggg gttccgattg gcggttgtct tataaataat    120
aaagacggta gtgttcttgg caggggtcac aacatgagat tccaaaaggg gagtgctaca    180
cttcacggcg aaataagcac cttggaaaac tgtggtagac ttgagggaaa agtgtacaag    240
gacacgaccc tttatacgac gctgtcccct tgtgatatgt gcaccggcgc tatcatcatg    300
tatggaatac cacgatgcgt agtggagag aatgttaatt tcaagagtaa gggcgagaag    360
taccttcaga ccagggggca cgaggtagta gtagttgacg atgagcgatg caagaagatt    420
atgaaacaat tcattgacga gaggccgcag gattggtttg aagacatcgg cgaatag       477
```

<210> SEQ ID NO 26
<211> LENGTH: 477
<212> TYPE: DNA
<213> ORGANISM: Artificial Sequence
<220> FEATURE:
<223> OTHER INFORMATION: CD11 gene

<400> SEQUENCE: 26

```
atggtgacag ggggtatggc aagcaaatgg gatcagaagg gtatggacat cgcatacgag     60
gaggcggcct tgggctataa ggaaggcggc gtacctatag gggggtgcct tattaacaat    120
aaggacggga cgtcctgggg cagaggtcac aacatgaggt tccaaaaggg ttcagcaacc    180
ctgcatggcg aaataagcac ccttgagaat tgtgggaggt tggagggtaa ggtgtacaag    240
gataccacgc tttataccac cttgagtcct tgcgacatgt gcacaggcgc tataatcatg    300
tatggaatac cgcgctgtgt tgtaggagaa aatgtaaact tcaagagtaa aggagaaaaa    360
tacttgcaaa cgcggggaca cgaagtggta gttgtcgatg atgagcggtg caaaaaaatc    420
atgaagcagt tcattgacga acgcccccaa gactggttcg aagacattgg ggagtag       477
```

<210> SEQ ID NO 27
<211> LENGTH: 477
<212> TYPE: DNA
<213> ORGANISM: Artificial Sequence
<220> FEATURE:
<223> OTHER INFORMATION: CD12 gene

<400> SEQUENCE: 27

```
atggtaacgg gtgggatggc tagcaagtgg gaccagaaag gcatggatat agcgtatgaa     60
gaagcggcgt tggggttacaa agagggcggc gttcccatcg gtggctgcct tatcaataat    120
aaagacggct ccgtccttgg ccggggacac aatatgcgct tccaaaaggg cagcgccaca    180
```

```
cttcacggtg agatctccac gctggagaat tgtgggcgac ttgaggggaa agtctacaag      240
gacacaactt tgtacacaac acttagcccg tgcgatatgt gtacgggagc cataatcatg      300
tacggcatcc cgcgctgcgt ggtaggagag aacgtaaatt ttaagtcaaa aggagaaaaa      360
tatcttcaga ccaggggcca cgaggtggtt gtcgtgacg acgagagatg taaaaagatc       420
atgaaacagt ttattgatga aagaccacag gattggtttg aggacatcgg tgagtag        477
```

<210> SEQ ID NO 28
<211> LENGTH: 477
<212> TYPE: DNA
<213> ORGANISM: Artificial Sequence
<220> FEATURE:
<223> OTHER INFORMATION: CD13 gene

<400> SEQUENCE: 28

```
atggttacag gaggtatggc ttcaaagtgg atcaaaaag ggatggacat cgcctatgaa       60
gaagcagcgt tgggatacaa agaaggggggg gttcccatag gaggttgcct tatcaacaat     120
aaagatggaa gcgttcttgg gcgagggcac aatatgagat ttcaaaaagg ttcagccact     180
ctccatggag aaatttcaac ctctcgaaaac tgtggtcgcc ttgagggcaa ggtttataag     240
gataccaccc tctacactac cctgtcaccc tgcgacatgt gtacaggtgc aattataatg      300
tacggaatcc ctcggtgtgt ggtggggggag aacgtgaatt ttaagtccaa aggtgaaaaa    360
tatctccaaa ctcgcgggca tgaagtcgtc gttgttgatg atgagaggtg taaaaagatt     420
atgaaacaat tcatagacga gaggccacag gattggtttg aggacatagg ggagtag       477
```

<210> SEQ ID NO 29
<211> LENGTH: 477
<212> TYPE: DNA
<213> ORGANISM: Artificial Sequence
<220> FEATURE:
<223> OTHER INFORMATION: CD14 gene

<400> SEQUENCE: 29

```
atggtgactg ggggtatggc ttccaaatgg atcagaaag gaatggatat agcatacgaa       60
gaagcagctc tcgggtacaa agagggtgga gtacccattg ggggatgcct catcaacaac     120
aaggatggga gtgtccttgg gcgaggtcac aatatgcgat tccagaaggg gagcgcgacg     180
ctccacgggg agataagtac gctggagaac tgcggggaggc ttgaaggcaa ggtctacaaa    240
gataccacac tctacacgac cctcagcccct tgcgacatgt gtacgggtgc gatcatcatg    300
tatggaatac cgcgatgcgt agtaggagag aacgtgaact tcaagtccaa aggcgaaaag    360
tatctccaga cgcgcggcca cgaagtggta gtggtagacg acgaaaggtg caagaagata     420
atgaagcagt ttatcgacga gaggcctcag gactggttcg aggatattgg cgagtag       477
```

<210> SEQ ID NO 30
<211> LENGTH: 477
<212> TYPE: DNA
<213> ORGANISM: Artificial Sequence
<220> FEATURE:
<223> OTHER INFORMATION: CD15 gene

<400> SEQUENCE: 30

```
atggttactg gcggcatggc ttctaagtgg atcagaaggg gcatggatat agcctatgaa      60
gaagcagcac tgggatacaa agaggggaggg gtaccaattg ggggatgtct gattaataac    120
aaagacggaa gtgtactcgg tcgcgggcat aatatgagat tccaaaaagg ctctgcaacg    180
```

```
ttgcacggcg aaatcagcac gctcgaaaat tgcgggaggc tggagggaaa ggtttacaag      240
gataccactc tctataccac actgtcacca tgtgatatgt gtacggggc tataataatg       300 tatggaatcc cccgctgcgt cgtgggcgaa aacgtcaact ttaagtctaa gggggaaaag      360
tatttgcaaa cgcgcggtca tgaggtcgtt gtagtcgatg acgagagatg caaaaaaata      420
atgaagcagt ttattgacga gagacctcag gactggttcg aagacatcgg ggagtag        477
```

<210> SEQ ID NO 31
<211> LENGTH: 477
<212> TYPE: DNA
<213> ORGANISM: Artificial Sequence
<220> FEATURE:
<223> OTHER INFORMATION: CD16 gene

<400> SEQUENCE: 31

```
atggtgacag gaggaatggc cagcaagtgg gatcagaagg gaatggatat tgcctacgag       60
gaggccgccc tgggctacaa ggagggggc gtgccaattg cggatgtct gattaacaac       120 aaggatggga gcgtgctggg aagaggacac aacatgagat tcagaaggg aagcgcaacc      180 ttgcacggag aaattagcac ccttgagaac tgcgggcggc ttgaaggcaa ggtctataaa      240
gacactacac tttatactac cttgtctcca tgtgatatgt gtacaggcgc cattattatg      300
tacggaattc ctagatgcgt cgtgggagag aacgtgaact ttaagagcaa gggagagaag      360
tacctgcaga caagaggaca cgaggtggtg gtggtgatg atgagagatg taagaagatc      420
atgaagcagt tcatcgatga gaggcccag gattggtttg aggacatcgg cgagtga        477
```

<210> SEQ ID NO 32
<211> LENGTH: 1617
<212> TYPE: DNA
<213> ORGANISM: Murine leukemia virus

<400> SEQUENCE: 32

```
atgggccaga ctgttaccac tcccttaagt ttgaccttag gtcactggaa agatgtcgag       60
cggatcgctc acaaccagtc ggtagatgtc aagaagagac gttgggttac cttctgctct      120
gcagaatggc caacctttaa cgtcggatgg ccgcgagacg gcacctttaa ccagacctc       180 atcacccagg ttaagatcaa ggtcttttca cctggcccgc atggacaccc agaccaggtc      240
ccctacatcg tgacctggga agccttggct tttgaccccc ctccctgggt caagccttt       300 gtacaccta gcctccgcc tcctcttcct ccatccgccc cgtctctccc ccttgaacct      360
cctcgttcga ccccgcctcg atcctccctt tatccagccc tcactccttc tctaggcgcc      420
aaacctaaac ctcaagttct ttctgacagt gggggccgc tcatcgacct acttacagaa      480
gaccccccgc ttataggga cccaagacca cccccttccg acaggacgg aaatggtgga      540 gaagcgaccc ctgcgggaga ggcaccggac ccctccccaa tggcatctcg cctacgtggg      600
agacgggagc ccctgtggcc cgactccact acctcgcagg cattcccct ccgcgcagga      660 ggaaacggac agcttcaata ctggccgttc tcctcttctg accttacaa ctggaaaaat      720 aataaccctt cttttttctga agatccaggt aaactgacag ctctgatcga gtctgttctc      780
atcacccatc agcccacctg ggacgactgt cagcagctgt gggactct gctgaccgga      840 gaagaaaaac aacgggtgct cttagaggct agaaaggcgg tgcgggcga tgatggcgc      900 cccactcaac tgcccaatga agtcgatgcc gcttttcccc tcgagcgccc agactgggat      960
tacaccaccc aggcaggtag gaaccaccta gtccactatc gccagttgct cctagcgggt     1020
ctccaaaacg cgggcagaag cccccaccaat ttggccaagg taaaggaat aacacaaggg     1080
```

```
cccaatgagt ctccctcggc cttcctagag agacttaagg aagcctatcg caggtacact    1140
ccttatgacc ctgaggaccc agggcaagaa actaatgtgt ctatgtcttt catttggcag    1200
tctgccccag acattgggag aaagttagag aggttagaag atttaaaaaa caagacgctt    1260
ggagatttgg ttagagaggc agaaaagatc tttaataaac gagaaccccc ggaagaaaga    1320
gaggaacgta tcaggagaga aacagaggaa aaagaagaac gccgtaggac agaggatgag    1380
cagaaagaga aagaaagaga tcgtaggaga catagagaga tgagcaagct attgccact    1440 gtcgttagtg gacagaaaca ggatagacag ggaggagaac gaaggaggtc ccaactcgat    1500
cgcgaccagt gtgcctactg caaagaaaag gggcactggg ctaaagattg tcccaagaaa    1560
ccacgaggac ctcggggacc aagaccccag acctccctcc tgaccctaga tgactag       1617
```

```
<210> SEQ ID NO 33
<211> LENGTH: 3608
<212> TYPE: DNA
<213> ORGANISM: Murine leukemia virus

<400> SEQUENCE: 33
atgactaggg aggtcagggt caggagcccc cccctgaacc caggataaacc ctcaaagtcg      60 gggggcaacc cgtcaccttc ctggtagata ctggggccca acactccgtg ctgacccaaa     120
atcctggacc cctaagtgat aagtctgcct gggtccaagg ggctactgga ggaaagcggt     180
atcgctggac cacggatcgc aaagtacatc tagctaccgg taaggtcacc cactctttcc     240
tccatgtacc agactgtccc tatcctctgt taggaagaga tttgctgact aaactaaaag     300
cccaaatcca ctttgaggga tcaggagctc aggttatggg accaatgggg cagcccctgc     360
aagtgttgac cctaaatata gaagatgagc atcggctaca tgagacctca aaagagccag     420
atgtttctct agggtccaca tggctgtctg attttcctca ggcctgggcg gaaaccgggg     480
gcatgggact ggcagttcgc caagctcctc tgatcatacc tctgaaagca acctctaccc     540
ccgtgtccat aaaacaatac cccatgtcac aagaagccag actggggatc aagccccaca     600
tacagagact gttggaccag ggaatactgg taccctgcca gtcccctgg aacacgcccc     660 tgctacccgt taagaaacca gggactaatg attataggcc tgtccaggat ctgagagaag     720
tcaacaagcg ggtggaagac atccacccca ccgtgcccaa cccttacaac ctcttgagcg     780
ggctcccacc gtcccaccag tggtacactg tgcttgattt aaaggatgcc ttttctgcc     840 tgagactcca ccccaccagt cagcctctct tcgcctttga gtggagagat ccagagatgg     900
gaatctcagg acaattgacc tggaccagac tcccacaggg tttcaaaaac agtcccaccc     960
tgtttgatga ggcactgcac agagacctag cagacttccg gatccagcac ccagacttga    1020
tcctgctaca gtacgtggat gacttactgc tggccgccac ttctgagcta gactgccaac    1080
aaggtactcg ggccctgtta caaaccctag gaaacctcgg tatcgggcc tcggccaaga    1140 aagcccaaat tgccagaaa caggtcaagt atctggggta tcttctaaaa gagggtcaga    1200
gatggctgac tgaggccaga aaagagactg tgatgggggca gcctactccg aagacccctc    1260
gacaactaag ggagttccta gggacggcag gcttctgtcg cctctggatc cctgggtttg    1320
cagaaatggc agccccttg taccctctca ccaaaacggg gactctgttt aattggggcc    1380
cagaccaaca aaaggcctat caagaaatca gcaagctct tctaactgcc ccagccctgg    1440
ggttgccaga tttgactaag ccccttttgaac tctttgtcga cgagaagcag ggctacgcca    1500
aaggtgtcct aacgcaaaaa ctgggacctt ggcgtcggcc ggtggcctac ctgtccaaaa    1560
```

```
agctagaccc agtagcagct gggtggcccc cttgcctacg gatggtagca gccattgccg    1620
tactgacaaa ggatgcaggc aagctaacca tgggacagcc actagtcatt ctggcccccc    1680
atgcagtaga ggcactagtc aaacaacccc ccgaccgctg gctttccaac gcccggatga    1740
ctcactatca ggccttgctt ttggacacgg accgggtcca gttcggaccg gtggtagccc    1800
tgaacccggc tacgctgctc ccactgcctg aggaagggct gcaacacaac tgccttgata    1860
tcctggccga agcccacgga acccgacccg acctaacgga ccagccgctc ccagacgccg    1920
accacacctg gtacacggat ggaagcagtc tcttacaaga gggacagcgt aaggcgggag    1980
ctgcggtgac caccgagacc gaggtaatct gggctaaagc cctgccagcc gggacatccg    2040
ctcagcgggc tgaactgata gcactcaccc aggccctaaa gatggcagaa ggtaagaagc    2100
taaatgttta tactgatagc cgttatgctt ttgctactgc ccatatccat ggagaaatat    2160
acagaaggcg tgggttgctc acatcagaag gcaaagagat caaaaataaa gacgagatct    2220
tggccctact aaaagccctc tttctgccca aagacttag cataatccat tgtccaggac     2280
atcaaaaggg acacagcgcc gaggctagag gcaaccggat ggctgaccaa gcggcccgaa    2340
aggcagccat cacagagact ccagacacct ctaccctcct catagaaaat tcatcaccct    2400
acacctcaga acattttcat tacacagtga ctgatataaa ggacctaacc aagttggggg    2460
ccatttatga taaacaaag aagtattggg tctaccaagg aaaacctgtg atgcctgacc      2520
agtttacttt tgaattatta gactttcttc atcagctgac tcacctcagc ttctcaaaaa    2580
tgaaggctct cctagagaga agccacagtc cctactacat gctgaaccgg atcgaacac     2640
tcaaaaatat cactgagacc tgcaaagctt gtgcacaagt caacgccagc aagtctgccg    2700
ttaaacaggg aactagggtc cgcgggcatc ggcccggcac tcattgggag atcgatttca    2760
ccgagataaa gcccggattg tatggctata aatatcttct agtttttata gatacctttt    2820
ctggctggat agaagccttc ccaaccaaga agaaaccgc caaggtcgta accaagaagc     2880
tactagagga gatcttcccc aggttcggca tgcctcaggt attgggaact gacaatgggc    2940
ctgccttcgt ctccaaggtg agtcagacag tggccgatct gttggggatt gattggaaat    3000
tacattgtgc atacagaccc caaagctcag gccaggtaga agaatgaat agaaccatca     3060
aggagacttt aactaaatta acgcttgcaa ctggctctag agactgggtg ctcctactcc    3120
ccttagccct gtaccgagcc cgcaacacgc cgggcccca tggcctcacc ccatatgaga     3180
tcttatatgg ggcaccccg ccccttgtaa acttccctga cctgacatg acaagagtta      3240
ctaacagccc ctctctccaa gctcacttac aggctctcta cttagtccag cacgaagtct    3300
ggagacctct ggcggcagcc taccaagaac aactggaccg accggtggta cctcacccttt   3360
accgagtcgg cgacacagtg tgggtccgcc gacaccagac taagaaccta gaacctcgct    3420
ggaaaggacc ttacacagtc ctgctgacca cccccaccgc cctcaaagta gacggcatcg    3480
cagcttggat acacgccgcc cacgtgaagg ctgccgaccc cgggggtgga ccatcctcta    3540
gactgacatg gcgcgttcaa cgctctcaaa acccccttaaa aataaggtta acccgcgagg   3600
cccccctaa                                                            3608
```

<210> SEQ ID NO 34
<211> LENGTH: 212
<212> TYPE: DNA
<213> ORGANISM: Homo sapiens

<400> SEQUENCE: 34

```
gggcagagcg cacatcgccc gcagtccccg agaagttggg gggagggggtc ggcaattgat     60
```

```
ccggtgccta gagaaggtgg cgcggggtaa actgggaaag tgatgtcgtg tactggctcc      120 gccttttcc cgagggtggg ggagaaccgt atataagtgc agtagtcgcc gtgaacgttc       180
tttttcgcaa cgggtttgcc gccagaacac ag                                    212
```

<210> SEQ ID NO 35  
<211> LENGTH: 2058  
<212> TYPE: DNA  
<213> ORGANISM: Gibbon leukemia virus
<400> SEQUENCE: 35

```
atggtattgc tgcctgggtc catgcttctc acctcaaacc tgcaccacct tcggcaccag       60
atgagtcctg ggagctggaa aagactgatc atcctcttaa gctgcgtatt cggcggcggc      120
gggacgagtc tgcaaaataa gaaccccac cagcccatga ccctcacttg gcaggtactg       180
tcccaaactg agacgttgt ctgggataca aaggcagtcc agcccccttg gacttggtgg      240
cccacactta aacctgatgt atgtgccttg gcggctagtc ttgagtcctg ggatatcccg      300
ggaaccgatg tctcgtcctc taaacgagtc agacctccgg actcagacta tactgccgct      360
tataagcaaa tcacctgggg agccataggg tgcagctacc ctcgggctag gactagaatg      420
gcaagctcta ccttctacgt atgtccccgg gatggccgga ccctttcaga gctagaagg       480 tgcgggggc tagaatccct atactgtaaa gaatgggatt gtgagaccac ggggaccggt      540
tattggctat ctaaatcctc aaaagacctc ataactgtaa aatgggacca aaatagcgaa      600
tggactcaaa aatttcaaca gtgtcaccag accggctggt gtaaccccct taaaatagat      660
ttcacagaca aaggaaaatt atccaaggac tggataacgg gaaaaaacctg gggattaaga      720 ttctatgtgt ctggacatcc aggcgtacag ttcaccattc gcttaaaaat caccaacatg      780
ccagctgtgg cagtaggtcc tgacctcgtc cttgtggaac aaggacctcc tagaacgtcc      840
ctcgctctcc cacctcctct tccccccaagg gaagcgccac cgccatctct ccccgactct      900
aactccacag ccctggcgac tagtgcacaa actcccacgg tgagaaaaac aattgttacc      960
ctaaacactc cgcctccac cacaggcgac agacttttg atcttgtgca gggggccttc      1020
ctaaccttaa atgctaccaa cccaggggcc actgagtctt gctggctttg tttggccatg     1080 ggccccccttc attatgaagc aatagcctca tcaggagagg tcgcctactc caccgacctt     1140
gaccggtgcc gctgggggac ccaaggaaag ctcacctca ctgaggtctc aggacacggg      1200
ttgtgcatag gaaaggtgcc ctttacccat cagcatctct gcaatcagac cctatccatc      1260
aattcctccg gagaccatca gtatctgctc ccctccaacc atagctggtg ggcttgcagc     1320
actggcctca cccttgcct ctccacctca gtttttaatc agactagaga tttctgtatc      1380
caggtccagc tgattcctcg catctattac tatcctgaag aagtttttgtt acaggcctat     1440 gacaattctc accccaggac taaagagag gctgtctcac ttaccctagc tgttttactg      1500
gggttgggaa tcacggcggg aataggtact ggttcaactg ccttaattaa aggacctata     1560
gacctccagc aaggctgac aagcctccag atcgccatag atgctgacct ccgggccctc      1620
caagactcag tcagcaagtt agaggactca ctgacttccc tgtccgaggt agtgctccaa      1680
aataggagag gccttgactt gctgtttcta aagaaggtg gcctctgtgc ggccctaaag      1740
gaagagtgct gtttttacat agaccactca ggtgcagtac gggactccat gaaaaaactc     1800
aaagaaaaac tggataaaag acagttagag cgccagaaaa gccaaactg gtatgaagga     1860 tggttcaata actcccctttg gttcactacc ctgctatcaa ccatcgctgg gccctatta      1920
```

```
ctcctccttc tgttgctcat cctcgggcca tgcatcatca ataagttagt tcaattcatc    1980
aatgatagga taagtgcagt taaaattctg gtccttagac aaaaatatca ggccctagag    2040
aacgaaggta acctttaa                                                 2058
```

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36

```
cggcggccgc atggtgacag ggggaatggc                                      30
```

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37

```
cggtttaaac ctactcacca atatcttcaa a                                    31
```

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38

```
cggcggccgc atggtgaccg gcggcatggc                                      30
```

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39

```
cggtttaaac ttactcgccg atatcctcga                                      30
```

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40

```
cggcggccgc atggttactg gagggatggc                                      30
```

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41

```
cggtttaaac tcattcgcca atatcctcga                                      30
```

```
<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
cggcggccgc atggtaactg gtggcatggc                                         30

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
cggtttaaac ctactctccg atatcctcaa                                         30

<210> SEQ ID NO 44
<211> LENGTH: 29
<212> TYPE: DNA
<213> ORGANISM: Artificial Sequence
<220> FEATURE:
<223> OTHER INFORMATION: primer

<400> SEQUENCE: 44
cggcggccgc atggttactg ggggaatgg                                          29

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
cggtttaaac ttattccccg atgtcttcga                                         30
```

GENE THERAPY VECTOR SYSTEM AND PRODRUG GENES

CROSS-REFERENCE TO RELATED APPLICATIONS

This application is a continuation of PCT/KR2016/013881, filed Nov. 29, 2016, the contents of which is incorporated herein by reference.

FIELD OF INVENTION

The present invention relates to a replicating retrovirus vector system, comprising thymidine kinase (HSV-TK) gene and cytosine deaminase (CD) gene, which enable the gene transfer to tumor tissue for the efficient cancer therapy.

BACKGROUND OF THE INVENTION

Gene therapy is a general term that indicates a technique to treat disease by replacing an abnormal gene that causes disease in cells or tissues in a patient with a target gene or by inserting a target gene that is helpful for the treatment of disease therein. In the early development days of gene therapy products, the major principle of gene therapy was to induce the specific gene expression by inserting foreign DNA into the target cell chromosome. However, today's gene therapy includes the method using antisense to inhibit the expression of a gene related to a specific disease by using antisense oligodeoxynucleotide or siRNA.

The mentioned gene therapy takes a totally different approach from the conventional treatment methods, so that can investigate a reason of disease at a molecular level for better treatment. This method is also advantageous in reducing unnecessary side effects frequently observed in other treatment methods due to its nucleotide sequence specific function that can eliminate the factors related to major diseases. Such a method targeting gene as the above does not need a separate step of optimization in the course of drug production as long as the nucleotide sequence of a target gene for the control of expression level is identified, indicating the production procedure is simpler than that for an antibody or compound drugs. In addition, this method can target any disease which other methods cannot take it as a target, once a causing gene of the disease is identified, suggesting that gene therapy has a full potential as a next generation treatment agent. Numbers of researches confirmed that the chances of successful treatment for incurable disease, cancer, AIDS, genetic disorder, and neurologic disorder which are hard to treat with the conventional medicinal treatment methods could be increased with gene therapy, and therefore gene therapy is now being applied to actual clinical trials (YOUNG et al, 2006).

A gene medicine is composed of a gene transfer vector and a therapeutic gene. As a tool to deliver a gene in vivo, the gene transfer vector is largely divided into a viral vector and a non-viral vector. The viral vector is prepared by making a virus non-replicable by eliminating most of or a part of essential genes and instead inserting a therapeutic gene therein (Lotze M T et al., Cancer Gene Therapy, 9:692-699, 2002). The viral vector can deliver a gene with high efficiency but has problems of difficulty in mass-production according to the types of virus, causing immune response, toxicity, or introducing replicable virus, etc. The major viral vectors being used for the development of a gene medicine are exemplified by retrovirus, lentivirus, adenovirus, adeno-associated virus (AAV), herpes simplex virus, and pox virus etc. In the meantime, the non-viral vector does not cause immune response, has low toxicity, and is easy to mass-produce, but is not efficient in delivering a gene and can only induce temporary gene expression.

One of the most frequently used viral vector in the field of clinical trial is a retrovirus vector, which was first used in the first gene therapy clinical trial performed by NIH in 1990. This vector is regarded as the most useful vector for a stable gene insertion. The retrovirus vector based on moloney murine leukemia virus (MoMLV) is widely used in various clinical trials for gene therapy.

The non-replicating retrovirus whose self-replication is defective is suitable for the insertion of a relatively big gene. The titer thereof is $10^6 \sim 10^7$ pfu/ml, so there is not a big problem in the infection of a target cell with this vector. Also, the packaging cell line has been already established, indicating that the preparation of this vector is easy. In addition, the retrovirus vector can be scaled-up by means of inserting a therapeutic gene in the retrovirus plasmid, with which the packaging cell line is infected to produce the recombinant virus; and infecting a target cell with the produced recombinant virus. However, there is a chance of mutation caused in the course of retroviral integration into chromosome.

Meanwhile, the genome stability of the self-replicable retrovirus vector in the proliferating cell such as a cancer cell has been an issue. Besides, a foreign gene that can be inserted in the self-replicable virus vector for gene therapy is limited up to 1.3 kb in the size, indicating the insertion of various therapeutic genes is not easy (*J. of virology*, Vol. 75, 6989-6998, 2001).

The therapeutic gene usable for gene therapy is exemplified by the gene inducing cancer cell apoptosis by using a prodrug such as herpes simplex virus thymidine kinase or cytosine deaminase; the cytokine gene accelerating immune response such as interleukin-12 or GM-CSF, etc; and the tumor specific antigen gene such as CEA or Her-2, etc. (Gottesman M M, *Cancer Gene Therapy*, 10:501-508, 2003). Suicide gene kills cancer cells when it is delivered into the cancer cells. Cytokine gene or tumor specific antigen gene attacks cancer cells by activating immune response against cancer.

Recently, studies have been actively going on about the synthesis technique of enzyme/prodrug that exhibits selective antitumor effect on malignant tumor. Realistically, when suicide gene is expressed in cancer tissues and its precursor is administered in vivo systemically, it does not cause toxicity in normal cells but the precursor is converted into a toxic material to kill tumor cells only in those tumor cells where the therapeutic gene is expressed.

One of the most generally used suicide gene is herpes simplex virus thymidine kinase (HSV-TK). When the prodrug ganciclovir (GCV) which does no harm on cells is converted into a cytotoxic material through enzyme reaction, it acquires bystander effect that can induce the apoptosis of not only the cells harboring the suicide gene but also the neighboring cells by gap junction. The effect and stability of the gene has been confirmed so far until the phase 3 clinical trial (*human gene therapy*, 4:725-731, 1993; *molecular therapy*, 1:195-203, 2000).

Another suicide gene is cytosine deaminase (CD), which induces deamination of 5-fluorocytosine (5-FC) to produce a powerful anticancer agent 5-fluorouracil (5-FU). 5-FU is metabolized into 5-fluorouridine triphosphate (5-FUTP) and 5-fluorodeoxyuridine monophosphate (5-FdUMP). 5-FUTP fused to ribonucleic acid interrupts the synthesis of ribosomal ribonucleic acid and messenger ribonucleic acid. In the meantime, 5-FdUMP suppresses thymidine synthase irreversibly, leading to the inhibition of DNA synthesis. Therefore, tumor cells can be selectively killed by converting such prodrugs as GCV and 5-FC into toxic metabolites in the tumor cells expressing TK or CD.

Using more than 2 different therapeutic genes simultaneously for gene therapy is more efficient in disease treatment and particularly in dealing with the disease displaying resistance against a specific gene used for gene therapy. In relation to such a technique, a gene therapy vector system that can express TK and CD simultaneously in the cancer tissue is very much advantageous, particularly for the treatment of such cancers reported to have resistance against TK and CD treatment. However, when HSV-TK and CD are both inserted in a replicating-retrovirus vector (RRV), the genome size becomes 10 kb or more, indicating the insertion of the two genes at the same time in a single retrovirus vector is in fact impossible. When a replicating-retrovirus vector is used for gene therapy, it has to contain a foreign gene in addition to its original endogenous genomic RNA, so that the size of the genomic RNA is getting bigger and has a high potential of therapeutic gene loss because of recombination caused by the additional heterologous nucleotide sequence introduced therein, making the construction of a vector system difficult.

The present inventors tried to develop a safe virus vector system for gene therapy which is free from recombination. As a result, the inventors developed a TK/CD combined self-replicating retrovirus vector system containing both HSV-TK and CD genes with excellent stability but without worry of recombination caused gene loss. The present inventors confirmed that the said vector could induce cancer cell death by using the prodrug GCV or 5-FC and be selectively applied to the treatment of specific cancer that showed resistance against either TK or CD by selecting a proper therapeutic gene and the prodrug thereof. The present inventors further completed this invention by confirming that the said vector thereby could be useful as a pharmaceutical composition for the prevention or treatment of cancer.

SUMMARY OF THE INVENTION

It is an object of the present invention to provide a replicating retrovirus vector system harboring thymidine kinase and cytosine deaminase genes for the treatment of cancer.

It is another object of the present invention to provide a recombinant retrovirus containing the retrovirus vector system and a host cell infected with the recombinant retrovirus above.

It is also an object of the present invention to provide a pharmaceutical composition for the treatment of cancer and a composition for gene transfer comprising the recombinant retrovirus above.

It is further an object of the present invention to provide a method for preparing the replicating retrovirus system above.

To achieve the above objects, the present invention provides a replicating retrovirus vector system comprising the first recombinant expression vector containing MuLV Gag-Pol gene, promoter, and cytosine deaminase gene; and the second recombinant expression vector containing virus Env gene, promoter, and thymidine kinase gene.

In addition, the present invention also provides a replicating retrovirus vector system comprising the first recombinant expression vector containing MuLV Gag-Pol gene, promoter, and thymidine kinase gene; and the second recombinant expression vector containing virus Env gene, promoter, and cytosine deaminase gene.

In addition, the present invention also provides a recombinant retrovirus containing the vector system.

In addition, the present invention also provides a host cell transfected with the recombinant retrovirus above.

In addition, the present invention also provides a pharmaceutical composition for the prevention or treatment of cancer containing the recombinant retrovirus as an active ingredient.

In addition, the present invention also provides a composition for gene transfer for the treatment of cancer comprising the recombinant retrovirus above.

In addition, the present invention also provides a method for preparing the replicating retrovirus vector system comprising the step of preparing the first recombinant expression vector containing MuLV Gag-Pol gene, promoter, and cytosine deaminase gene; and the step of preparing the second recombinant expression vector containing virus Env gene, promoter, and thymidine kinase gene.

In addition, the present invention also provides a method for preparing the replicating retrovirus vector system comprising the step of preparing the first recombinant expression vector containing MuLV Gag-Pol gene, promoter, and thymidine kinase gene; and the step of preparing the second recombinant expression vector containing Env gene, promoter, and cytosine deaminase gene.

In addition, the present invention also provides a method for treating cancer containing the step of administering the recombinant retrovirus above to a subject in need of the same.

Lastly, the present invention provides a use of the retrovirus above for the production of a drug for the prevention or treatment of cancer.

The TK/CD combined self-replicating retrovirus vector system of the present invention includes both HSV-TK and CD genes; has no worries about losing a therapeutic gene caused by the recombination in the course of virus infection; and has an excellent stability, and also is able to induce cancer cell death by using the prodrug GCV or 5-FC and can apply a therapeutic gene or a prodrug thereof selectively to such cancer that shows resistance against cancer treatment using either TK or CD, so that this system of the invention can be advantageously used as a pharmaceutical composition for the treatment of cancer.

BRIEF DESCRIPTION OF THE DRAWINGS

FIG. 1a is a schematic vector diagram illustrating the structures of spRRVe-P1-TK and sRRVgp-P1-RFP.

FIG. 1b is a schematic vector diagram illustrating the structures of sRRVgp-P1-TK and spRRVe-P1-GFP.

FIG. 2a is a diagram illustrating the virus titers of spRRVe-P1-TK/sRRVgp-P1-RFP and sRRVgp-P1-TK/spRRVe-P1-GFP.

FIG. 2b is an extension of the diagram illustrating the virus titers of spRRVe-P1-TK/sRRVgp-P1-RFP and sRRVgp-P1-TK/spRRVe-P1-GFP.

FIG. 3a is a diagram illustrating whether the recombination occurs or not in spRRVe-P1-TK/sRRVgp-P1-RFP virus vector.

FIG. 3b is a diagram illustrating whether the recombination occurs or not in sRRVgp-P1-TK/spRRVe-P1-GFP virus vector.

FIG. 4 is a diagram illustrating the analysis of the recombination pattern of spRRVe-P1-TK vector.

FIG. 5 is a schematic diagram illustrating the structures of spRRVe-P1-yCD and sRRVgp-P1-RFP vector.

FIG. 6 is a diagram illustrating whether the recombination occurs or not in spRRVe-P1-yCD and sRRVgp-P1-RFP vector.

FIG. 7 is a diagram illustrating the analysis of the recombination pattern of spRRVe-P1-yCD vector.

FIG. 8 is a schematic diagram illustrating the structure of spRRVe-P1-yCD/sRRVgp-P1-TK vector.

FIG. 9 is a diagram illustrating whether the recombination occurs or not in spRRVe-P1-yCD/sRRVgp-P1-TK vector.

FIG. 10 is a diagram illustrating the analysis of the recombination pattern of spRRVe-P1-yCD vector.

FIG. 11 is a diagram illustrating the analysis of the recombination pattern of sRRVgp-P1-TK vector.

Figure 12:
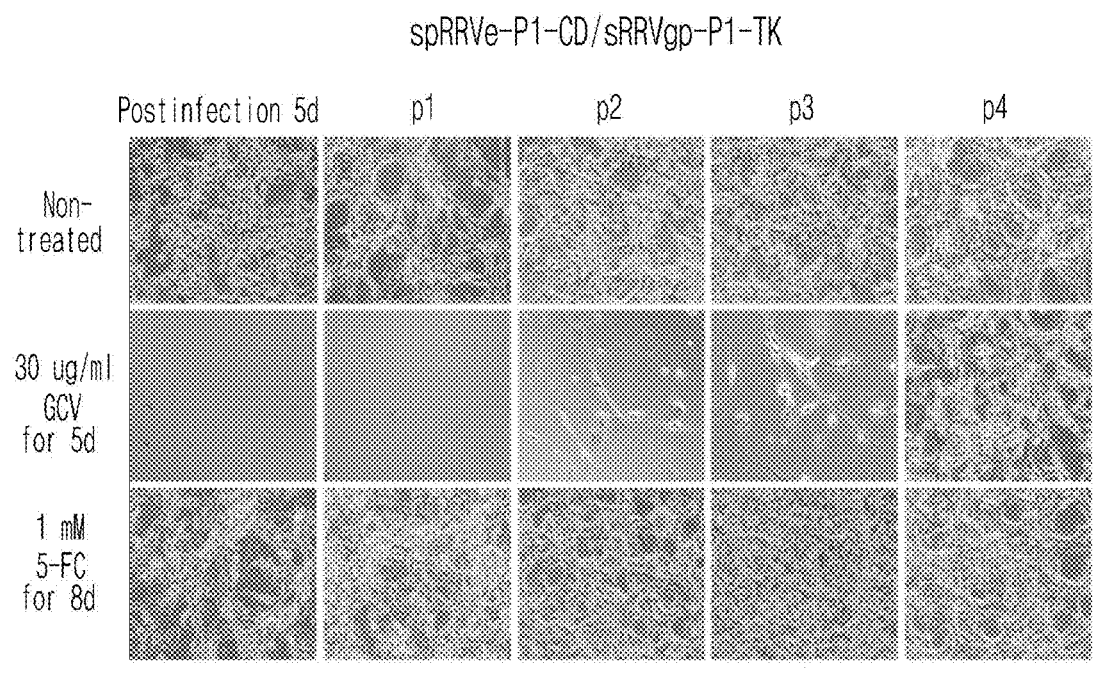

FIG. 12 is a diagram illustrating the drug sensitivity of spRRVe-P1-yCD/sRRVgp-P1-TK.

FIG. 13 is a schematic diagram illustrating the structures of spRRVe-P1-CDa, spRRVe-P1-CDb, and spRRVe-P1-CDc vector.

FIG. 14 is a diagram illustrating whether the recombination occurs or not in spRRVe-P1-CDa, spRRVe-P1-CDb, and spRRVe-P1-CDc vectors.

FIG. 15 is a diagram illustrating the analysis of the recombination pattern of spRRVe-P1-CDa vector.

FIG. 16 is a schematic diagram illustrating the structures of spRRVe-P1-CD2, spRRVe-P1-CD3, spRRVe-P1-CD4, spRRVe-P1-CD5, spRRVe-P1-CD6, spRRVe-P1-CD7, spRRVe-P1-CD8, and spRRVe-P1-CD9.

Figure 17B:
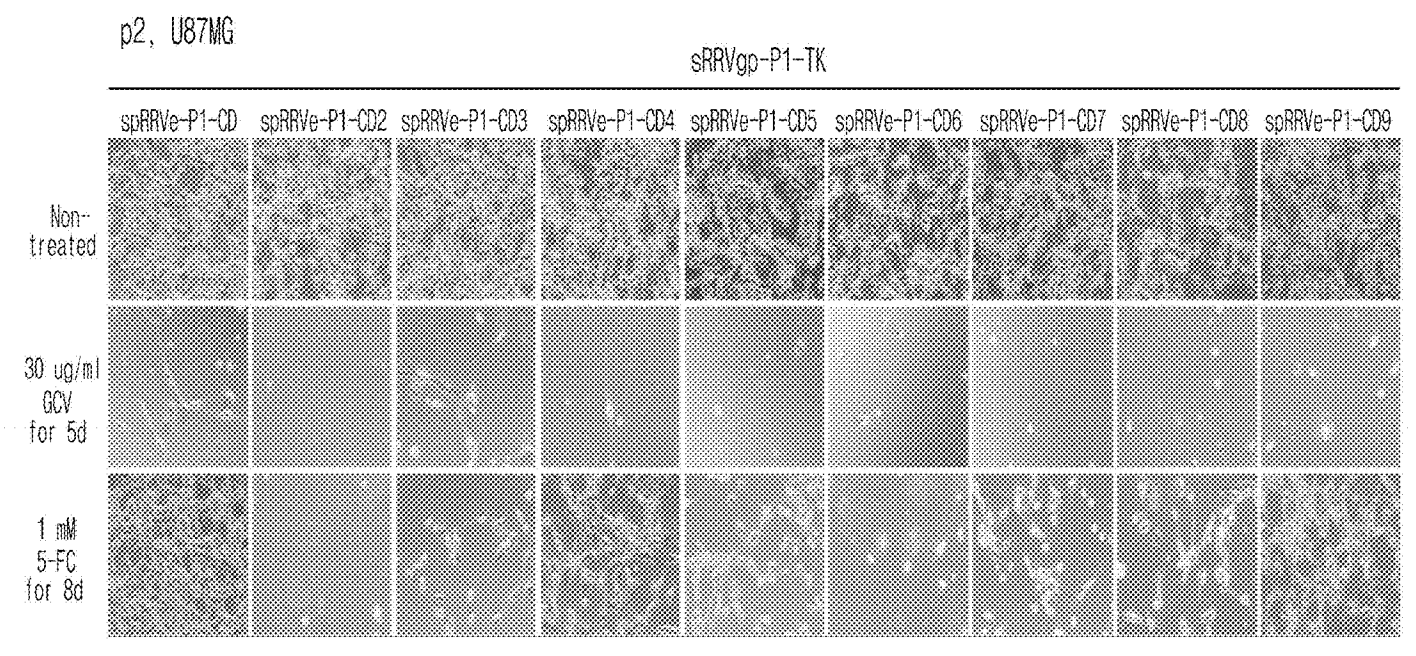
Figure 17C:
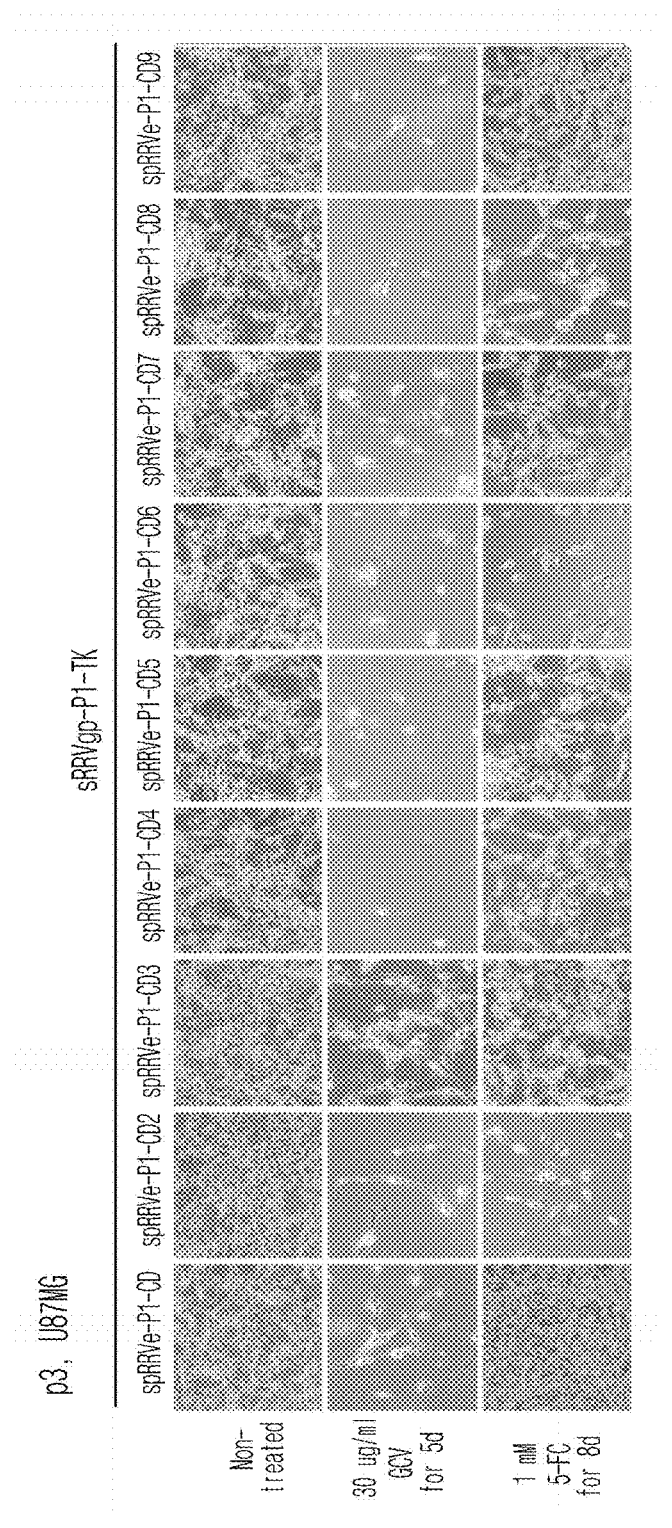

FIG. 17*a* is a diagram illustrating the drug sensitivity of spRRVe-P1-CD2, spRRVe-P1-CD3, spRRVe-P1-CD4, spRRVe-P1-CD5, spRRVe-P1-CD6, spRRVe-P1-CD7, spRRVe-P1-CD8, and spRRVe-P1-CD9 in the phase of p1.

FIG. 17*b* is a diagram illustrating the drug sensitivity of spRRVe-P1-CD2, spRRVe-P1-CD3, spRRVe-P1-CD4, spRRVe-P1-CD5, spRRVe-P1-CD6, spRRVe-P1-CD7, spRRVe-P1-CD8, and spRRVe-P1-CD9 in the phase of p2.

FIG. 17*c* is a diagram illustrating the drug sensitivity of spRRVe-P1-CD2, spRRVe-P1-CD3, spRRVe-P1-CD4, spRRVe-P1-CD5, spRRVe-P1-CD6, spRRVe-P1-CD7, spRRVe-P1-CD8, and spRRVe-P1-CD9 in the phase of p3.

FIG. 17*d* is a diagram illustrating the drug sensitivity of spRRVe-P1-CD2, spRRVe-P1-CD3, spRRVe-P1-CD4, spRRVe-P1-CD5, spRRVe-P1-CD6, spRRVe-P1-CD7, spRRVe-P1-CD8, and spRRVe-P1-CD9 in the phase of p4.

FIG. 18 is a diagram illustrating whether the recombination occurs or not in spRRVe-P1-CD2, spRRVe-P1-CD3, spRRVe-P1-CD4, spRRVe-P1-CD5, spRRVe-P1-CD6, spRRVe-P1-CD7, spRRVe-P1-CD8, and spRRVe-P1-CD9 vectors.

FIG. 19*a* is a diagram illustrating the analysis of the recombination pattern of spRRVe-P1-CD6 vector.

FIG. 19*b* is an extension of the diagram illustrating the analysis of the recombinant pattern of spRRVe-P1-CD6 vector.

FIG. 20*a* is a diagram illustrating the analysis of the recombination pattern of spRRVe-P1-CD8 vector.

FIG. 20*b* is an extension of the diagram illustrating the analysis of the recombinant pattern of spRRVe-P1-CD8 vector.

FIG. 21 is a schematic diagram illustrating the structures of spRRVe-P2-yCD, spRRVe-P2-CD2, spRRVe-P2-CD3, spRRVe-P2-CD5, spRRVe-P2-CD6, spRRVe-P2-CD7, spRRVe-P2-CD8, and spRRVe-P2-CD9.

Figure 22A:
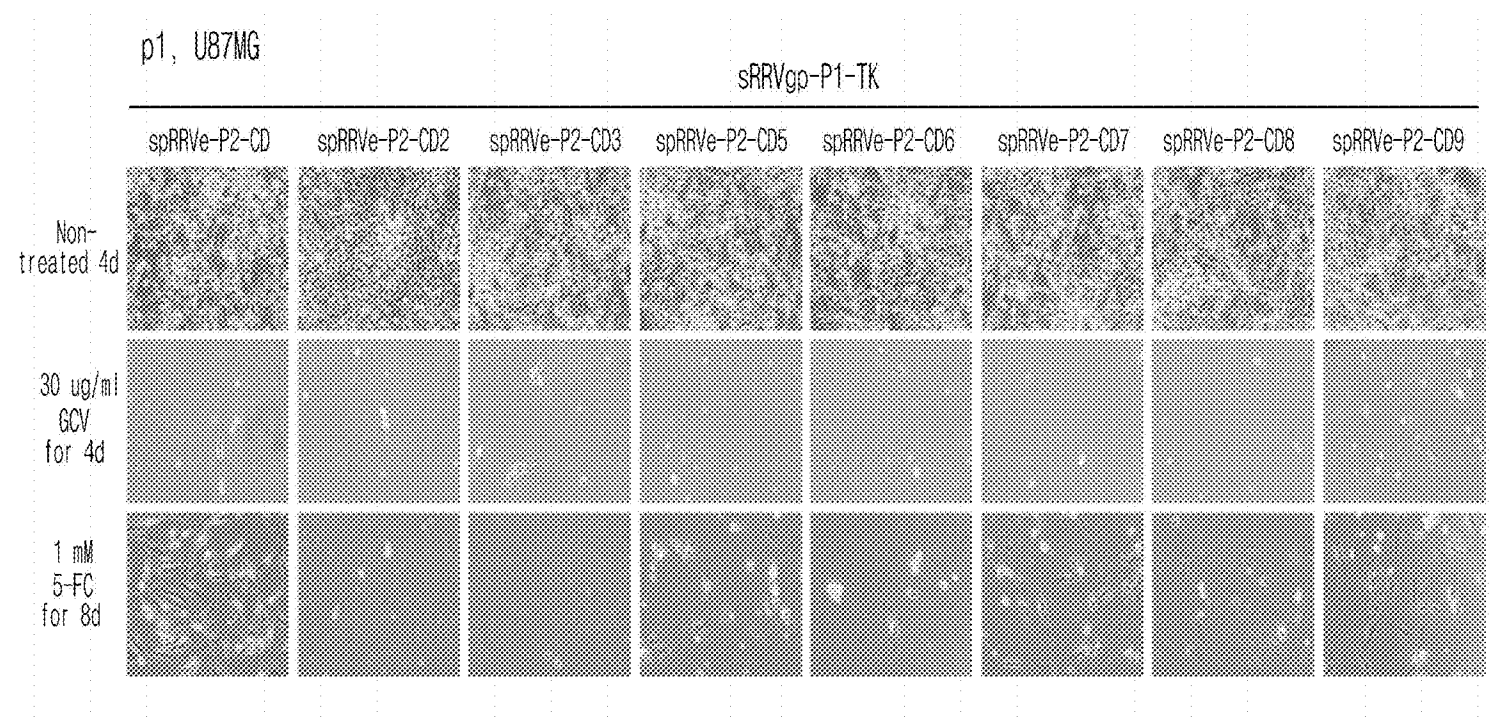
Figure 22B:
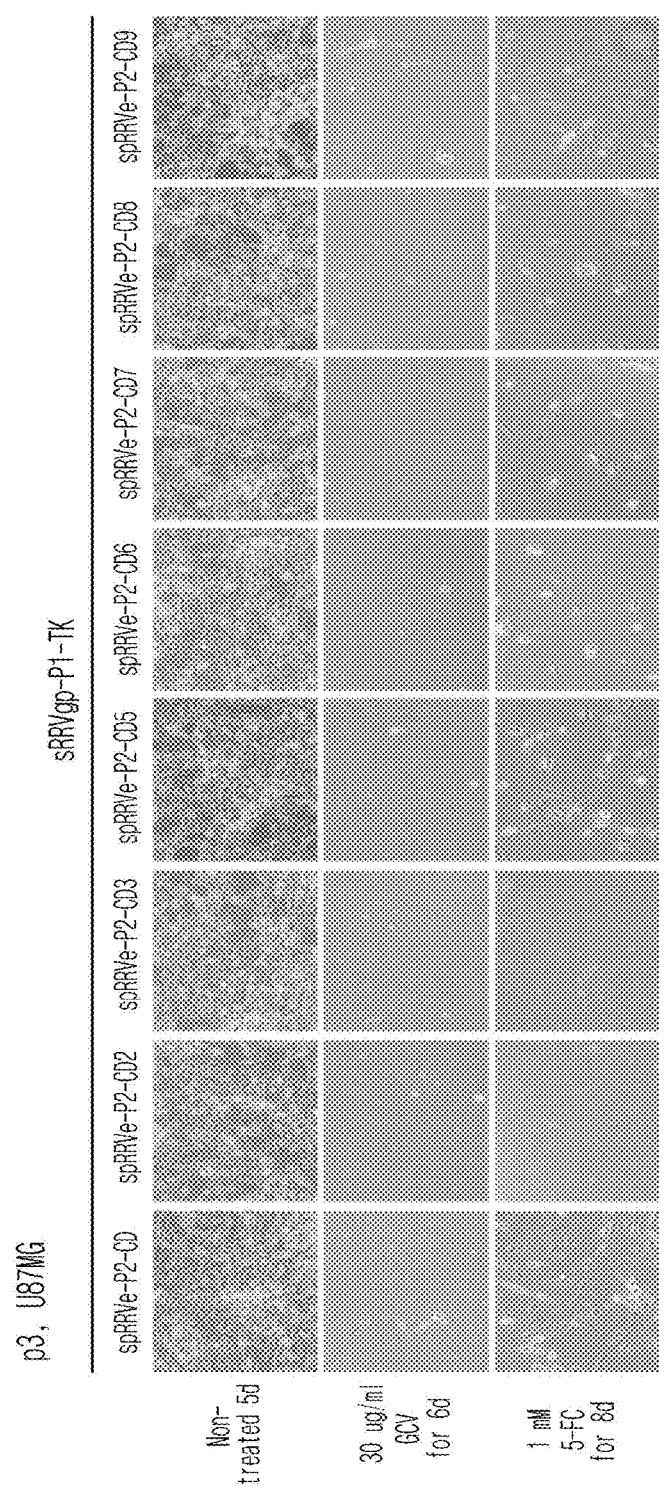
Figure 22C:
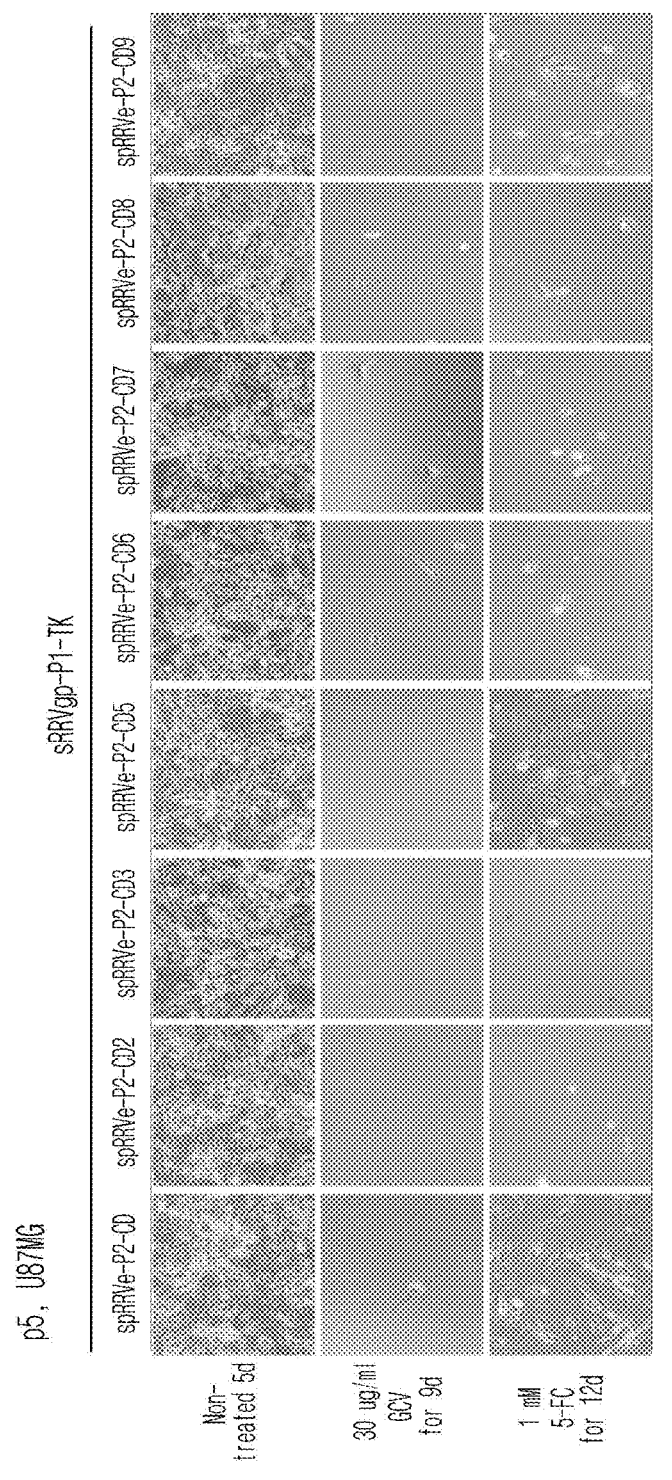
Figure 22D:
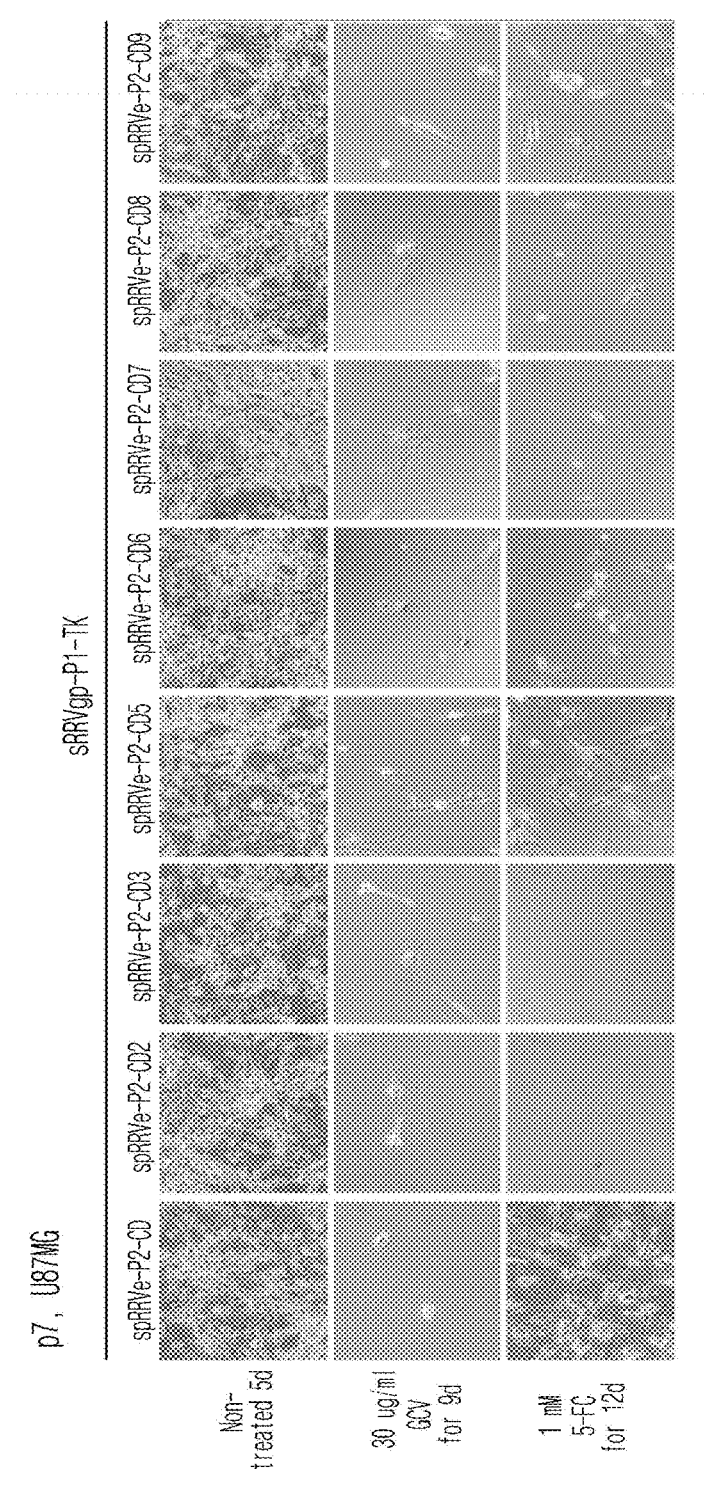
Figure 22E:
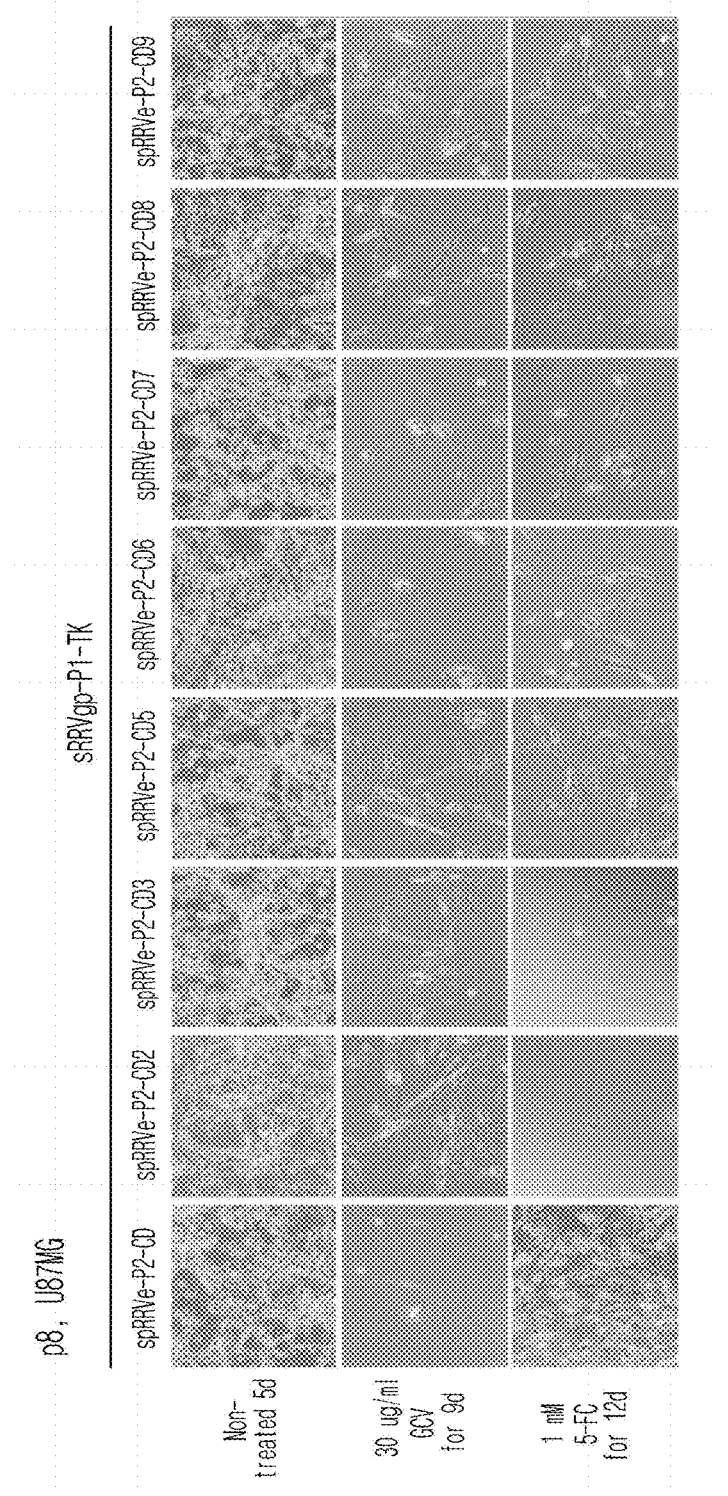

FIG. 22*a* is a diagram illustrating the drug sensitivity of spRRVe-P2-CD2, spRRVe-P2-CD3, spRRVe-P2-CD5, spRRVe-P2-CD6, spRRVe-P2-CD7, spRRVe-P2-CD8, and spRRVe-P2-CD9 in the phase of p1.

FIG. 22*b* is a diagram illustrating the drug sensitivity of spRRVe-P2-CD2, spRRVe-P2-CD3, spRRVe-P2-CD5, spRRVe-P2-CD6, spRRVe-P2-CD7, spRRVe-P2-CD8, and spRRVe-P2-CD9 in the phase of p3.

FIG. 22*c* is a diagram illustrating the drug sensitivity of spRRVe-P2-CD2, spRRVe-P2-CD3, spRRVe-P2-CD5, spRRVe-P2-CD6, spRRVe-P2-CD7, spRRVe-P2-CD8, and spRRVe-P2-CD9 in the phase of p5.

FIG. 22*d* is a diagram illustrating the drug sensitivity of spRRVe-P2-CD2, spRRVe-P2-CD3, spRRVe-P2-CD5, spRRVe-P2-CD6, spRRVe-P2-CD7, spRRVe-P2-CD8, and spRRVe-P2-CD9 in the phase of p7.

FIG. 22*e* is a diagram illustrating the drug sensitivity of spRRVe-P2-CD2, spRRVe-P2-CD3, spRRVe-P2-CD5, spRRVe-P2-CD6, spRRVe-P2-CD7, spRRVe-P2-CD8, and spRRVe-P2-CD9 in the phase of p8.

FIG. 22*f* is a diagram illustrating the drug sensitivity of spRRVe-P2-CD2, spRRVe-P2-CD3, spRRVe-P2-CD5, spRRVe-P2-CD6, spRRVe-P2-CD7, spRRVe-P2-CD8, and spRRVe-P2-CD9 in the phase of p9.

FIG. 23 is a diagram illustrating whether the recombination occurs or not in spRRVe-P2-yCD, spRRVe-P2-CD2, spRRVe-P2-CD3, spRRVe-P2-CD5, spRRVe-P2-CD6, spRRVe-P2-CD7, spRRVe-P2-CD8, spRRVe-P2-CD9, and sRRVgp-P1-TK.

FIG. 24 is a diagram illustrating the analysis of the recombination pattern of sRRVgp-P1-TK vector.

FIG. 25 is a schematic diagram illustrating the structure of sRRVgp-P2-TK vector.

FIG. 26*a* is a diagram illustrating the drug sensitivity of spRRVe-P2-CD6, spRRVe-P2-CD7, and spRRVe-P2-CD8 in the phases of p1 and p3.

FIG. 26*b* is a diagram illustrating the drug sensitivity of spRRVe-P2-CD6, spRRVe-P2-CD7, and spRRVe-P2-CD8 in the phases of p5 and p7.

FIG. 26*c* is a diagram illustrating the drug sensitivity of spRRVe-P2-CD6, spRRVe-P2-CD7, and spRRVe-P2-CD8 in the phases of p9 and p11.

FIG. 27*a* is a diagram illustrating whether the recombination occurs or not in spRRVe-P2-CD6, spRRVe-P2-CD7, or spRRVe-P2-CD8/sRRVgp-P2-TK, confirmed by using MuLV4194F and MFGSacIR primers.

FIG. 27*b* is a diagram illustrating whether the recombination occurs or not in spRRVe-P2-CD6, spRRVe-P2-CD7, or spRRVe-P2-CD8/sRRVgp-P2-TK vectors, confirmed by using GaLV1624F and MFGSacIR primers.

FIG. 28*a* is a diagram illustrating the analysis of the recombination pattern of spRRVe-P2-CD6 vector.

FIG. 28*b* is an extension of the diagram illustrating the analysis of the recombinant pattern of spRRVe-P2-CD6 vector.

FIG. 29*a* is a diagram illustrating the analysis of the recombination pattern of spRRVe-P2-CD8 vector.

FIG. 29*b* is an extension of the diagram illustrating the analysis of the recombinant pattern of spRRVe-P2-CD8 vector.

FIG. 30*a* is a diagram illustrating the drug sensitivity of spRRVe-P2-CD6, spRRVe-P2-CD10, spRRVe-P2-CD11, spRRVe-P2-CD12, spRRVe-P2-CD13, spRRVe-P2-CD14, spRRVe-P2-CD15, or spRRVe-P2-CD16 in the phase of p1.

FIG. 30*b* is a diagram illustrating the drug sensitivity of spRRVe-P2-CD6, spRRVe-P2-CD10, spRRVe-P2-CD11, spRRVe-P2-CD12, spRRVe-P2-CD13, spRRVe-P2-CD14, spRRVe-P2-CD15, or spRRVe-P2-CD16 virus in the phase of p3.

FIG. 30c is a diagram illustrating the drug sensitivity of spRRVe-P2-CD6, spRRVe-P2-CD10, spRRVe-P2-CD11, spRRVe-P2-CD12, spRRVe-P2-CD13, spRRVe-P2-CD14, spRRVe-P2-CD15, or spRRVe-P2-CD16 virus in the phase of p5.

FIG. 31 is a schematic diagram illustrating the vector structures of sRRVgp-P2-CD2, sRRVgp-P2-CD6, sRRVgp-P2-CD7, and sRRVgp-P2-CD8.

FIG. 32 is a schematic diagram illustrating the structure of spRRVe-P2-TK.

Figure 33A:
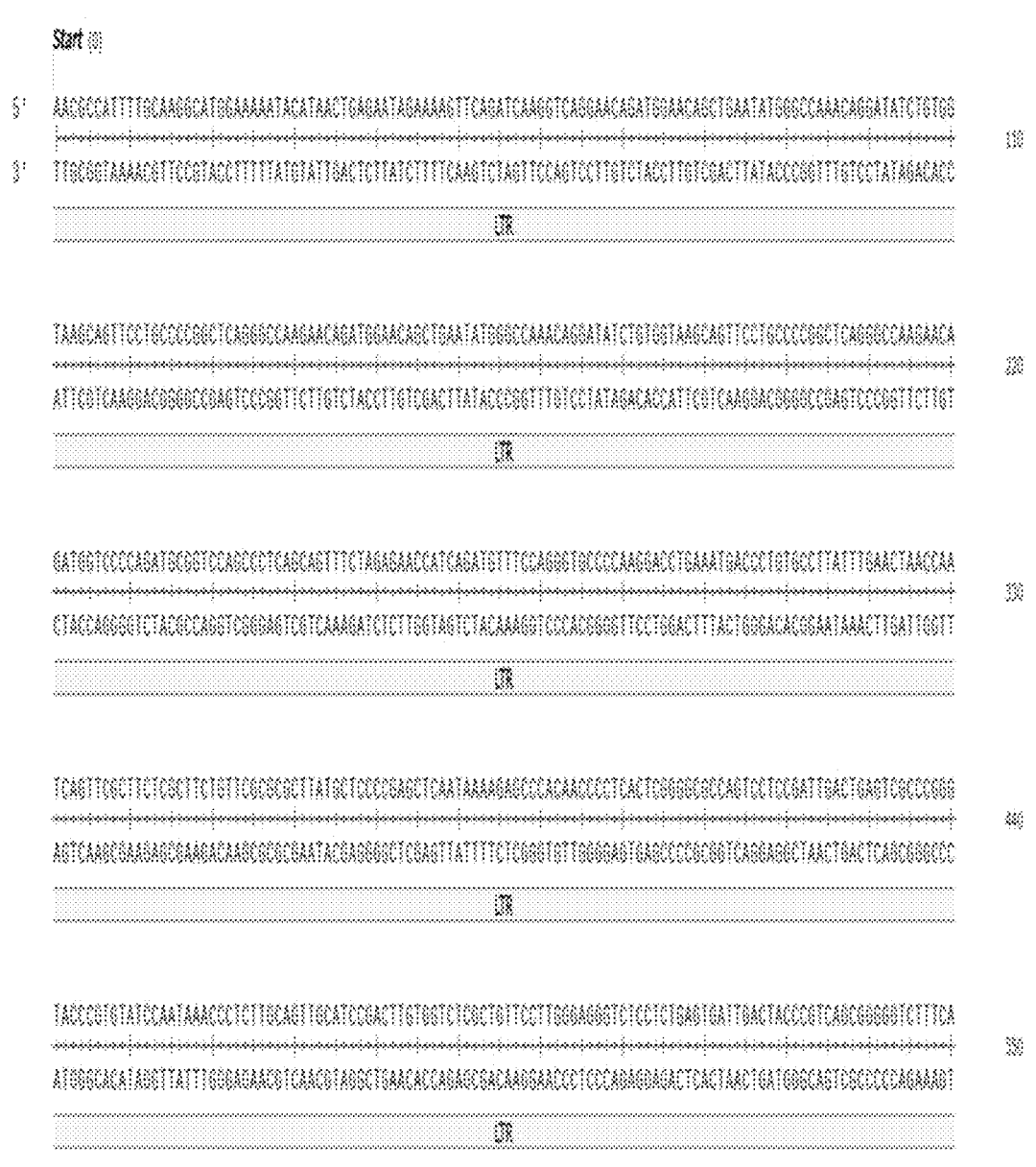
Figure 33B:
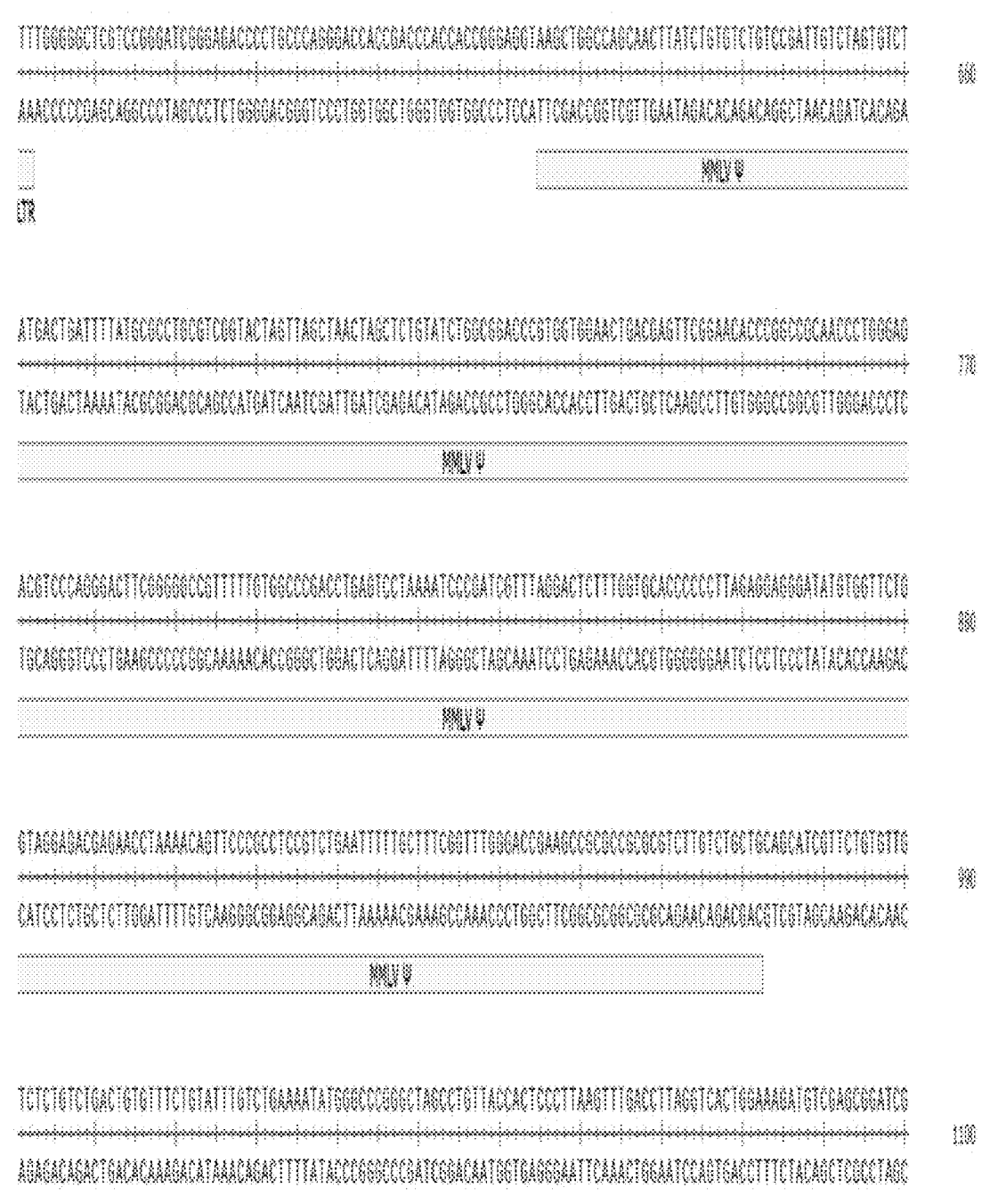
Figure 33C:
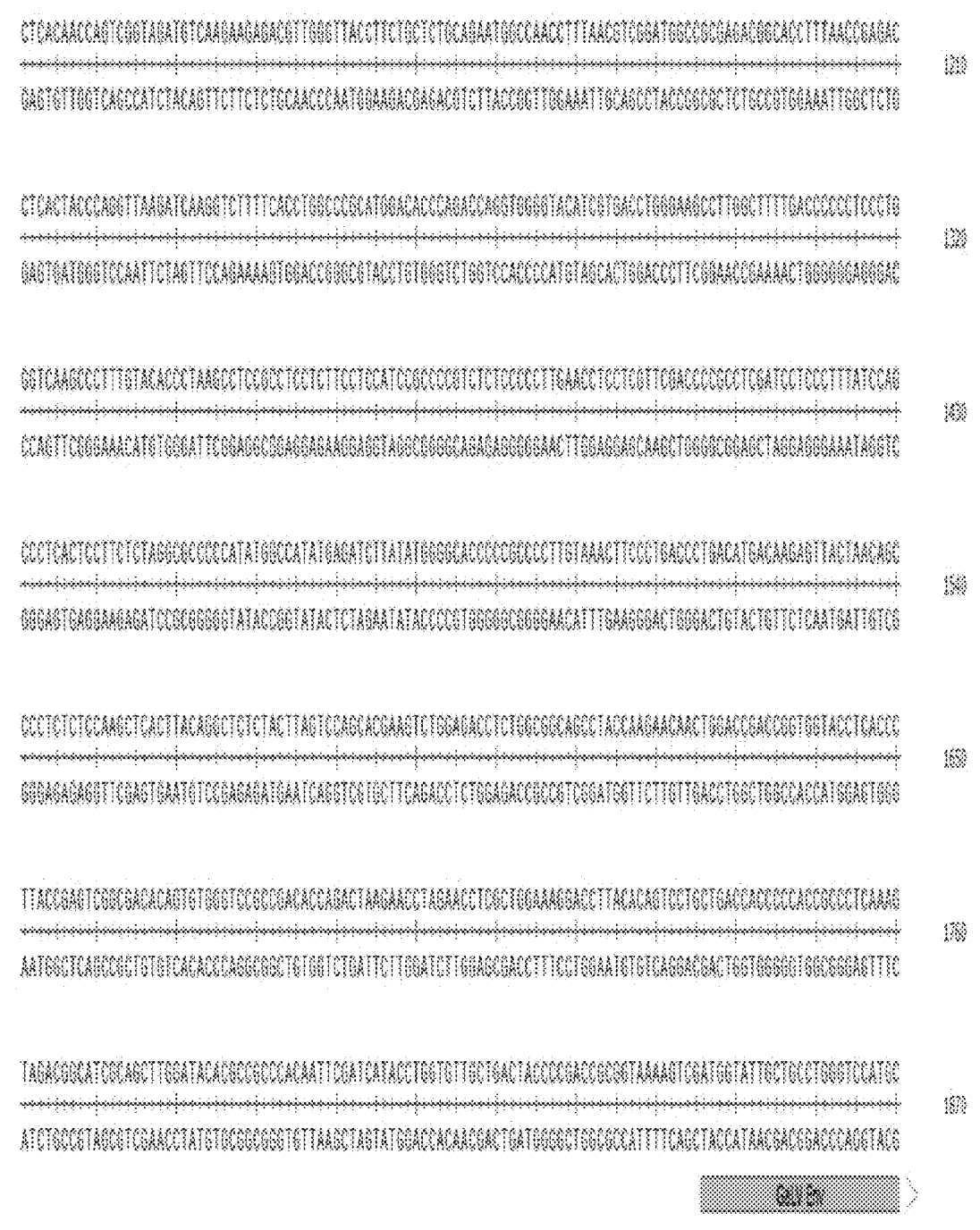
Figure 33E:
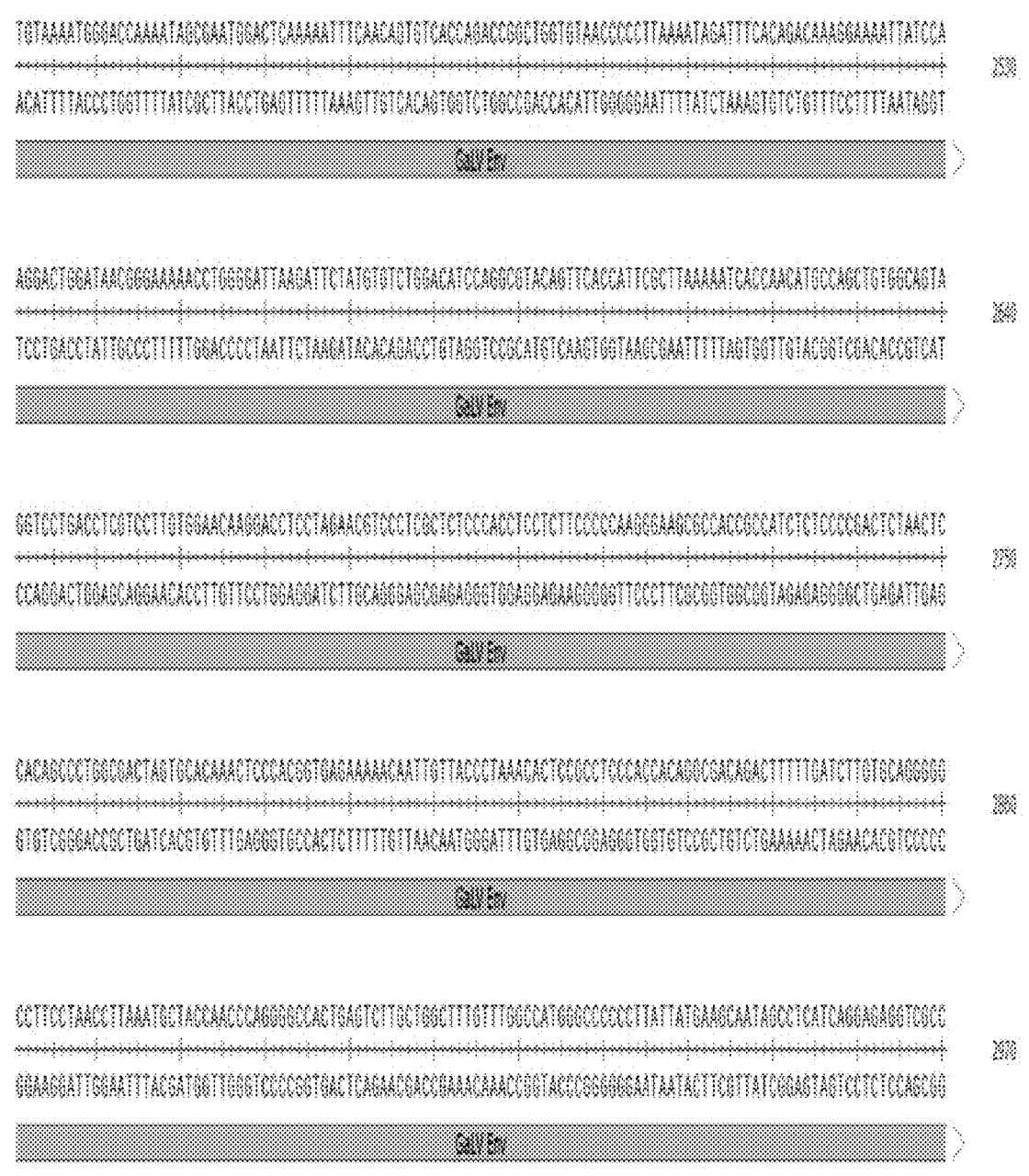
Figure 33F:
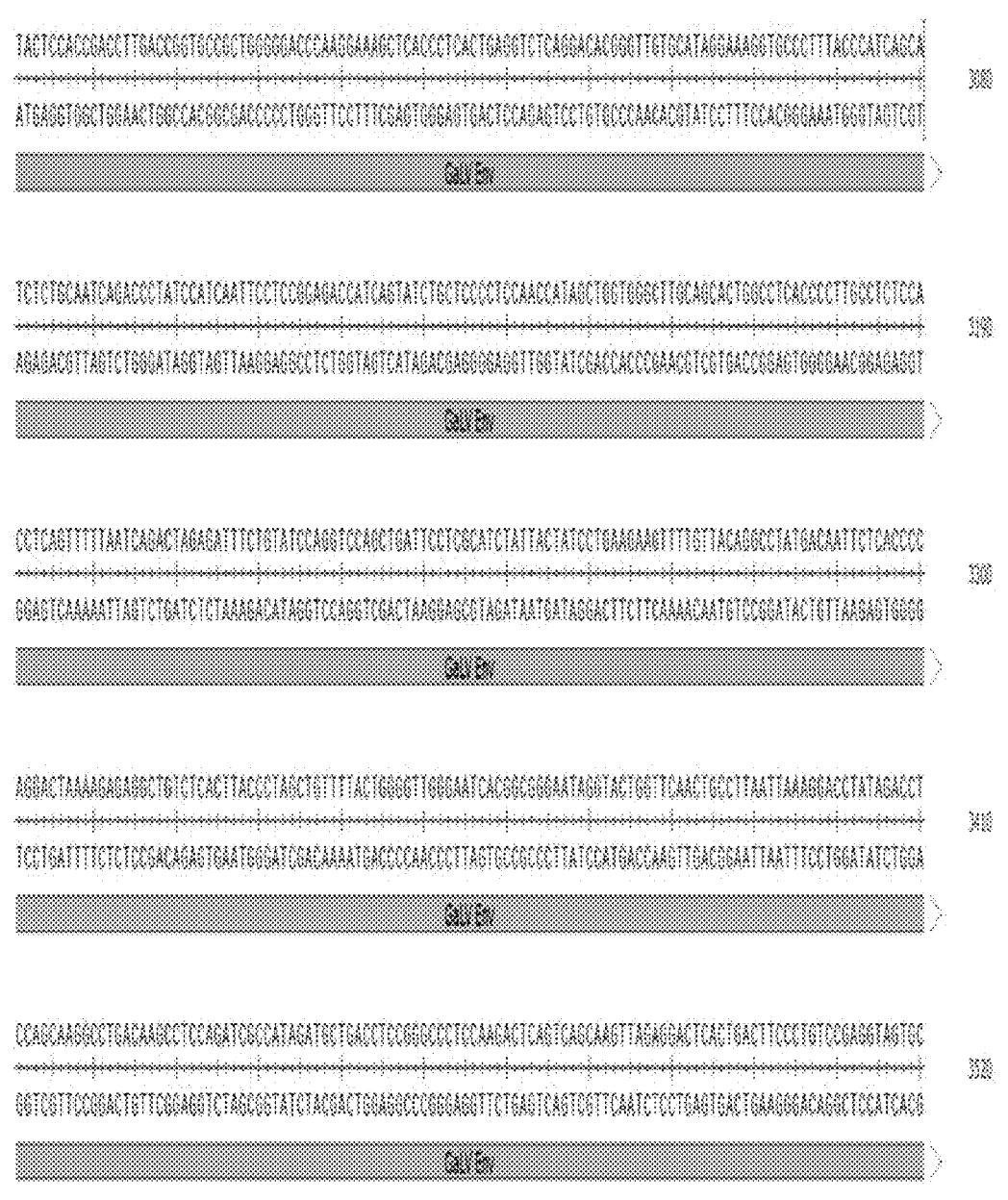
Figure 33G:
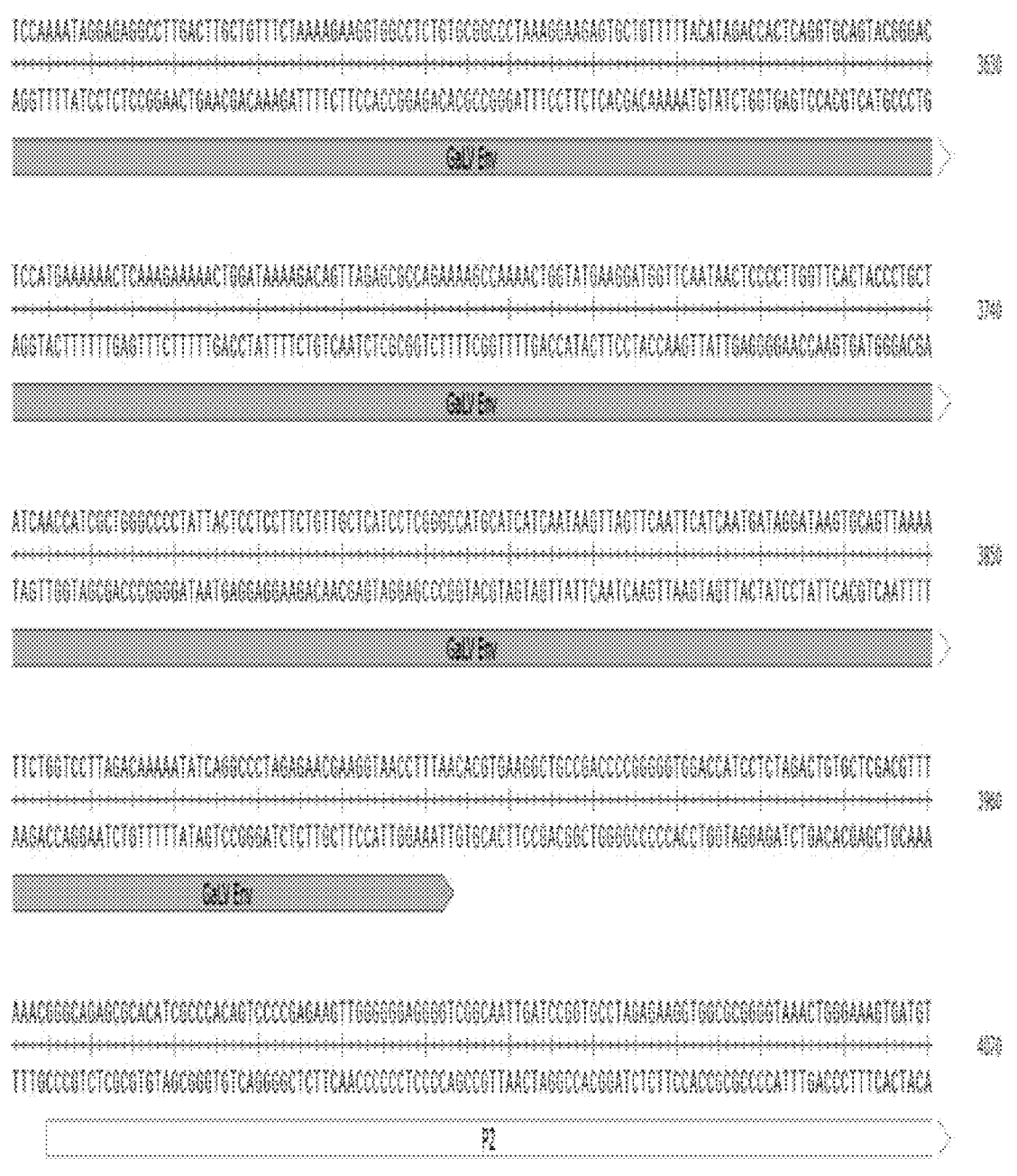
Figure 33H:
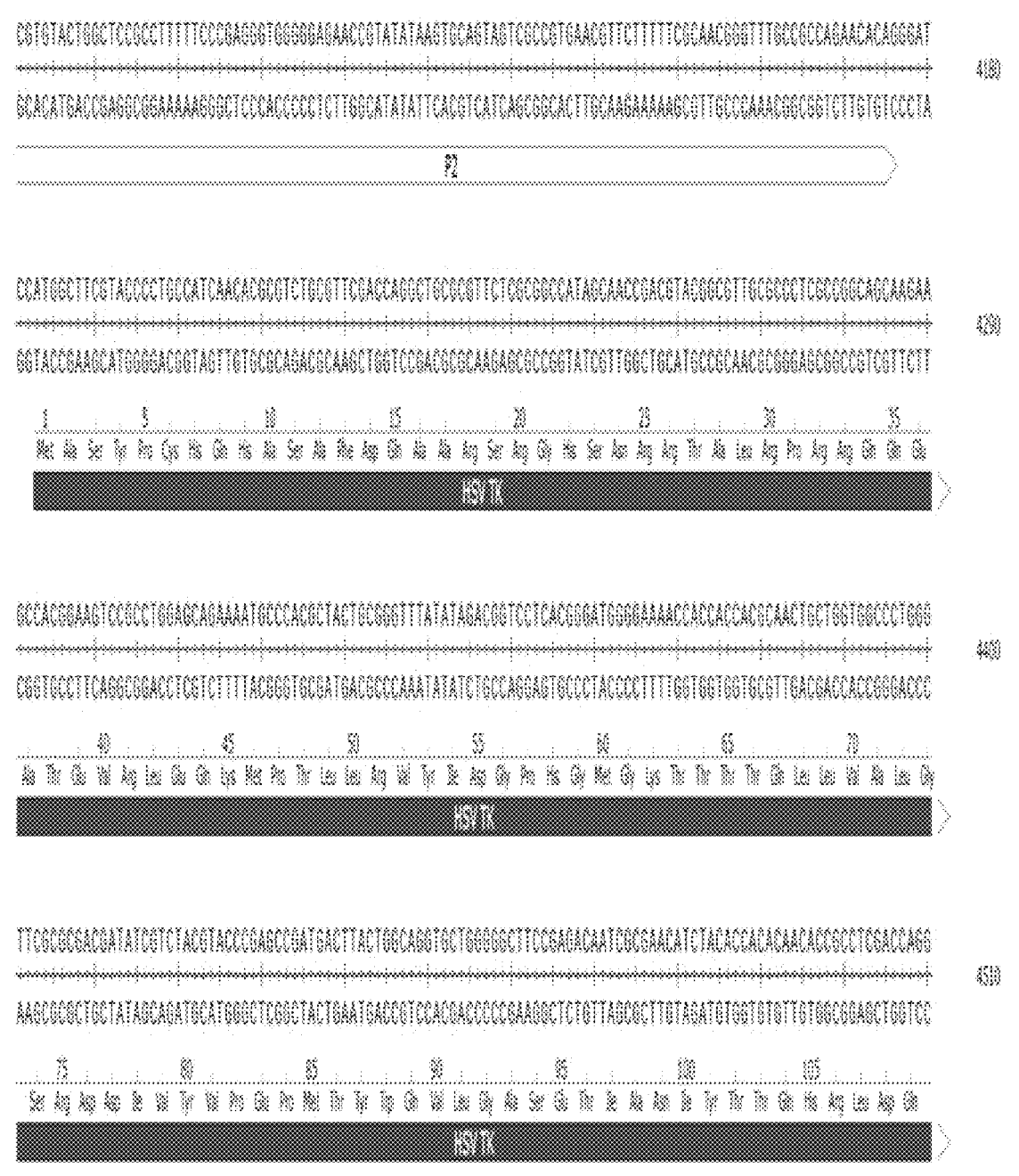
Figure 33J:
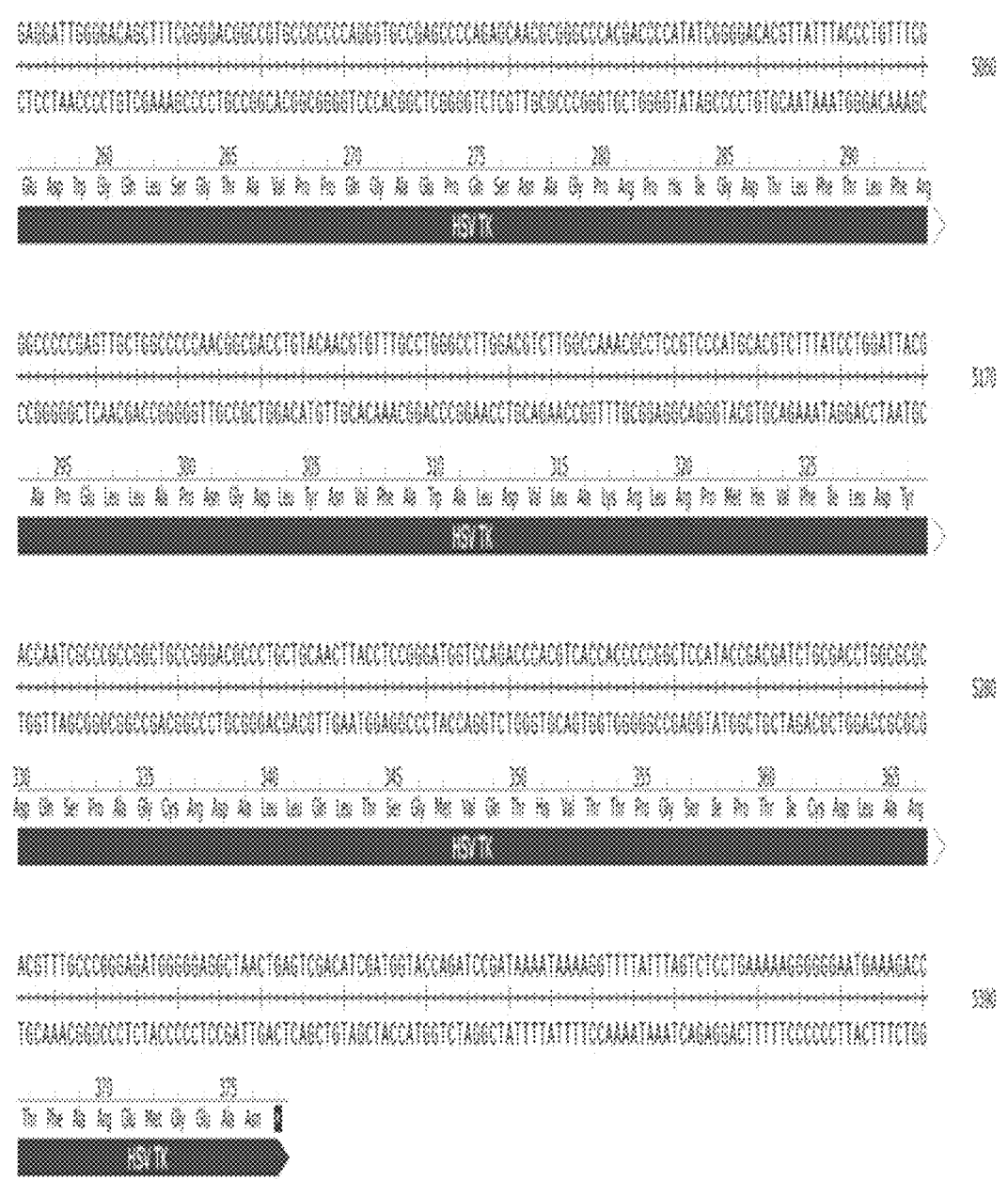
Figure 33K:
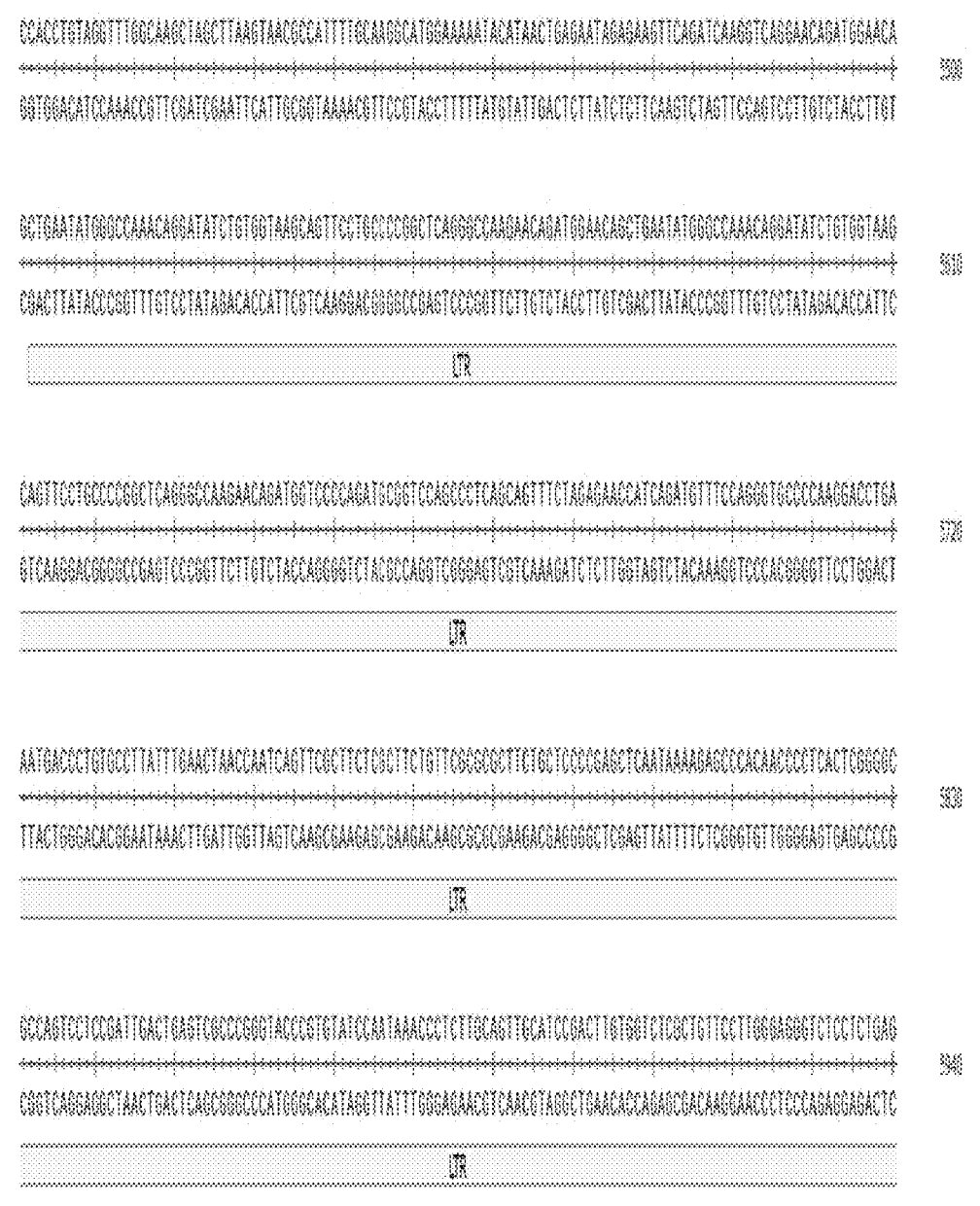
Figure 33M:
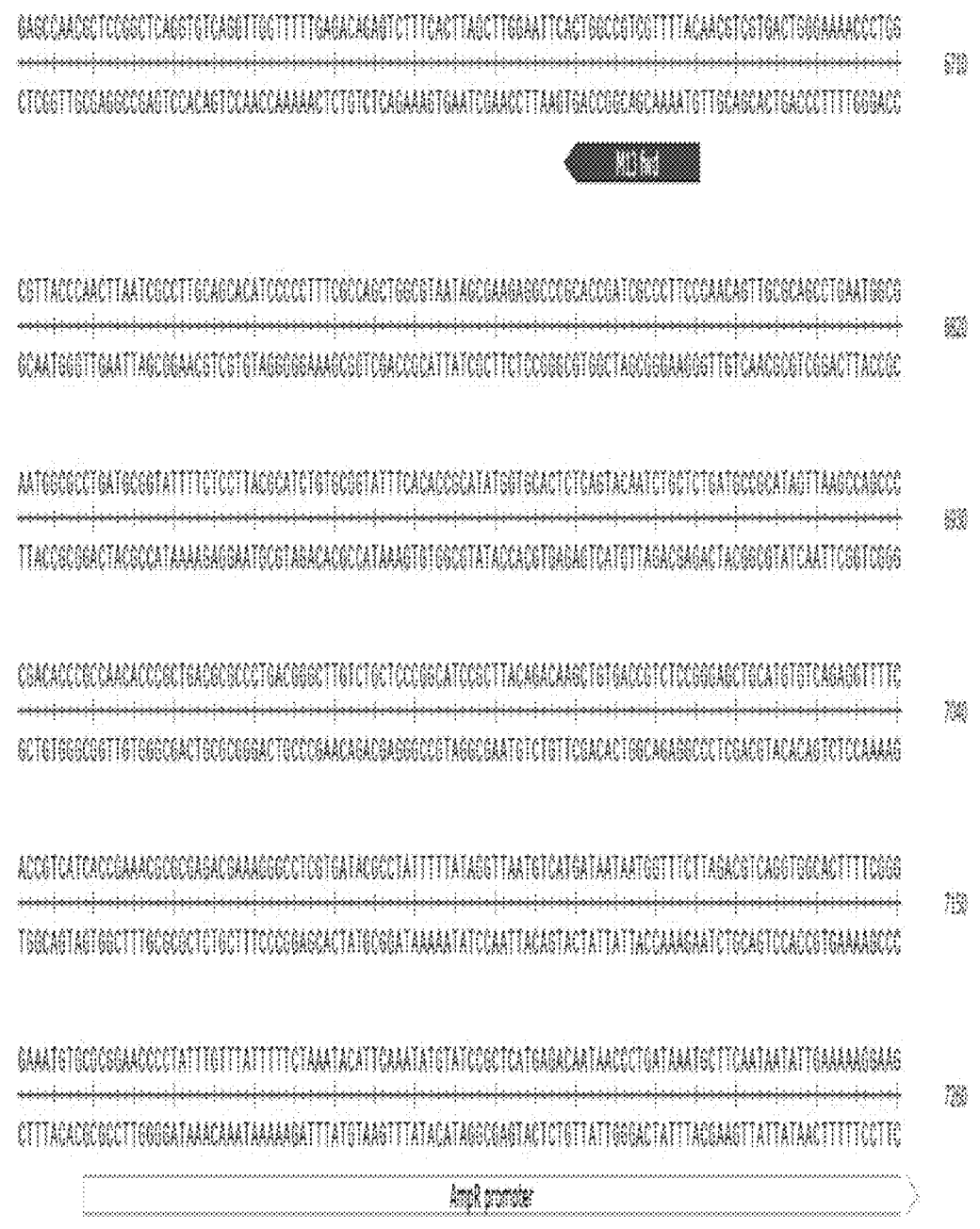
Figure 33O:
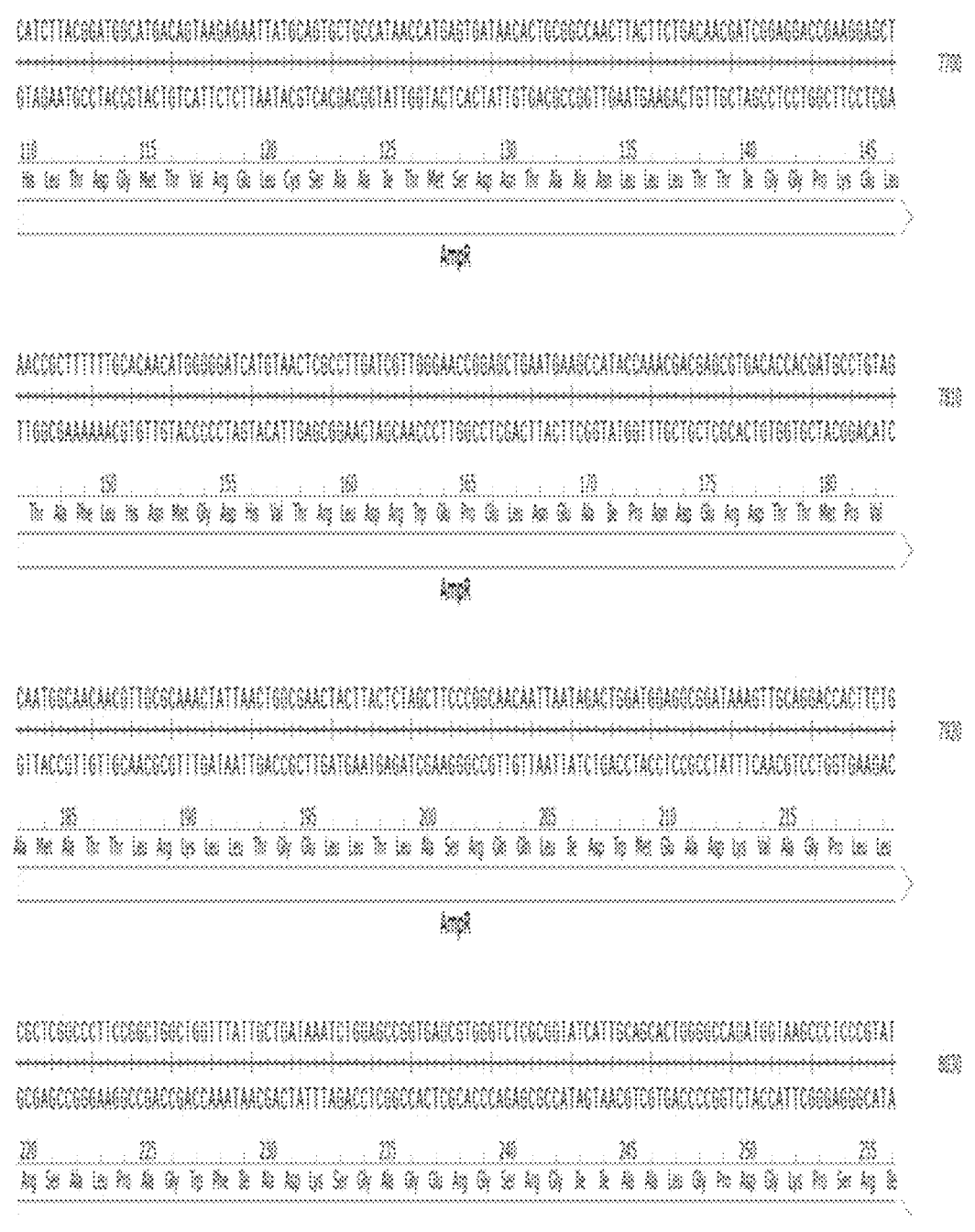
Figure 33P:
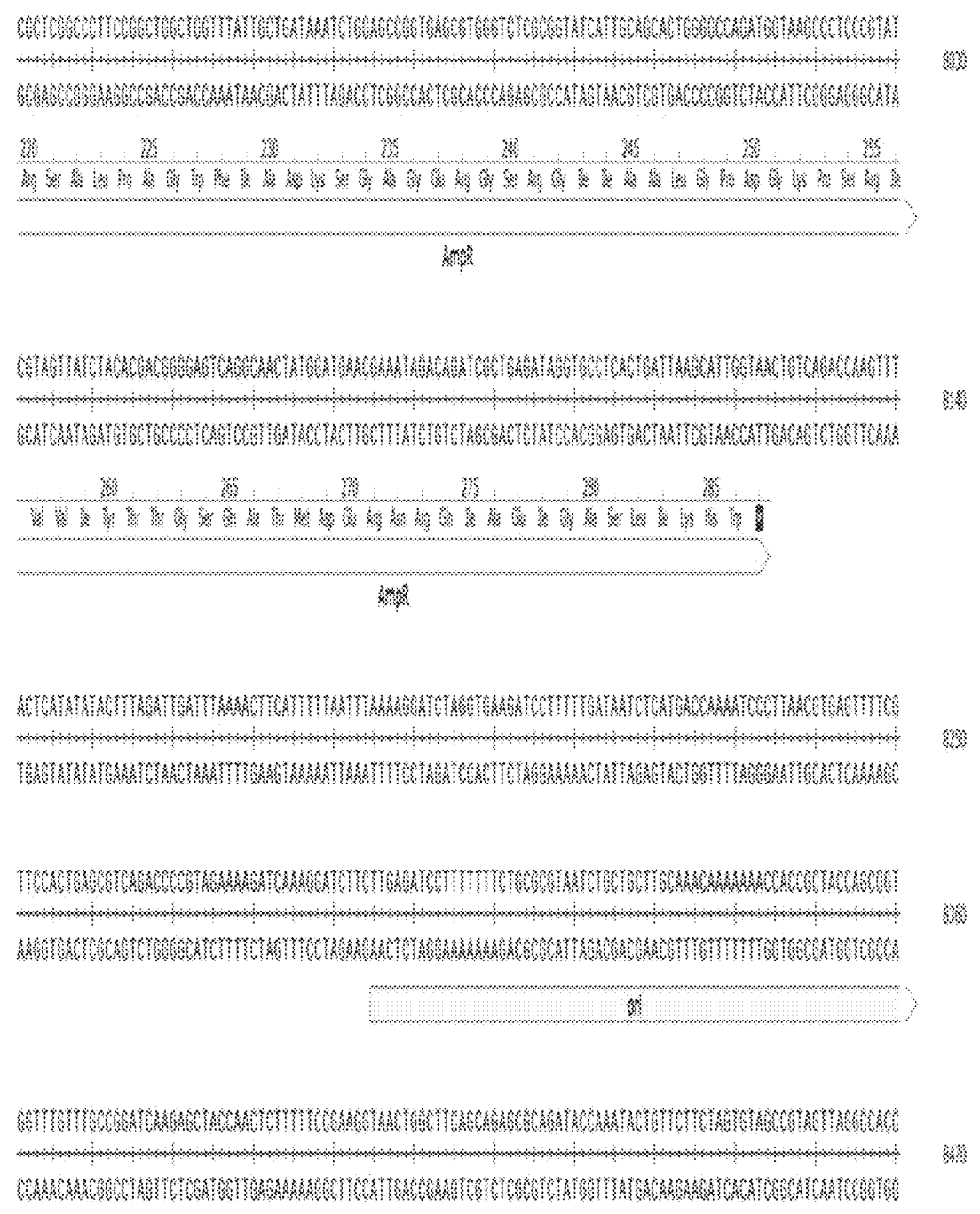
Figure 33Q:
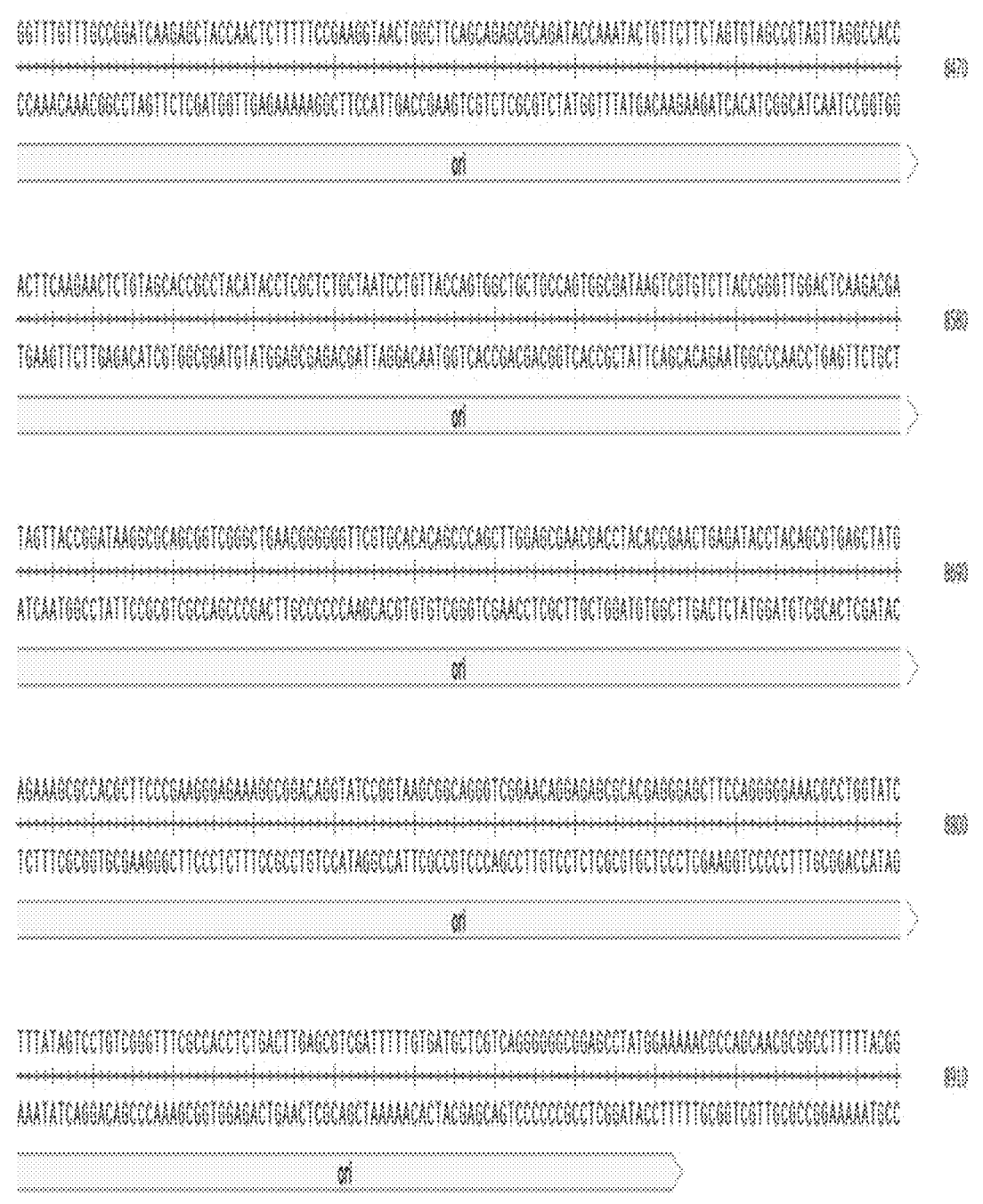
Figure 33R:
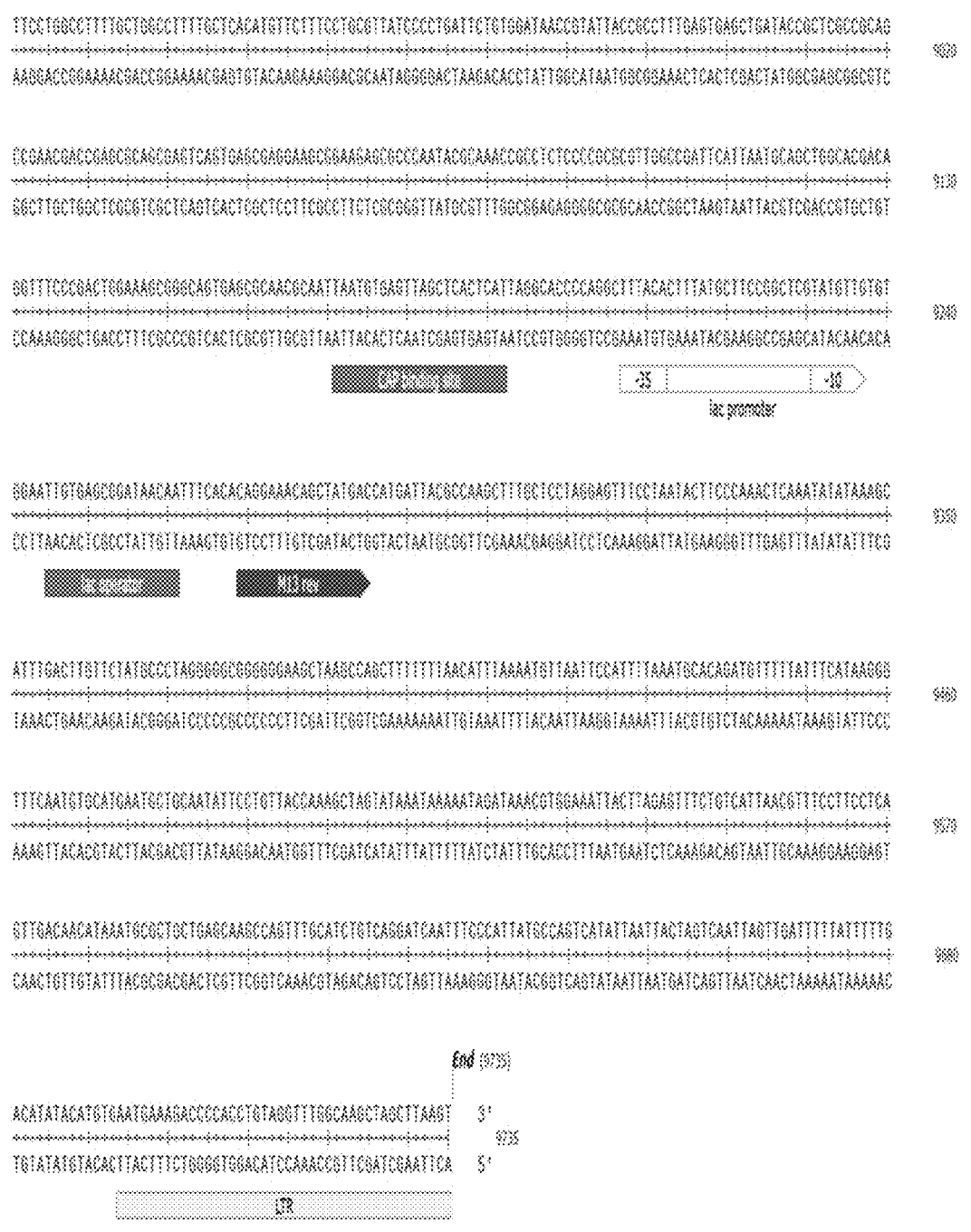

FIG. 33*a* is a diagram illustrating the sequence of spRRVe-P2-TK vector.

FIG. 33*b* is an extension of the diagram illustrating the sequence of spRRVe-P2-TK vector.

FIG. 33*c* is an extension of the diagram illustrating the sequence of spRRVe-P2-TK vector.

FIG. 33*d* is an extension of the diagram illustrating the sequence of spRRVe-P2-TK vector.

FIG. 33*e* is an extension of the diagram illustrating the sequence of spRRVe-P2-TK vector.

FIG. 33*f* is an extension of the diagram illustrating the sequence of spRRVe-P2-TK vector.

FIG. 33*g* is an extension of the diagram illustrating the sequence of spRRVe-P2-TK vector.

FIG. 33*h* is an extension of the diagram illustrating the sequence of spRRVe-P2-TK vector.

FIG. 33*i* is an extension of the diagram illustrating the sequence of spRRVe-P2-TK vector.

FIG. 33*j* is an extension of the diagram illustrating the sequence of spRRVe-P2-TK vector.

FIG. 33*k* is an extension of the diagram illustrating the sequence of spRRVe-P2-TK vector.

FIG. 33*l* is an extension of the diagram illustrating the sequence of spRRVe-P2-TK vector.

FIG. 33*m* is an extension of the diagram illustrating the sequence of spRRVe-P2-TK vector.

FIG. 33*n* is an extension of the diagram illustrating the sequence of spRRVe-P2-TK vector.

FIG. 33*o* is an extension of the diagram illustrating the sequence of spRRVe-P2-TK vector.

FIG. 33*p* is an extension of the diagram illustrating the sequence of spRRVe-P2-TK vector.

FIG. 33*q* is an extension of the diagram illustrating the sequence of spRRVe-P2-TK vector.

FIG. 33*r* is an extension of the diagram illustrating the sequence of spRRVe-P2-TK vector.

FIG. 34 is a schematic diagram illustrating the structure of sRRVgp-P2-CD6 vector.

Figure 35B:
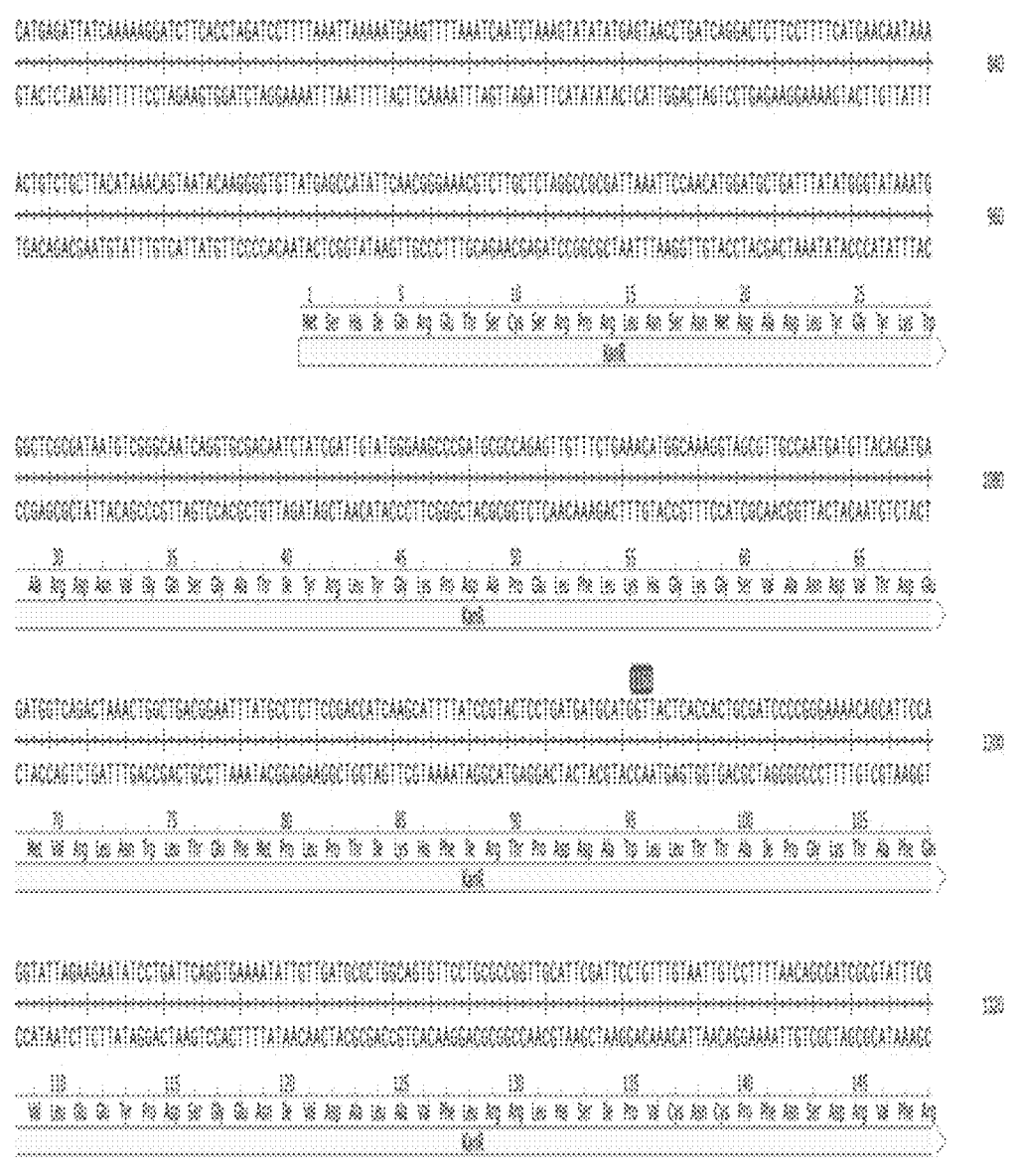
Figure 35C:
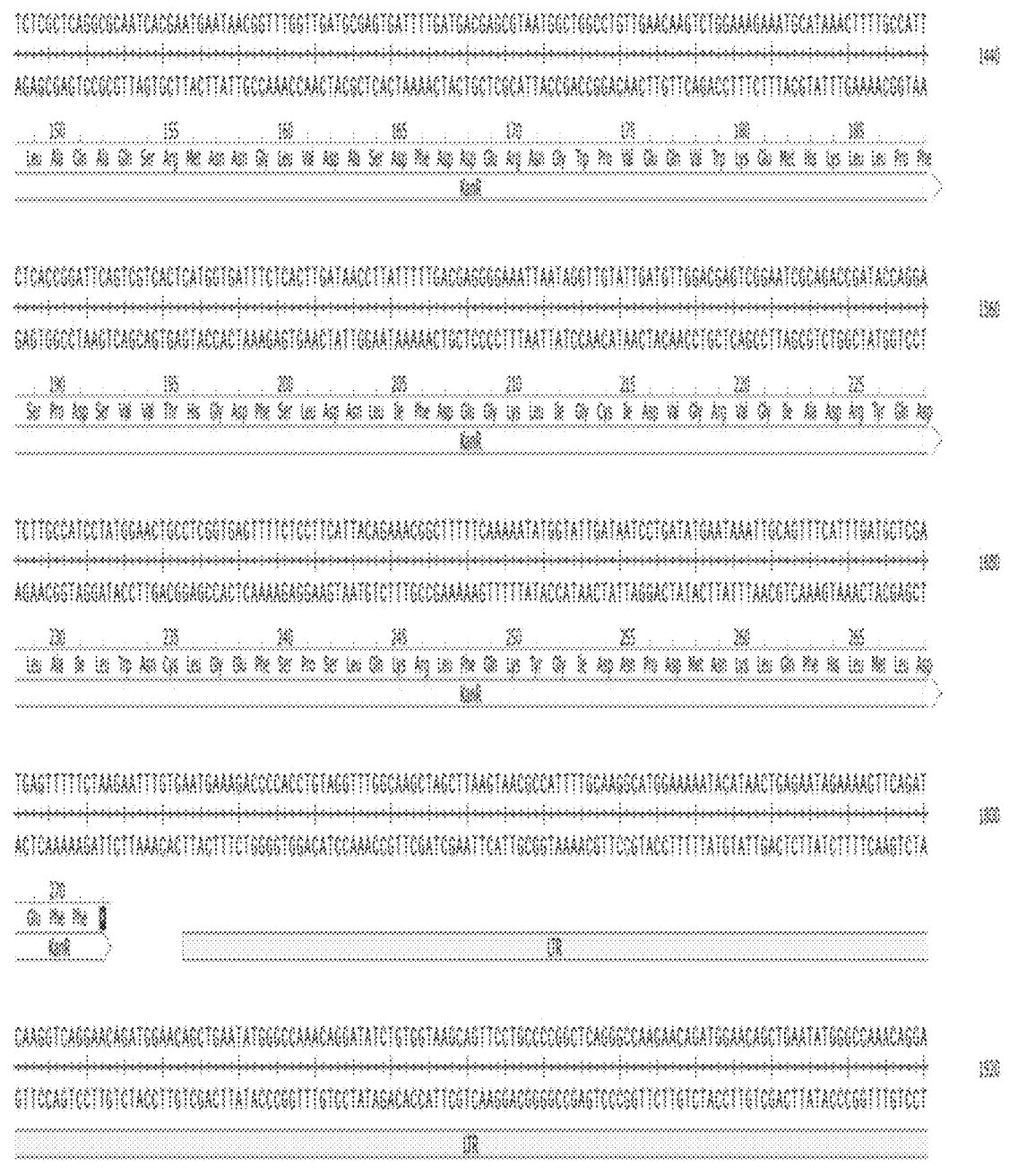
Figure 35E:
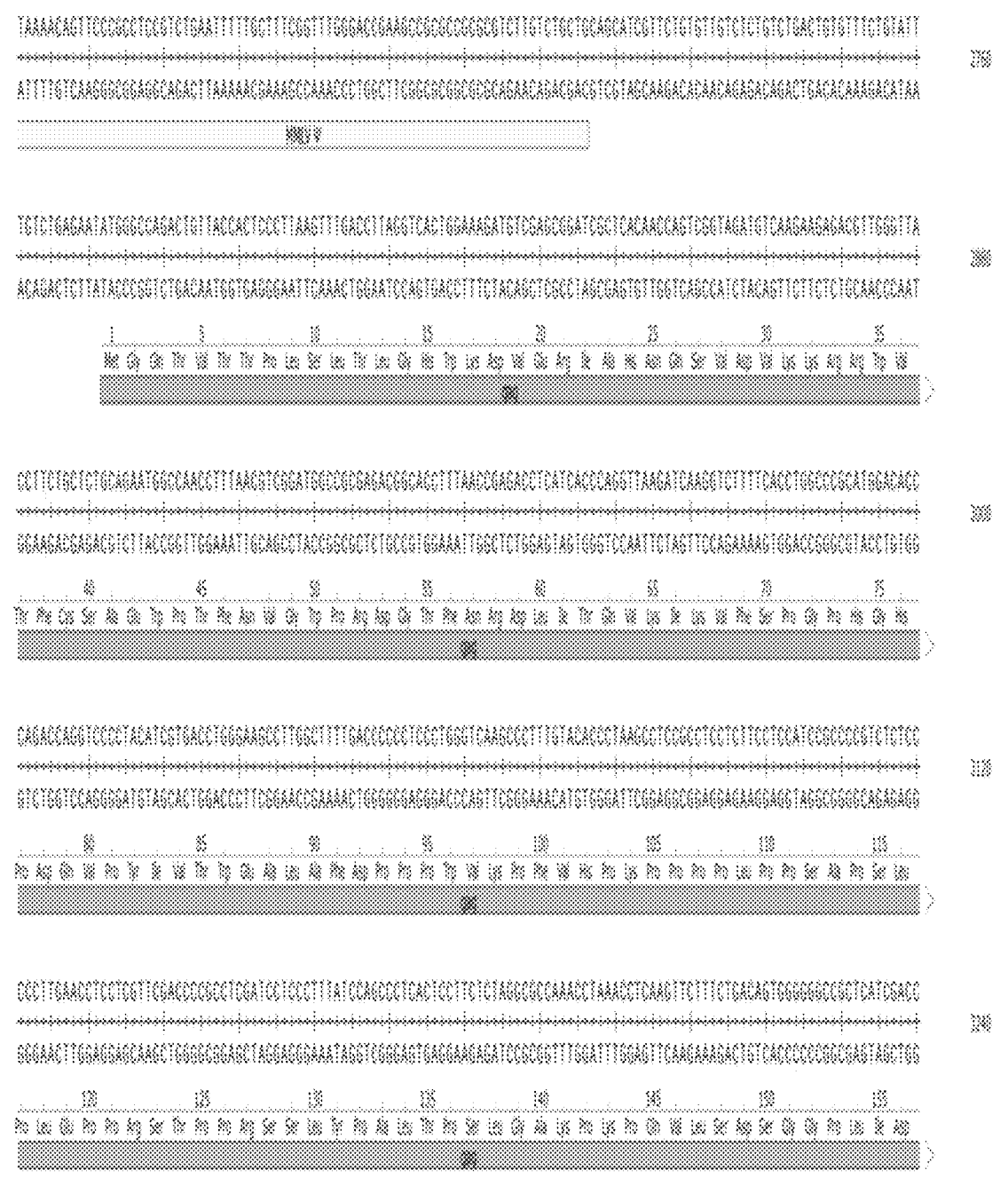
Figure 35F:
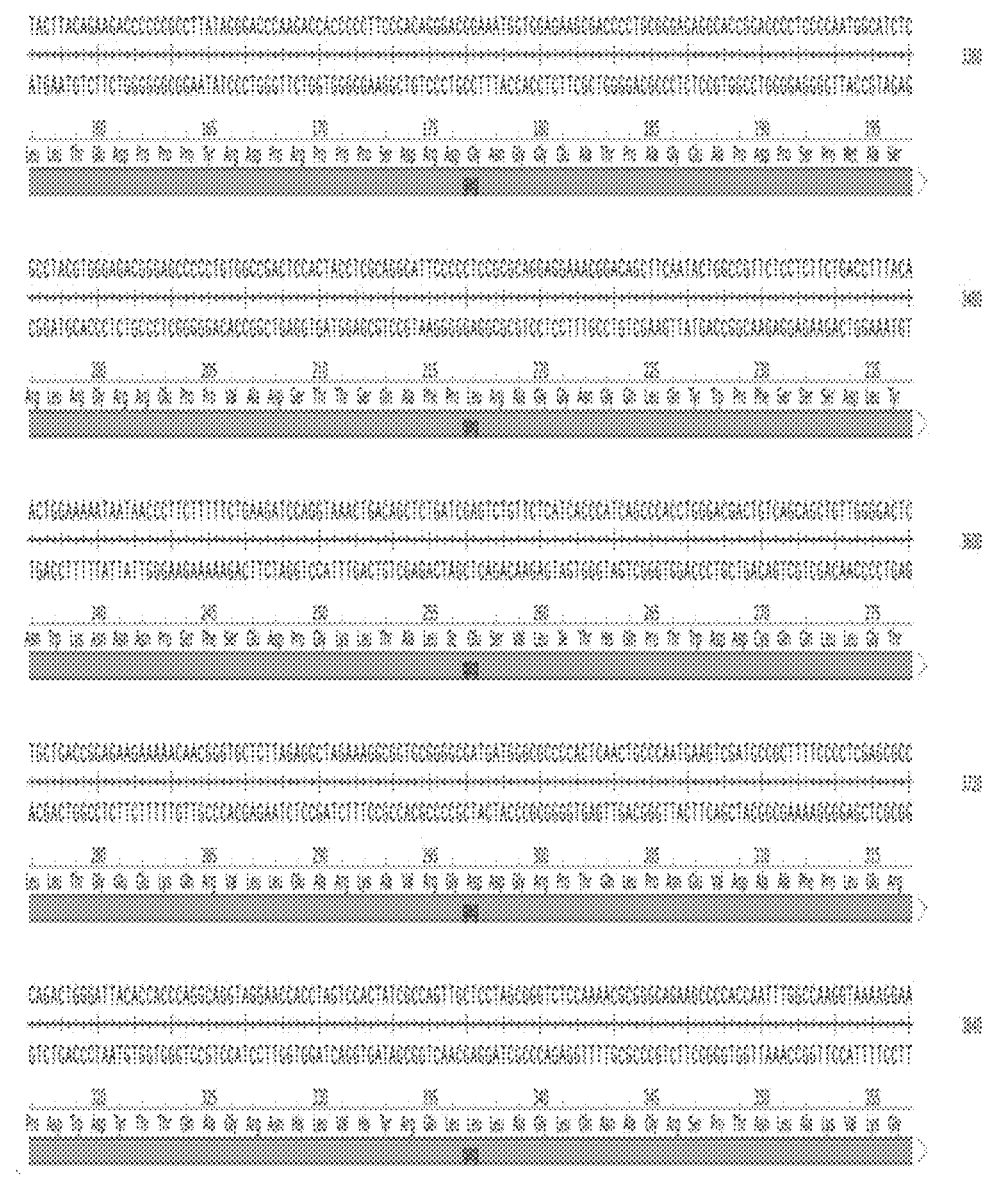
Figure 35G:
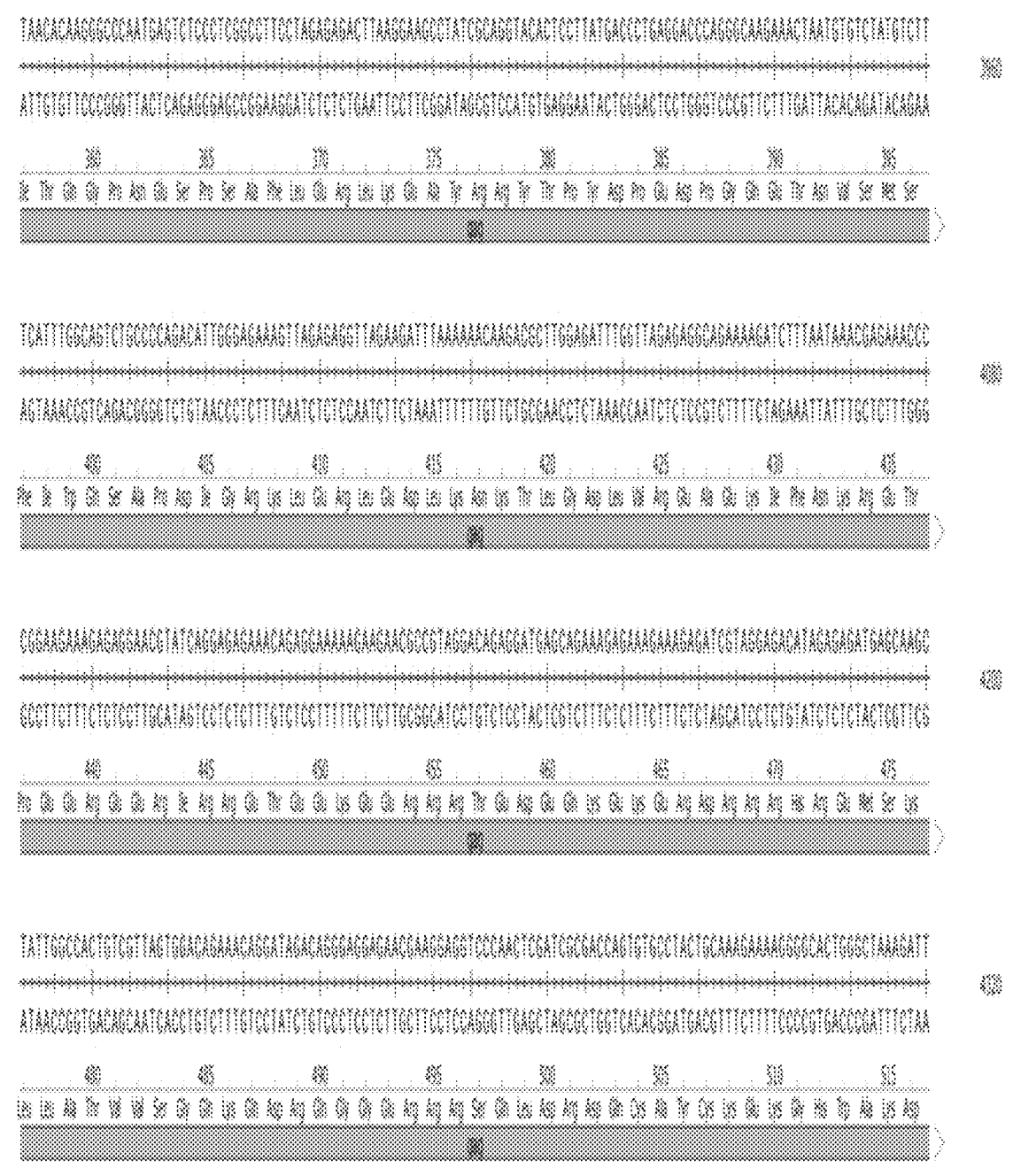
Figure 35H:
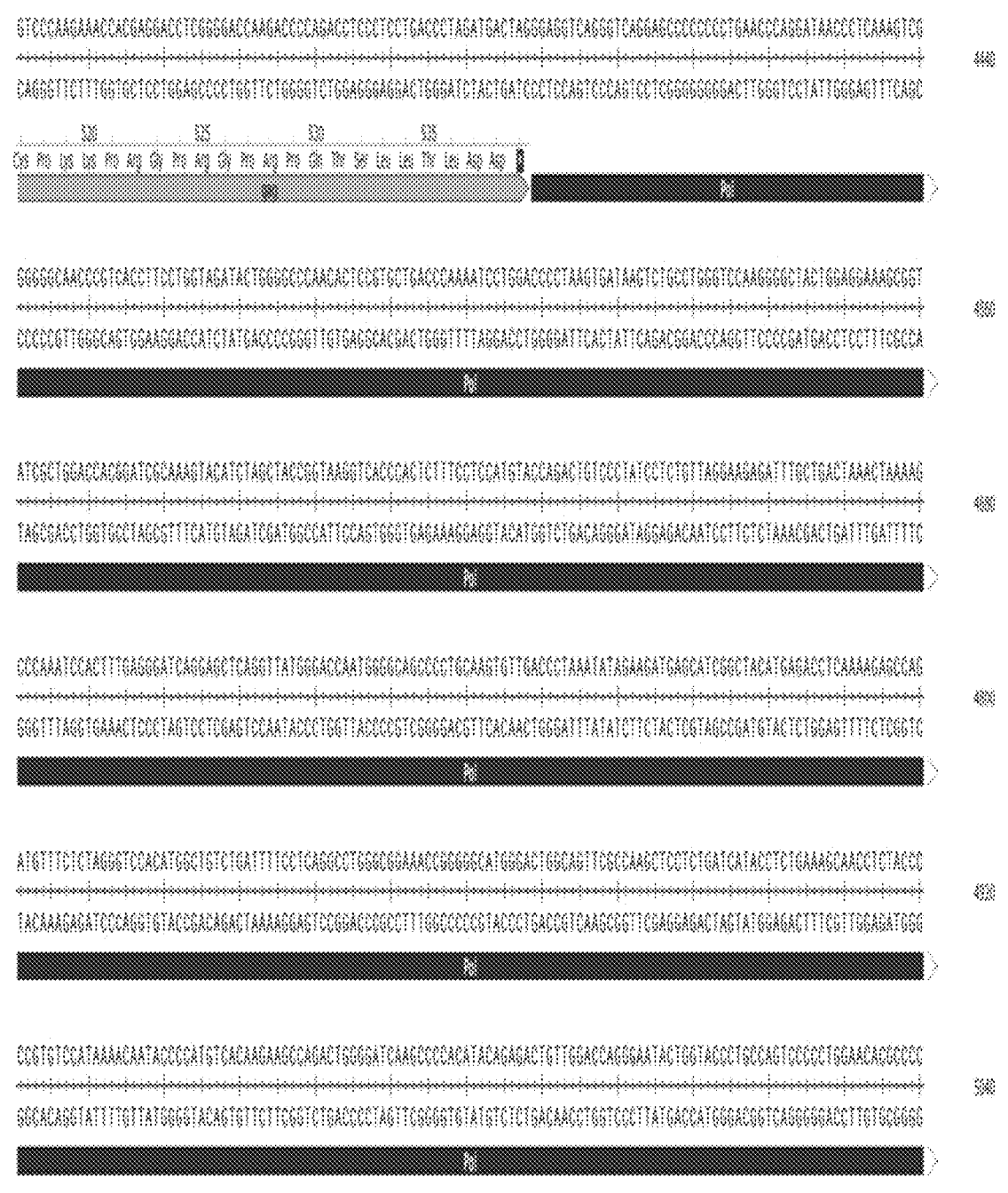
Figure 35J:
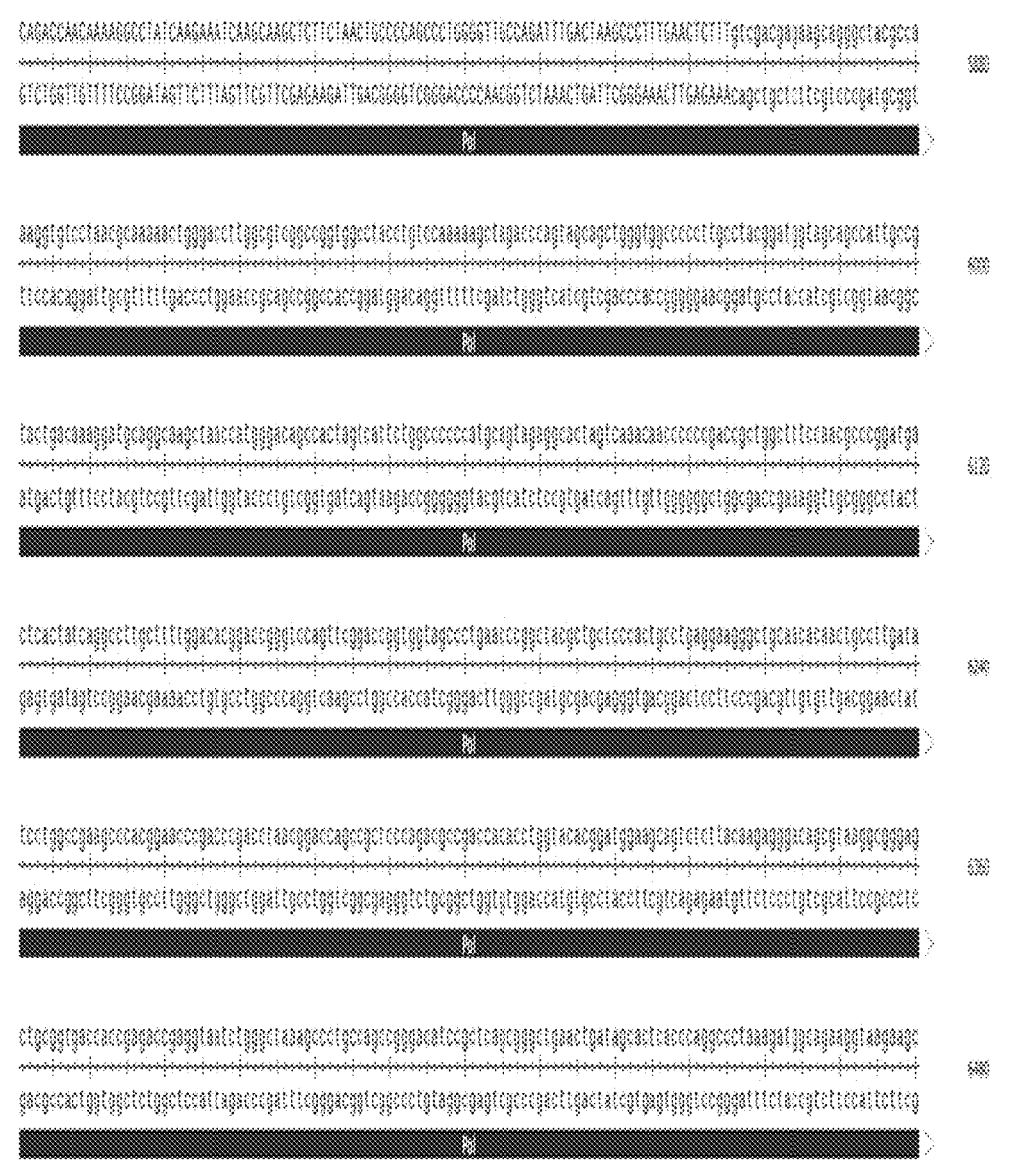
Figure 35K:
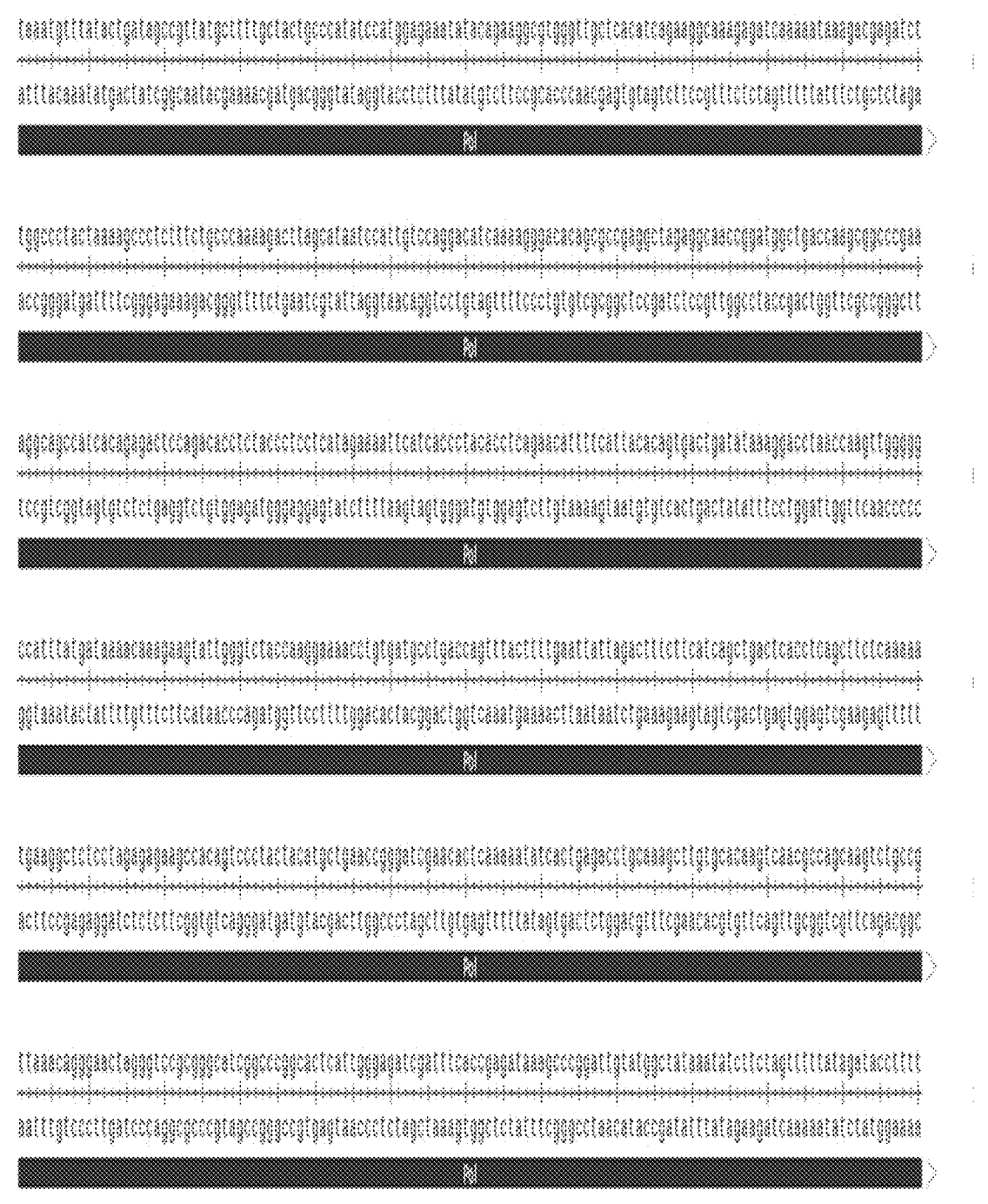
Figure 35M:
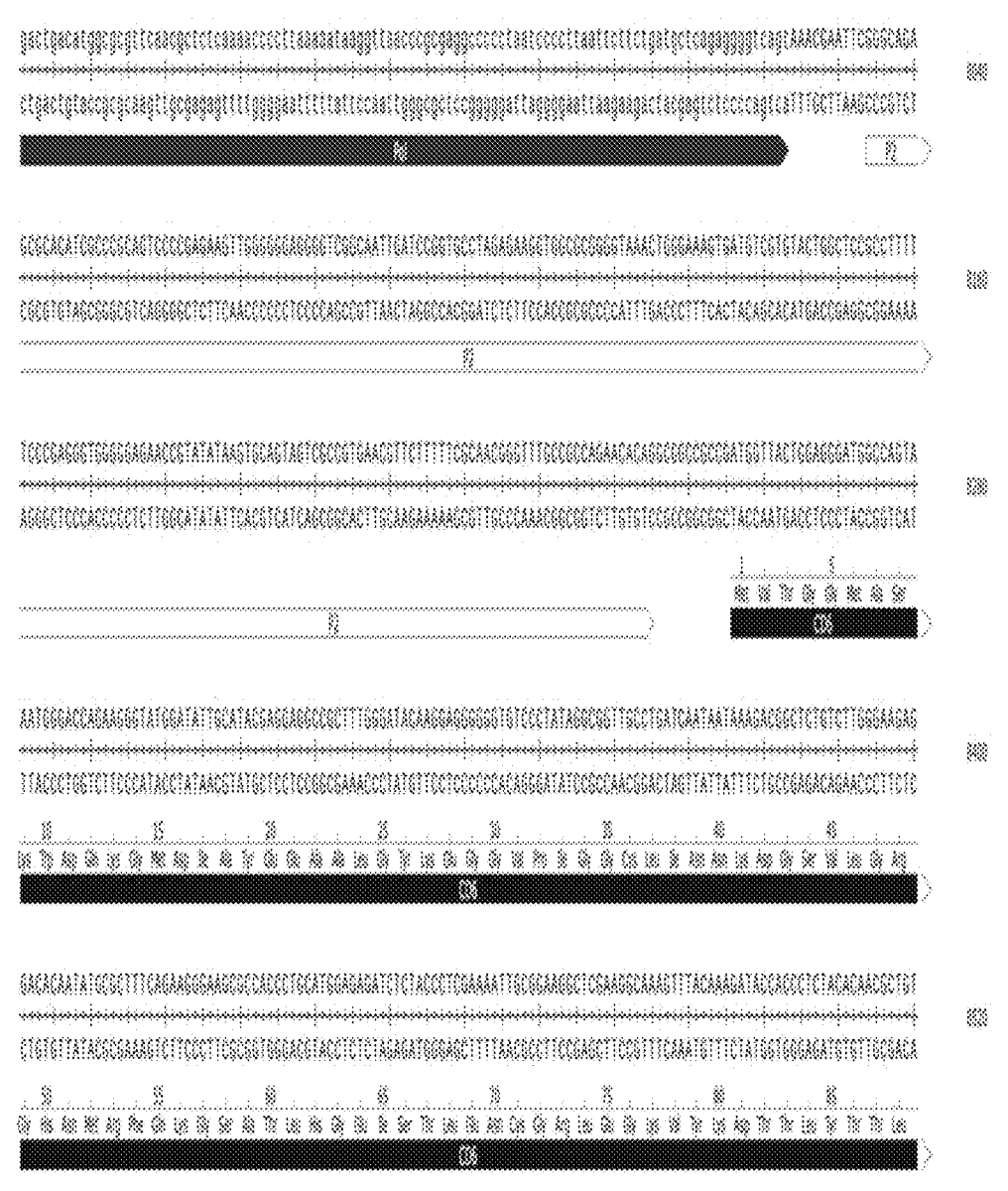

FIG. 35*a* is a diagram illustrating the sequence of sRRVgp-P2-CD6 vector.

FIG. 35*b* is an extension of the diagram illustrating the sequence of sRRVgp-P2-CD6 vector.

FIG. 35*c* is an extension of the diagram illustrating the sequence of sRRVgp-P2-CD6 vector.

FIG. 35*d* is an extension of the diagram illustrating the sequence of sRRVgp-P2-CD6 vector.

FIG. 35*e* is an extension of the diagram illustrating the sequence of sRRVgp-P2-CD6 vector.

FIG. 35*f* is an extension of the diagram illustrating the sequence of sRRVgp-P2-CD6 vector.

FIG. 35*g* is an extension of the diagram illustrating the sequence of sRRVgp-P2-CD6 vector.

FIG. 35*h* is an extension of the diagram illustrating the sequence of sRRVgp-P2-CD6 vector.

FIG. 35*i* is an extension of the diagram illustrating the sequence of sRRVgp-P2-CD6 vector.

FIG. 35*j* is an extension of the diagram illustrating the sequence of sRRVgp-P2-CD6 vector.

FIG. 35*k* is an extension of the diagram illustrating the sequence of sRRVgp-P2-CD6 vector.

FIG. 35*l* is an extension of the diagram illustrating the sequence of sRRVgp-P2-CD6 vector.

FIG. 35*m* is an extension of the diagram illustrating the sequence of sRRVgp-P2-CD6 vector.

FIG. 35*n* is an extension of the diagram illustrating the sequence of sRRVgp-P2-CD6 vector.

FIG. 35*o* is an extension of the diagram illustrating the sequence of sRRVgp-P2-CD6 vector.

FIG. 36*a* is a diagram illustrating whether the recombination occurs or not in spRRVe-P2-TK/sRRVgp-P2-CD2, sRRVgp-P2-CD6, sRRVgp-P2-CD7, or sRRVgp-P2-CD8, confirmed by using GaLV1624F and MFGSacIR primers.

FIG. 36*b* is a diagram illustrating whether the recombination occurs or not in spRRVe-P2-TK/sRRVgp-P2-CD2, sRRVgp-P2-CD6, sRRVgp-P2-CD7, or sRRVgp-P2-CD8, confirmed by using MuLV4194F or MuLV7130F and MFG-SacIR primers.

FIG. 37*a* is a diagram illustrating the drug sensitivity of spRRVe-P2-TK/sRRVgp-P2-CD2, sRRVgp-P2-CD6, sRRVgp-P2-CD7, or sRRVgp-P2-CD8 in the phases of p1 and p2.

FIG. 37*b* is a diagram illustrating the drug sensitivity of spRRVe-P2-TK/sRRVgp-P2-CD2, sRRVgp-P2-CD6, sRRVgp-P2-CD7, or sRRVgp-P2-CD8 in the phases of p3 and p4.

FIG. 37*c* is a diagram illustrating the drug sensitivity of spRRVe-P2-TK/sRRVgp-P2-CD2, sRRVgp-P2-CD6, sRRVgp-P2-CD7, or sRRVgp-P2-CD8 in the phases of p5, p6, and p7.

DESCRIPTION OF THE PREFERRED EMBODIMENTS

The present invention provides a replicating retrovirus vector system comprising the first recombinant expression vector containing MuLV Gag-Pol gene, promoter, and cytosine deaminase gene; and the second recombinant expression vector containing virus Env gene, promoter, and thymidine kinase gene.

The thymidine kinase gene herein can be a polynucleotide composed of the nucleotide sequence represented by SEQ. ID. NO: 15. The polynucleotide above is not only the polynucleotide encoding the amino acid sequence of thymidine kinase but also the polynucleotide having the nucleotide sequence which is actually same as the said polynucleotide and a fragment thereof. The polynucleotide which is composed of the same nucleotide sequence as the above can have at least 80%, preferably at least 90%, and more preferably at least 95% homology with the polynucleotide of the invention. As described hereinbefore, the polynucleotide of the invention can have substitution, deletion, or insertion of one or more nucleotides in the sequence, as long as the polynucleotide can encode a protein having the equal activity to the above.

The cytosine deaminase gene above can be optimized by human codon.

The term "optimized by human codon" herein indicates that a codon preferred by a host that designates an amino acid when DNA in the host cell is transcribed and translated is substituted with a human codon so as to increase the expression efficiency of the amino acid or the protein encoded by the nucleic acid.

The cytosine deaminase gene can be the polynucleotide selected from the group consisting of those polynucleotides respectively composed of the sequence represented by SEQ. ID. NO: 16, the sequence represented by SEQ. ID. NO: 17, the sequence represented by SEQ. ID. NO: 18, the sequence represented by SEQ. ID. NO: 19, the sequence represented by SEQ. ID. NO: 20, the sequence represented by SEQ. ID. NO: 21, the sequence represented by SEQ. ID. NO: 22, the sequence represented by SEQ. ID. NO: 23, the sequence represented by SEQ. ID. NO: 24, the sequence represented by SEQ. ID. NO: 25, the sequence represented by SEQ. ID. NO: 26, the sequence represented by SEQ. ID. NO: 27, the sequence represented by SEQ. ID. NO: 28, the sequence represented by SEQ. ID. NO: 29, the sequence represented by SEQ. ID. NO: 30, and the sequence represented by SEQ. ID. NO:31. The polynucleotide can include a variant having the same characteristics as the above.

The thymidine kinase or cytosine deaminase gene can activate a prodrug. The prodrug can be one or more drugs selected from the group consisting of ganciclovir and 5-fluorocytosine. In a preferred embodiment of the present invention, the thymidine kinase gene can activate ganciclovir, and the cytosine deaminase gene can active 5-fluorocytosine.

The said Gag gene can be the polynucleotide encoding kinds of proteins that form the retrovirus core. In the meantime, the Pol gene can be the polynucleotide encoding the retrovirus reverse transcriptase and the Env gene can be the polynucleotide encoding the retrovirus envelope glycoprotein.

The said MuLV-Gag gene is the Gag gene of murine leukemia virus, which can be the polynucleotide composed of the nucleotide sequence represented by SEQ. ID. NO: 32. The said MuLV-Pol gene is the Pol gene of murine leukemia virus, which can be the polynucleotide composed of the nucleotide sequence represented by SEQ. ID. NO: 33. The MuLV Gag-Pol gene can be the polynucleotide composed of the fusion sequence comprising the nucleotide sequence represented by SEQ. ID. NO: 32 and the nucleotide sequence represented by SEQ. ID. NO: 33.

The promoter above can be one of the promoters originated from cancer specific promoters such as MCMV immediate-early promoter, EF1α promoter, HCMV immediate-early promoter, PGK promoter, and hTERT promoter. Herein, the said EF1α promoter can be the polynucleotide composed of the nucleotide sequence represented by SEQ. ID. NO: 34.

The said Env gene can be selected from the group consisting of those Env genes of gibbon ape leukemia virus (GaLV), amphotropic MuLV, xenotropic MuLV, RD114, vesicular stomatitis virus (VSV), and measles virus (MV). The Env gene of gibbon ape leukemia virus can be the polynucleotide composed of the nucleotide sequence represented by SEQ. ID. NO: 35. The said polynucleotide can include a variant having the same characteristics as mentioned above.

In this invention, the term "replicating/replicable" indicates that the virus vector can self-replicate in the cells introduced with the virus genome containing a specific gene or infected with animal cells or the virus vector containing a specific gene.

In this invention, the term "replicating retrovirus vector" indicates the vector that produces non-lytic virus. The vector can specifically infect proliferating cells, that is cancer cells, because it can penetrate into the nucleus when the nuclear envelope is being broken, so that it can prevent an inserted foreign gene from being expressed in other normal cells. Therefore, the vector can deliver a target gene safely into cancer cells and is also replicating to increase the efficiency of gene transfer.

In one embodiment of the present invention, the inventors separated MuLV-Gag gene and MuLV-Pol gene and GalV-EnV gene in order to express them separately in each vector. The inventors cloned P2 promoter and cytosine deaminase gene in the vector containing Gag and Pol genes. The inventors further cloned P2 promoter and thymidine kinase gene in the vector containing Env gene, leading to the construction of the replicating retrovirus vector (see FIG. 31). The present inventors lastly confirmed that the recombination did not occur in those vectors (see FIGS. 36a and 36b).

Therefore, the present invention also provides a replicating retrovirus vector system comprising the first recombinant expression vector containing MuLV Gag-Pol gene, promoter, and thymidine kinase gene; and the second recombinant expression vector containing virus Env gene, promoter, and cytosine deaminase gene.

The said vector system has the characteristics explained above. For example, the thymidine kinase gene can activate the prodrug ganciclovir, and the cytosine deaminase gene can active the prodrug 5-fluorocytosine.

In one embodiment of the present invention, the inventors separated MuLV-Gag gene and MuLV-Pol gene, and GalV-EnV gene in order to express them separately in each vector. The inventors cloned P2 promoter and thymidine kinase gene in the vector containing Gag and Pol genes. The inventors further cloned P2 promoter and cytosine deaminase gene in the vector containing Env gene, leading to the construction of the replicating retrovirus vector (see FIG. 25).

Therefore, the present invention also provides a recombinant retrovirus containing the vector system above.

The vector system can have the characteristics mentioned above.

However, the recombinant retrovirus above can be produced from the first recombinant expression vector comprising MuLV Gag-Pol gene, promoter, and cytosine deaminase gene; and the second recombinant expression vector comprising virus Env gene, promoter, and thymidine kinase gene. At this time, the first and the second recombinant expression vectors can be included in the recombinant retrovirus independently or together.

In a preferred embodiment of the present invention, the inventors separated MuLV-Gag gene and MuLV-Pol gene, and GalV-EnV gene in order to express them respectively in each vector, and cloned P2 promoter and cytosine deaminase gene in the vector containing Gag and Pol genes. The inventors also cloned P2 promoter and thymidine kinase gene in the vector containing Env gene, leading to the construction of the replicating retrovirus vector (see FIG. 31). The present inventors also produced virus with the said vector.

Therefore, the present invention also provides a host cell transfected with the recombinant retrovirus.

The vector system above can have the characteristics mentioned above.

The host cell herein can be selected from the group consisting of NS/0 myeloma cell, human 293T cell, CHO cell, HeLa cell, CapT cell (human amniotic fluid derived cell), COS cell, canine D17 cell, and feline PG4 cell. In a preferred embodiment of the present invention, the host cell can be human 293T.

The said transfection can be performed by one of the conventional methods well-known to those in the art, which is exemplified by lipofectamine method, microinjection, calcium phosphate precipitation, electroporation, liposome-mediated transfection, DEAE-dextran treatment, and gene bombardment. In a preferred embodiment of the present invention, the transfection was accomplished by lipofectamine method.

The transfected cells were cultured in the conventional medium generally used for animal cell culture. The medium above can be one or more media selected from the group consisting of Eagle's MEM, a-MEM, Iscove's MEM, 199 medium, CMRL 1066, RPMI 1640, F12, F10, DMEM, DMEM/F12 combined medium, Way-mouth's MB752/1, McCoy's 5A, and MCDB series media. In a preferred embodiment of the present invention, the medium was DMEM.

In one embodiment of the present invention, the inventors separated MuLV-Gag gene and MuLV-Pol gene, and GalV-EnV gene in order to express them separately in each vector. The inventors cloned P2 promoter and cytosine deaminase gene in the vector containing Gag and Pol genes. The inventors further cloned P2 promoter and thymidine kinase gene in the vector containing Env gene, leading to the construction of the replicating retrovirus vector (see FIG. 31). The present inventors lastly confirmed that the recombination did not occur in those vectors (see FIGS. 36a and 36b).

Therefore, the present invention also provides a pharmaceutical composition for the prevention or treatment of cancer comprising the recombinant retrovirus above as an active ingredient.

However, the recombinant retrovirus above can be produced from the first recombinant expression vector comprising MuLV Gag-Pol gene, promoter, and cytosine deaminase gene; and the second recombinant expression vector comprising virus Env gene, promoter, and thymidine kinase gene. At this time, the first and the second recombinant expression vectors can be included in the recombinant retrovirus independently or together.

The retrovirus above can target the cell in the course of proliferation which is more precisely cancer cell. The cancer cell herein can include those cells originated from one of the followings; mucous carcinoma, round cell carcinoma, locally advanced tumor, metastatic cancer, Ewing sarcoma, cancer metastasis, lymphatic metastasis, squaous cell carcinoma, esophageal squaous cell carcinoma, oral carcinoma, multiple myeloma, acute lymphoblastic leukemia, acute nonlymphoid leukemia, chronic lymphocytic leukemia, chronic myeloid leukemia, hairy cell leukemia, effusion lymphoma, thymus lymphoma lung cancer, small cell lung cancer, cutaneous T cell lymphoma, Hodgkin's lymphoma, non-Hodgkin's lymphoma, adrenal cortical carcinoma, ACTH-producing tumor, non-small cell lung cancer, breast cancer, small cell carcinoma, ductal carcinoma, stomach cancer, colon cancer, colorectal cancer, polyp related to colorectal cancer formation, pancreatic cancer, liver cancer, bladder cancer, primary surface bladder tumor, invasive metastatic cell bladder carcinoma, muscle-invasive bladder cancer, prostate cancer, colon cancer, kidney cancer, hepatocarcinoma, esophageal cancer, ovarian carcinoma, uterine cervical cancer, endometrial cancer, choriocarcinoma, ovarian cancer, primary peritoneum neoplasm, uterine cervical carcinoma, vaginal cancer, pudendum cancer, uterine cancer, follicle solid tumor, testis cancer, penis cancer, renal cell carcinoma, brain cancer, head/neck cancer, neuroblastoma, brainstem glioma, glioma, metastatic tumor cell invasion in central nervous system, osteoma, osteosarcoma, malignant melanoma, human skin keratinocyte tumor progression, squaous cell carcinoma, thyroid cancer, retinoblastoma, neuroblastoma, mesothelioma, Wilm's tumor, gallbladder cancer, trophoblastic tumor, hemangiopericytoma, and Kaposi's sarcoma.

In one embodiment of the present invention, the inventors separated MuLV-Gag gene and MuLV-Pol gene, and GalV-EnV gene in order to express them respectively in each vector, and cloned P2 promoter and cytosine deaminase gene in the vector containing Gag and Pol genes. The inventors also cloned P2 promoter and thymidine kinase gene in the vector containing Env gene, leading to the construction of the replicating retrovirus vector (see FIG. 31). The present inventors also confirmed that the said vector had excellent drug sensitivity against ganciclovir and 5-fluorocytosine (see FIGS. 37a, 37b, and 37c).

The pharmaceutical composition of the present invention preferably includes the composition of the invention, which is the active ingredient of the pharmaceutical composition, by 10~95 weight % for the total weight of the pharmaceutical composition. The composition of the present invention can include, in addition to the active ingredient, one or more effective ingredients having the same or similar function to the active ingredient.

The composition of the present invention can include any generally used carrier, diluent, excipient, or a combination of at least two of those. The pharmaceutically acceptable carrier can be any carrier that is able to deliver the composition of the present invention in living body without limitation, which is exemplified by the compounds described in Merck Index, 13th ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added.

The present composition can be formulated by using generally used excipients or diluents such as fillers, extenders, binders, wetting agents, disintegrating agents and surfactants.

The composition of the present invention can be formulated for oral administration or for parenteral administration. The formulation for oral administration is exemplified by tablets, pills, powders, granules, capsules, and troches. The solid formulations for oral administration are prepared by mixing one or more suitable excipients such as starch, calcium carbonate, sucrose, lactose, and gelatin, etc. Except for the simple excipients, lubricants, for example magnesium stearate, talc, etc, can be added. Liquid formulations for oral administrations are suspensions, solutions, emulsions and syrups, and the above-mentioned formulations can contain various excipients such as wetting agents, sweeteners, aromatics and preservatives.

Formulations for parenteral administration can include injections such as sterilized aqueous solutions, water-insoluble excipients, suspensions, and emulsions.

Water insoluble excipients and suspensions can contain propylene glycol, polyethylene glycol, vegetable oil like olive oil, injectable ester like ethylolate, etc.

Therefore, the present invention also provides a composition for gene transfer for the treatment of cancer comprising the recombinant retrovirus above.

However, the recombinant retrovirus above can be produced from the first recombinant expression vector comprising MuLV Gag-Pol gene, promoter, and cytosine deaminase gene; and the second recombinant expression vector comprising virus Env gene, promoter, and thymidine kinase gene. At this time, the first and the second recombinant expression vectors can be included in the recombinant retrovirus independently or together.

The cancer herein can include the cancers described hereinbefore.

In this invention, the term "composition for gene transfer" indicates the composition that can carry a gene into a target cell.

In one embodiment of the present invention, the inventors separated MuLV-Gag gene and MuLV-Pol gene, and GalV-EnV gene in order to express them respectively in each vector, and cloned P2 promoter and cytosine deaminase gene in the vector containing Gag and Pol genes. The inventors also cloned P2 promoter and thymidine kinase gene in the vector containing Env gene, leading to the construction of the replicating retrovirus vector (see FIG. 31). The present inventors also confirmed that the said vector had excellent drug sensitivity against ganciclovir and 5-fluorocytosine (see FIGS. 37a, 37b, and 37c).

Therefore, the present invention also provides a method for preparing a replicating retrovirus vector system comprising the following steps: 1) constructing the first recombinant expression vector comprising MuLV Gag-Pol gene, promoter, and cytosine deaminase gene; and 2) constructing the second recombinant expression vector comprising virus Env gene, promoter, and thymidine kinase gene.

The vector system above has the characteristics mentioned above. For example, the thymidine kinase gene can activate the prodrug ganciclovir and the cytosine deaminase gene can activate the prodrug 5-fluorocytosine.

In one embodiment of the present invention, the inventors separated MuLV-Gag gene and MuLV-Pol gene, and GalV-EnV gene in order to express them separately in each vector. The inventors cloned P2 promoter and cytosine deaminase gene in the vector containing Gag and Pol genes. The inventors further cloned P2 promoter and thymidine kinase gene in the vector containing Env gene, leading to the construction of the replicating retrovirus vector (see FIG. 31). The present inventors also confirmed that the recombination did not occur in those vectors (see FIGS. 36a and 36b).

Therefore, the present invention also provides a method for preparing a replicating retrovirus vector system comprising the following steps: 1) constructing the first recombinant expression vector comprising MuLV Gag-Pol gene, promoter, and thymidine kinase gene; and 2) constructing the second recombinant expression vector comprising virus Env gene, promoter, and cytosine deaminase gene.

The vector system above has the characteristics mentioned above. For example, the thymidine kinase gene can activate the prodrug ganciclovir and the cytosine deaminase gene can activate the prodrug 5-fluorocytosine.

In one embodiment of the present invention, the inventors separated MuLV-Gag gene and MuLV-Pol gene, and GalV-EnV gene in order to express them separately in each vector. The inventors cloned P2 promoter and thymidine kinase gene in the vector containing Gag and Pol genes. The inventors further cloned P2 promoter and cytosine deaminase gene in the vector containing Env gene, leading to the construction of the replicating retrovirus vector (see FIG. 25).

Therefore, the present invention also provides a method for treating cancer containing the step of administering the recombinant retrovirus above to a subject in need of the same.

The cancer can have the characteristics mentioned above. The subject can be mammals, and more specifically can be human. However, the recombinant retrovirus above can be produced from the first recombinant expression vector comprising MuLV Gag-Pol gene, promoter, and cytosine deaminase gene; and the second recombinant expression vector comprising virus Env gene, promoter, and thymidine kinase gene. At this time, the first and the second recombinant expression vectors can be included in the recombinant retrovirus independently or together.

The recombinant retrovirus of the present invention can be administered via oral administration or parenteral administration according to the purpose of the administration and parenteral administration pathway can be selected from the group consisting of skin external application, intraperitoneal injection, intrarectal administration, hypodermic injection, intravenous injection, intramuscular injection, or intrathoracic injection.

The recombinant retrovirus of the present invention is preferably administered at an effective dose which can be determined by considering types of disease, severity of disease, drug activity, drug sensitivity, administration period, administration pathway, discharge rate, treatment period, and other drugs co-treated, etc. The composition of the present invention can be administered alone or together with other drugs. If co-treatment is needed, the administration could be performed stepwise or simultaneously.

However, to obtain a preferred effect, the concentration of the active ingredient in the composition of the present invention is 0.001~10,000 mg/kg, and more preferably 0.1~5 g/kg. The composition can be administered once a day or a few times a day.

In one embodiment of the present invention, the inventors separated MuLV-Gag gene and MuLV-Pol gene, and GalV-EnV gene in order to express them respectively in each vector, and cloned P2 promoter and cytosine deaminase gene in the vector containing Gag and Pol genes. The inventors also cloned P2 promoter and thymidine kinase gene in the vector containing Env gene, leading to the construction of the replicating retrovirus vector (see FIG. 31). The present inventors also confirmed that the said vector had excellent drug sensitivity against ganciclovir and 5-fluorocytosine (see FIGS. 37a, 37b, and 37c).

In addition, the present invention provides a use of the retrovirus above for the production of a drug for the prevention or treatment of cancer.

The cancer can have the characteristics mentioned above. The recombinant retrovirus above can be produced from the first recombinant expression vector comprising MuLV Gag-Pol gene, promoter, and cytosine deaminase gene; and the second recombinant expression vector comprising virus Env gene, promoter, and thymidine kinase gene. At this time, the first and the second recombinant expression vectors can be included in the recombinant retrovirus independently or together.

In another embodiment of the present invention, the inventors separated MuLV-Gag gene and MuLV-Pol gene, and GalV-EnV gene in order to express them respectively in each vector, and cloned P2 promoter and cytosine deaminase gene in the vector containing Gag and Pol genes. The inventors also cloned P2 promoter and thymidine kinase gene in the vector containing Env gene, leading to the construction of the replicating retrovirus vector (see FIG. 31). The present inventors also confirmed that the said vector had excellent drug sensitivity against ganciclovir and 5-fluorocytosine (see FIGS. 37a, 37b, and 37c).

EXAMPLES

However, it will be appreciated that those skilled in the art, on consideration of this disclosure, may make modifications and improvements within the spirit and scope of the present invention.

<Example 1> Construction of Replicating Retrovirus Vector System Containing Herpes Simplex Virus Thymidine Kinase Gene Alone <1-1> Virus Vector Construction In the conventional RRV vector, gag, pol, and MuLV-env genes are synthesized as one genome. Herein, the inventors induced the expression of gag-pol and MuLV-env separately in independent vectors. The env gene has been replaced with the GaLV (Gibbon ape Leukemia virus) env gene which has affinity to primates infection. The HSV-TK gene was cloned in gag-pol vector or GaLV-env vector. A fluorescent gene was cross-cloned in each vector as a target marker, leading to the construction of the vector system.

Overall, the virus vector was constructed in the same method ing 1. spRRVe-P1-TK vector: spRRVe-P1-mcs vector having a multi-cloning site under promoter 1 (P1; MCMV immediate-early promoter) was digested with the restriction enzyme PmeI and then treated with CIAP (alkaline phosphatase, Calf intestinal). pSXLC-TK vector (Sugimoto et al., 1994, Bio/Technology 12, 694-698) was digested with the restriction enzymes NcoI and XhoI, and then TK gene was collected. The collected TK gene was treated with T4 DNA polymerase to make blunt end. spRRVe-P1-mcs vector was digested with the restriction enzymes BamHI and SalI, and then treated with CIAP. After collecting, cloning was performed. As a result, spRRVe-P1-TK vector was constructed (FIG. 1a).

2. sRRVgp-P1-RFP vector: sRRVgp vector (Korean Patent Publication No. 10-1381064) containing EcoRI cleavage site in between pol and 3'-LTR was digested with the restriction enzyme EcoRI, which was treated with CIAP. Lenti-P1-REP (monomer) vector (Chungnam National University, Korea) constructed by the present inventors was digested with the restriction enzymes PpuMI and NcoI and then P1-REP gene was collected. The collected P1-RFP gene was cloned in sRRVgp vector by using T4 DNA polymerase, leading to the construction of the vector (FIG. 1a).

3. sRRVgp-P1-TK vector: sRRVgp vector was digested with EcoRI and then treated with CIAP. A PCR product containing EcoRI, PmeI, and P1 promoter (EcoRI-P1-PmeI-EcoRI) was cloned in the vector sRRVgp, leading to the construction of sRRVgp-P1 vector. The vector was digested with the restriction enzyme PmeI, which was then treated with CIAP. TK gene was amplified so as to contain EcoRI cleavage site by using spRRVe-P1-TK vector (Chungnam National University, Korea) constructed by the present inventors as a template with the primer HSV-TK-EcoRI-F (5'-CGGAATTCATGGCTTCGTACCCCGGCCA-3', SEQ. ID. NO: 1) and the primer HSV-TK-EcoRI-R (5'-GCGAATTCTCAGTAGCCTCCCCCATCTC-3', SEQ. ID. NO: 2). The amplified gene was collected and digested with EcoRI, followed by cloning in sRRVgp-P1 vector (FIG. 1b).

4. spRRVe-P1-GFP vector: In order to clone GaLV-env gene in between gag gene and GFP gene of the retrovirus vector Retro-MCMV-GFP (MFG-mCMV-GFP, Korean Patent Publication No. 10-1381064) expressing GFP, Retro-P1-GFP vector (Chungnam National University, Korea) constructed by the present inventors was digested with the restriction enzyme PmeI. GaLV-env gene was amplified so as to contain PmlI cleavage site by using MYK-GaLV vector (Chungnam National University, Korea) constructed by the present inventors as a template with the primer GaLV-PmlI-F (5'-CGGCACGTGATGGTATTGCTGCCTGGG-3', SEQ. ID. NO: 3) and the primer GaLV-PmlI-R (5'-GCCCACGTGTTAAAGGTTACCTTCGTT-3', SEQ. ID. NO: 4). The amplified gene was collected and digested with PmlI, followed by cloning in Retro-P1-GFP vector (FIG. 1b).

<1-2> Virus Production

To produce virus with the vector constructed in Example <1-1>, spRRVe-P1-TK vector and sRRVgp-P1-RFP vector were combined together (spRRVe-P1-TK/sRRVgp-P1-RFP) and sRRVgp-P1-TK vector and spRRVe-P1-GFP vector were combined (sRRVgp-P1-TK/spRRVe-P1-GFP) together.

Overall, one day before the transfection, 293T cells were plated in a 6-well plate at the density of $6 \times 10^5$ cells/well. On the next day, the medium was replaced with FBS and antibiotics free 0.8 ml DMEM. The plate was placed in a cell culture incubator. In the meantime, DMEM was loaded in two 1.5 ml tubes (100 μl/tube) in order to prepare the solution for transfection. One tube contained 1 μg of RRV (spRRVe-P1-TK/sRRVgp-P1-RFP or sRRVgp-P1-TK/spRRVe-P1-GFP) DNA and 5 μl of PLUS reagent (Invitrogen), and the other tube contained 3 μl of lipofectamine (Invitrogen). The tubes stood at room temperature for 15 minutes after well mixing for 10 seconds. The solution containing lipofectamine was poured into the tube containing PLUS reagent, and mixed well for 10 seconds. The tube stood at room temperature for 20 minutes. The mixed solution comprising RRV DNA, PLUS reagent, and lipofectamine was loaded in the cell culture plate 208 μl/well slowly drop by drop, followed by culture for 4 hours. 4 hours later, the medium was discarded and DMEM supplemented with 3% FBS was loaded therein carefully not to make the cells fall off, followed by culture for 48 hours. 48 hours later, supernatant was obtained and filtered with 0.45 μm syringe filter. 30 ml of the filtrate was purified by using 15 ml centricon that can purify 100 kDa protein. To increase the purity, the obtained solution was filtered twice with 15 ml D-PBS, followed by 10-fold concentration. The solution was divided by 50 μl and stored in −80° C. deep freezer.

<1-3> Titration of the Produced Virus

Titer of the virus produced in Example <1-2> was measured by flow cytometry and qPCR.

Overall, one day before the virus infection, glioma cells (U87MG) were inoculated in a 6-well plate. On the next day, the virus 10-fold concentrated and separated was serially diluted in fresh medium (1×, 10×, 50×, 100×, and 500λ) but mostly by 10×. 1 ml of the diluted virus was added with 4 μg/10 of polybrene. The cell number was counted. Then, glioma cells were infected with the virus. 48 hours later, 50 uM of azidothymidine, the virus reverse transcription inhibitor, was added thereto, followed by reaction for 24 hours to inhibit the proliferation of the virus. GFP expression was quantified by flow cytometry and the titer was calculated by the following mathematical formula 1.

$$\text{TU/ml} = (\text{cell number before infection} \times \text{GFP ratio (\%)}) / \text{dilution ratio} \qquad \text{[Mathematical Formula 1]}$$

However, the real-time PCR was performed by using a retrovirus titration set (Cat. #6166, Takara, Japan) according to the manufacturer's instruction to calculate the titer of the produced virus.

As a result, as shown in Table 1, FIG. 2a, and FIG. 2b, the number of glioma cells before the virus infection was 1.533×10⁵, and the virus titer against the glioma cells was approximately 6.13×10⁷ TU/ml (Table 1, FIGS. 2a and 2b).

TABLE 1

Virus titer to glioma cells

GFP ratio (%) in the glioma cells infected with spRRVe-P1-TK/sRRVgp-P1-RFP

|  | 10X dilution | 50X dilution | 100X dilution | 500X dilution |
|---|---|---|---|---|
| 1 time | 16.7 | 8.3 | 4.7 | 1.2 |
| 2 times | 17.5 | 8.6 | 4.7 | 0.4 |
| 3 times | 17.9 | 8.2 | 4.3 | 0.8 |
| Average | 17.36 | 8.36 | 4.56 | 0.8 |
| TU/ml | $2.66 \times 10^7$ | $6.41 \times 10^7$ | $7.00 \times 10^7$ | $6.13 \times 10^7$ |

<1-4> Investigation of Recombination in the Replicating Retrovirus Vector

There is a high chance of recombination in the replicating retrovirus vector designed for gene therapy because the size of genomic RNA is increased due to the inserted foreign gene and the non-homologous nucleotide sequence added thereto. Therefore, in order to construct a stable and efficient replicating retrovirus vector for gene therapy, it is important to trace the chance of recombination in the course of construction and if any it is important to measure the level of recombination. To investigate the stability of the vector constructed in Example <1-1>, the following experiment was performed.

Overall, the glioma cells sub-cultured on the previous day were infected with 10⁶ TU spRRVe-P1-TK/sRRVgp-P1-RFP or 10⁶ TU sRRVgp-P1-TK/spRRVe-P1-GFP for three days. The supernatant was used to infect the U-87MG cells newly sub-cultured on the previous day 8 times stepwise at 3 days intervals. The resultant infected cells were named p1 (passage 1)~p8 (passage 8). RFP or GFP expressed in each phase cells was observed under fluorescent microscope.

Therefore, PCR was performed with the genomic DNA extracted from the same phase cells using the Env vector and gag-pol vector specific primers, MuLV4194F (5'-AG-CAAGCTATTGGCCACTG-3', SEQ. ID. NO: 5), GaLV (1624)F(5'-GACTCAGTCAGCAAGTTAGAG-3', SEQ. ID. NO: 6), and MFGSaclR (5'-CAATCGGAGGACTG-GCGCCCCGAGTGA-3', SEQ. ID. NO: 7), followed by confirmation of the gene amplification as expected. To the PCR reaction tube were loaded 100 ng of genomic DNA, 1× reaction buffer, 0.25 mM dNTP, 0.2 pmol of the forward primer, 0.2 pmol of the reverse primer, and 0.2 unit Taq polymerase and lastly sterilized distilled water was added to make the final volume 20 μl. PCR was performed according to the following conditions as listed in Table 1. The amplified DNA was loaded on 1% agarose gel, followed by analysis.

TABLE 2

PCR condition

| Step | Temp. | Time | Cycle |
|---|---|---|---|
| Denaturation | 94° C. | 3 min. | 1 |
| Polymerization | 94° C. | 30 sec. | 28 |
|  | 60° C. | 30 sec. |  |
|  | 72° C. | 2 min. 30 sec. |  |
| Extension | 72° C. | 7 min. | 1 |

As a result, as shown in FIG. 3a and FIG. 3b, the band strength of the TK gene expressed in spRRVe-P1-TK vector was weakened from p2 phase and the size thereof was decreased rapidly from p3 phase. On the other hand, the RFP gene expressed in sRRVgp-P1-RFP vector was continued to be amplified to produce the same sized PCR product up to p8 phase (FIG. 3a). In the meantime, recombination was not observed in sRRVgp-P1-TK vector and spRRVe-P1-GFP vector (FIG. 3b). The above results confirmed that TK gene was stably positioned better in sRRVgp-P1 vector than in spRRVe-P1 vector.

<1-5> Analysis of the Recombination Pattern of spRRVe-P1-TK Vector

After PCR with the genomic DNA of the combined spRRVe-P1-TK/sRRVgp-P1-RFP in Example <1-4>, the PCR product obtained from p4 phase recombinant band (*) of spRRVe-P1-TK vector, which was smaller than expected, was collected and cloned in pGEM-T vector for gene analysis.

As a result, as shown in FIG. 4, the collected PCR product lost approximately 2 kb gene ranging from GaLV env to P1 until to the brink of 3'-LTR or lost approximately 1.8 kb gene ranging from GaLV env to P1 until HSV-TK end, which seemed to be attributed to the recombination between the nucleotide sequence AGAAAAAGGGGGGAAT or ATGGGG (FIG. 4).

<Example 2> Construction of Replicating Retrovirus Vector System Using Cytosine Deaminase Gene Alone <2-1> Virus Vector Construction Since recombination did not occurred when TK gene was located in sRRVgp-P1 vector in Example <1-4>, another suicidal gene CD now being used in the clinical field as a treatment tool was inserted in spRRVe-P1 vector, leading to the construction of another vector system.

Overall, the virus vector was constructed as follows.

1. spRRVe-P1-yCD vector: pcDNA-yCD vector (Korea Cancer Center Hospital, provided by Dr. Lee) was digested with the restriction enzymes XhoI and HindIII. Then, yCD (SEQ. ID. NO: 16) was collected. The vector spRRVe-P1-MCS(Chungnam National University, Korea) constructed by the present inventors was digested with the restriction enzyme PmeI, where the yCD gene was cloned (FIG. 5).

2. sRRVgp-P1-RFP vector: This vector was constructed by the same manner as described in Example <1-1> (FIG. 5).

<2-2> Virus Production

To produce virus with the vector constructed in Example <2-1>, spRRVe-P1-yCD vector and sRRVgp-P1-RFP vector were combined together (spRRVe-P1-yCD/sRRVgp-P1-RFP), which was used to produce virus by the same manner as described in Example <1-2>.

<2-3> Investigation of Recombination in the Replicating Retrovirus Vector

The investigation was performed by the same manner and with the same conditions as described in Example <1-4> except that the infection with spRRVe-P1-yCD/sRRVgp-P1-RFP virus was performed 5 times stepwise at 3 days intervals to investigate the stability of the vector constructed in Example <2-1> and polymerization was induced at 72° C. for 90 seconds.

As a result, as shown in FIG. 6, recombination was observed in spRRV-P1-yCD vector from the beginning of p1, while recombination was not observed in sRRVgp-P1-RFF vector (FIG. 6).

<2-4> Analysis of the Recombination Pattern of spRRVe-P1-yCD Vector

After PCR with the genomic DNA of the combined spRRVe-P1-yCD/sRRVgp-P1-RFP in Example <2-3>, the PCR product obtained from p4 phase recombinant band (*) of spRRVe-P1-yCD vector, which was smaller than expected, was collected and cloned in pGEM-T vector. 12 clones were analyzed thereafter.

As a result, as shown in FIG. 7, two different recombination patterns were observed. These two types of recombinations were all induced in between GaLV Env and P1 and between yCD and 3'-LTR, suggesting that gene loss was induced therein (FIG. 7).

<Example 3> Construction of Replicating Retrovirus Vector System Containing Both Cytosine Deaminase Gene and Thymidine Kinase Gene <3-1> Virus Production Virus was produced with the combined vector spRRVe-P1-yCD/sRRVgp-P1-TK by the same manner as described in Example <1-2> (FIG. 8).

<3-2> Investigation of Recombination in the Replicating Retrovirus Vector

The investigation was performed by the same manner under the same conditions as described in Example <1-4> except that the infection with spRRVe-P1-yCD/sRRVgp-P1-TK was performed 5 times stepwise at 3 days intervals to investigate the stability of the vector used in Example <3-1>.

As a result, as shown in FIG. 9, it was confirmed that recombination was observed in spRRVe-P1-yCD vector from phase p1 (FIG. 9).

<3-3> Analysis of the Recombination Pattern of spRRVe-P1-yCD Vector

After PCR with the genomic DNA of the combined spRRVe-P1-yCD/sRRVgp-P1-TK in Example <3-2>, the PCR product obtained from p4 phase recombinant band (*) of spRRVe-P1-yCD vector, which was smaller than expected, was collected and cloned in pGEM-T vector. Then, 10 clones proceeded to gene analysis.

As a result, as shown in FIG. 10, 3 different recombination patterns were observed. Two of those patterns were observed between a region from GaLV Env to P1, and a region from yCD to 3'-LTR, and the other recombination was observed between a region from GaLV Env to P1, and yCD gene, where gene loss was confirmed (FIG. 10).

<3-4> Analysis of the Recombination Pattern of sRRVgp-P1-TK Vector

After PCR with the genomic DNA of the combined spRRVe-P1-yCD/sRRVgp-P1-TK in Example <3-2>, the PCR product obtained from p1 phase recombinant band (*) of sRRVgp-P1-TK vector, which was smaller than expected, was recovered and cloned in pGEM-T vector. Then, 20 clones proceeded to gene analysis.

As a result, as shown in FIG. 11, five different recombination patterns were observed, which were mostly observed between the end region of Pol gene and HSV-TK gene or between HSV-TK gene and 3'-LTR, where gene loss was confirmed (FIG. 11).

<3-5> Investigation of Drug Sensitivity of spRRVe-P1-yCD/sRRVgp-P1-TK Virus

The drug sensitivity against ganciclovir (GCV) and 5-fluorocytosine (5-FC) of the virus spRRVe-P1-yCD/sRRVgp-P1-TK produced in Example <3-1> was investigated.

Overall, 293T cells were co-transfected with spRRVe-P1-yCD/sRRVgp-P1-TK by using PLUS reagent (Invitrogen) and lipofectamine (Invitrogen). 2 days later, the supernatant was obtained. The U-87MG cells sub-cultured on the previous day in a 6-well plate at the density of $1.5 \times 10^3$ cells/well were added with 8 μl/ml of polybrene, followed by infection with the virus for 8 hours. 5 days after the infection (post-infection 5 d), the supernatant was obtained. The U-87MG cells sub-cultured on the previous day in a 6-well plate at the density of $1.5 \times 10^3$ cells/well were infected with the supernatant (p1). The infection was continued serially until p4 phase. The cells of each phase were treated with trypsin-EDTA to prepare single cells. The prepared single cells were distributed in a 12-well plate at the density of $1.5 \times 10^3$ cells/well. From the next day of the sub-culture, the cells were treated with 30 μl/ml of GCV and 1 mM 5-FC for 5 days or 8 days, followed by investigation of cell death.

As a result, as shown in FIG. 12, the drug sensitivity against GCV of spRRV-P1-yCD/sRRVgp-P1-TK was continued until p3 phase. In the meantime, the drug sensitivity against 5-FC was not observed even in the post-infection 5 d phase where recombination was not induced (FIG. 12).

<Example 4> Construction of spRRVe-P1-CDa, spRRVe-P1-CDb, and spRRVe-P1-CDc Virus Vector Systems <4-1> Virus Vector Construction Recombination in spRRVe-P1-yCD vector mainly occurred in between GaLV Env gene and P1 promoter and in between 3'-LTR and yCD gene, according to the investigation performed in Example <3-3>. So, the vector system was constructed by eliminating unnecessary nucleotide sequence for virus synthesis.

Overall, the virus vector was constructed with same method.

1. spRRVe-P1-CDa vector: Overlap PCR was performed to construct the vector using spRRVe-P1-yCD vector as a template with the primers spRRVe-CDa-F (5'-GAAGG-TAACCTTTAATTCAATAACAGGAAAG-3', SEQ. ID. NO: 8) and spRRVe-CDa-R (5'-CTTTCCTGTTATTGAAT-TAAAGGTTACCTTC-3', SEQ. ID. NO: 9) (FIG. 13).

2. spRRVe-P1-CDb vector: Overlap PCR was performed to construct the vector using spRRVe-P1-CD vector as a template with the primers spRRVe-CDb-F (5'-GAAGATAT-TGGTGAGTAGCTATAAAATAAAAGATTTT-3', SEQ. ID. NO: 10) and spRRVe-CDb-R (5'-AAAATCTTTTATTT-TATAGCTACTCACCAATATCTTC-3', SEQ. ID. NO: 11) (FIG. 13).

3. spRRVe-P1-CDc vector: Overlap PCR was performed to construct the vector using spRRVe-P1-CD vector as a template with the primers spRRVe-CDc-F (5'-ACCACCG-TAGAACGCAATGGTGACAGGGGGAAT-3', SEQ. ID. NO: 12) and spRRVe-CDc-R (5'-ATTCCCCCTGTCAC-CATTGCGTTCTACGGTGGT-3', SEQ. ID. NO: 13)(FIG. 13).

<4-2> Virus Production

Virus was produced with the combined vectors spRRVe-P1-CDa, spRRVe-P1-CDb or spRRVe-P1-CDc vector, and sRRVgp-P1-RFP vector; and spRRVe-P1-CDa, spRRVe-P1-CDb or spRRVe-P1-CDc vector, and sRRVgp-P1-TK vector constructed in Example <4-1> by the same manner as described in Example <1-2>.

<4-3> Investigation of Recombination in the Vectors spRRVe-P1-CDa, spRRVe-P1-CDb, and spRRVe-P1-CDc The recombination in the vector was investigated by the same manner as described in Example <2-3> except that 6 kinds of viruses produced in Example <4-2> were used to infect the cells in order to investigate the stability of the vector constructed in Example <4-1>.

As a result, as shown in FIG. 14, recombination was observed in the vectors spRRVe-P1-CDa and spRRVe-P1-CDc from the phase p2, while recombination started from the phase p2 in spRRVe-P1-CDb vector so that PCR product was not observed in p3 (FIG. 14).

<4-4> Analysis of the Recombination Pattern of spRRVe-P1-CDa Vector

After PCR with the genomic DNA of the combined vectors spRRVe-P1-CDa/sRRVgp-P1-RFP and spRRVe-P1-CDa/sRRVgp-P1-TK in Example <4-3>, the PCR product obtained from phase p2 and p3 recombinant bands (*) of spRRVe-P1-CDa vector, which was smaller than expected, was collected and cloned in pGEM-T vector. Then, 24 clones proceeded to gene analysis.

As a result, as shown in FIG. 15, recombination was still observed in P1 and in yCD gene or in between yCD gene and 3'-LTR (FIG. 15).

<Example 5> Identification of CD Gene Optimized by Human Codon

The yCD gene used in Example 2~Example 4 demonstrated recombination therein in the course of infection and also showed a low drug sensitivity against 5-FC. To overcome these disadvantages, 8 kinds of CD genes (CD2~CD9) optimized by human codon were identified.

Overall, CD2 was developed from CD by codon optimization at Tocagen, which was used as the positive control. CD3 was the gene produced by optimizing 12 codons that were not optimized by human codon in CD2 gene. CD4 was the gene where 32 sites showing recombination of spRRVe-P1-yCD, spRRVe-P1-CDa, spRRVe-P1-CDb, and spRRVe-P1-CDc vector were all mutated. Therefore, 5 kinds of CD genes, CD5~CD9, were the genes in which yeast CD was optimized by human codon. The 8 kinds of CD genes above were synthesized by Cosmogen Co., Ltd. The sequences of the CD2~CD9 genes are as shown in table 3.

TABLE 3

Sequences of CD genes optimized by human codon

| Sequences of genes optimized by human codon | | Homology to yCD nucleotide sequence (%) | Homology to yCD protein sequence (%) |
|---|---|---|---|
| CD2 (SEQ. ID. NO: 17) | ATGGTGACCGGCGGCATGGCCTCCAAGTGGGAT CAAAAGGGCATGGATATCGCTTACGAGGAGGCC CTGCTGGGCTACAAGGAGGGCGGCGTGCCTATC GGCGGCTGTCTGATCAACAACAAGGACGGCAGT GTGCTGGGCAGGGGCCACAACATGAGGTTCCAG AAGGGCTCCGCCACCCTGCACGGCGAGATCTCC ACCCTGGAGAACTGTGGCAGGCTGGAGGGCAAG GTGTACAAGGACACCACCCTGTACACCACCCTG TCCCCTTGTGACATGTGTACCGGCGCTATCATC ATGTACGGCATCCCTAGGTGTGTGATCGGCGAG AACGTGAACTTCAAGTCCAAGGGCGAGAAGTAC CTGCAAACCAGGGGCCACGAGGTGGTGGTTGTT GACGATGAGAGGTGTAAGAAGCTGATGAAGCAG TTCATCGACGAGAGGCCTCAGGACTGGTTCGAG GATATCGGCGAGTAA | 79 | 98 |
| CD3 (SEQ. ID. NO: 18) | ATGGTGACCGGCGGCATGGCCTCCAAGTGGGAC CAAAAGGGCATGGATATCGCTTACGAGGAGGCC CTGCTGGGCTACAAGGAGGGCGGCGTGCCCATC GGCGGCTGCCTGATCAACAACAAGGACGGCAGC GTGCTGGGCAGGGGCCACAACATGAGGTTCCAG AAGGGCTCCGCCACCCTGCACGGCGAGATCTCC ACCCTGGAGAACTGCGGCAGGCTGGAGGGCAAG GTGTACAAGGACACCACCCTGTACACCACCCTG TCCCCTTGTGACATGTGCACCGGCGCTATCATC ATGTACGGCATCCCTAGGTGCGTGATCGGCGAG AACGTGAACTTCAAGTCCAAGGGCGAGAAGTAC CTGCAGACCAGGGGCCACGAGGTGGTGGTGGTG GACGACGAGAGGTGCAAGAAGCTGATGAAGCAG TTCATCGACGAGAGGCCCCAGGACTGGTTCGAG GACATCGGCGAGTAA | 76 | 98 |
| CD4 (SEQ. ID. NO: 19) | ATGGTGACAGGGGGAATGGCAAGCAAGTGGGAT CAGAAGGGTATGGACATTGCCTATGAGGAGCG GCCTTAGGTTACAAAGAGGGTGGTGTTCCTATT GGCGGATGTCTTATCAATAACAAAGACGGAAGT GTTCTCGGTCGTGGTCACAACATGAGATTTCAA AAGGGATCCGCCACACTACATGGTGAGATCTCC ACTTTGGAGAACTGCGGCAGGCTGGAAGGCAAG GTGTACAAAGATACCACTCTGTACACCACCCTG TCTCCATGCGACATGTGTACAGGTGCCATCATC ATGTATGGTATTCCACGCTGTGTTGTCGGTGAG AACGTTAATTTCAAAAGTAAGGGCGAGAAATAC TTGCAAACCAGGGGCCACGAGGTGGTGGTTGTT GACGATGAGAGGTGTAAAAAGATCATGAAACAA TTTATCGATGAAAGACCTCAGGACTGGTTCGAG GACATCGGCGAGTAA | 95 | 100 |
| CD5 (SEQ. ID. NO: 20) | ATGGTGACTGGCGGCATGGCATCCAAGTGGGAC CAGAAGGGGATGGACATAGCATATGAAGAGGCC GCGTTGGGATATAAGGAGGGCGGTGTACCAATC GGGGGCTGCCTCATTAACAATAAAGATGGCTCC GTTCTGGGTCGCGGCCACAACATGAGGTTTCAG AAGGGCAGTGCGACGCTCCACGGAGAAATCAGC ACACTGGAAATTGTGGGCGATTGGAGGGGAAA GTGTATAAGGATACAACTCTCTACACCACTCTC AGCCCCTGCGATATGTGCACAGGCGCAATCATA ATGTACGGCCATTCCCCGATGCGTGGTGGGGAG AACGTGAACTTCAAGAGCAAAGGAGAGAAATAT CTTCAGACCAGAGGACACGAAGTAGTGGTGGTG GATGATGAACGCTGCAAGAAAATCATGAAACAG TTTATAGATGAACGACCACAAGACTGGTTCGAG GATATCGGCGAATAG | 77 | 100 |
| CD6 (SEQ. ID. NO: 21) | ATGGTTACTGGAGGGATGGCCAGTAAATGGGAC CAGAAGGGTATGGATATTGCATACGAGGAGGCC GCTTTGGGATACAAGGAGGGGGGTGTCCCTATA GGCGGTTGCCTGATCAATAATAAAGACGGCTCT GTCTTGGGAAGAGGACACAATATGCGCTTTCAG AAGGGAAGCGCCACCCTGCATGGAGAGATCTCT ACCCTCGAAATTGCGGAAGGCTCGAAGGCAAA GTTTACAAAGATACCACCCTCTACACAACGCTG TCCCCCTGTGATATGTGCACCGGTGCCATTATC ATGTATGGCATCCCACGCTGCGTTGTAGGAGAG AATGTAAACTTCAAATCCAAGGGAGAGAAGTAT CTCCAGACCCGAGGGCACGAAGTTGTGGTGGTG GACGATGAAGGTGTAAGAAGATCATGAAGCAG TTCATAGATGAGCGCCTCAGGACTGGTTCGAG GATATTGGCGAATGA | 77 | 100 |

TABLE 3-continued

Sequences of CD genes optimized by human codon

| | Sequences of genes optimized by human codon | Homology to yCD nucleotide sequence (%) | Homology to yCD protein sequence (%) |
|---|---|---|---|
| CD7 (SEQ. ID. NO: 22) | ATGGTAACTGGTGGCATGGCCTCAAAGTGGGAT CAGAAAGGAATGGACATCGCTTACGAGGAGGCC GCACTGGGCTATAAGGAGGGCGGCGTCCCTATA GGCGGTTGCCTGATTAACAATAAAGACGGCTCA GTGCTGGGAAGGGGGCACAACATGAGATTTCAG AAAGGCAGCGCAACTCTGCACGGCGAAATCTCC ACTCTGGAGAACTGCGGGCGGCTGGAGGGAAAG GTTTATAAAGATACTACCTTGTATACAACTCTG TCCCCCTGCGATATGTGCACCGGCGCCATCATA ATGTACGGAATACCCAGGTGCGTGGTGGGAGAG AACGTGAATTTTAAGTCAAAAGGTGAGAAGTAC CTGCAGACTCGCGGCCATGAGGTGGTTGTTGTT GACGATGAAGGTGCAAGAAGATTATGAAGCAG TTCATTGATGAAAGACCCCAGGACTGGTTTGAG GATATCGGAGAGTAG | 79 | 100 |
| CD8 (SEQ. ID. NO: 23) | ATGGTTACTGGGGGAATGGCATCTAAGTGGGAT CAGAAAGGTATGGACATCGCTTATGAAGAGGCT GCTCTCGGCTACAAAGAGGGTGGAGTGCCTATC GGAGGGTGCCTGATCAACAACAAGGACGGCAGT GTGCTGGGGAGGGGCCACAATATGAGGTTCCAA AAAGGCTCCGCCACTCTCCACGGGGAAATTAGT ACCCTCGAGAATTGCGGCGACGATTGGAAGGAAG GTGTACAAGGATACAACACTGTACACCACCCTG TCACCCTGTGATATGTGCACAGGCGCCATTATC ATGTACGGAATCCCTAGATGTGTCGTGGGGGAG AATGTAAACTTCAAAAGTAAGGGGGAGAAATAT CTCCAGACCCGGGGGCACGAAGTCGTCGTTGTG GACGATGAACGGTGTAAGAAGATCATGAAGCAG TTTATCGATGAGAGGCCCCAGGACTGGTTCGAA GACATCGGGGAATAA | 79 | 100 |
| CD9 (SEQ. ID. NO: 24) | ATGGTTACAGGGGGAATGGCAAGTAAATGGGAT CAAAAAGGGATGGATATAGCCTATGAGGAAGCG GCGCTGGGCTATAAAGAGGGAGGGGTGCCGATA GGTGGCTGTCTTATTAATAACAAAGACGGGAGT GTGTTGGGCAGAGGCCACAATATGCGATTTCAA AAAGGGTCCGCGACATTGCACGGAGAGATCAGC ACCCTGGAGAATTGCGGAAGGTTGGAGGGAAAA GTGTATAAGGACACCACCCTCTATACCACACTG TCTCCATGTGATATGTGTACCGGTGCCATCATA ATGTACGGGATTCCTCGCTGCGTAGTGGGAGAG AATGTTAACTTTAAAAGCAAGGGAGAGAAGTAT TTGCAAACCCGGGGCCACGAAGTGGTGGTGGTG GACGACGAGCGATGTAAGAAAATCATGAAGCAA TTTATCGATGAGCGGCCTCAAGATTGGTTCGAA GATATCGGCGAGTGA | 78 | 100 |

<Example 6> Construction of spRRVe-P1-CDs Virus V drug sensitivity against 5-FC in Example <6-3> were recovered (collected). The PCR products were cloned in pGEM-T vector. Then, 24 clones proceed to gene analysis.

As a result, as shown in FIGS. 19a~20b, various recombination patterns were observed. Mostly, recombination was observed in CD or in between CD and 3'-LTR from P1 (FIGS. 19a~20b).

<Example 7> Construction of spRRVe-P2-CDs Virus Vector System

<7-1> Virus Vector Construction

It was confirmed from <Example 1>~<Example 6> that the recombination in spRRV-P1 vector mainly occurred in P1 promoter region. This seemed because of the repeated nucleotide sequence of P1 promoter. So, P1 was replaced with P2 gene control region, leading to the construction of another vector system.

Overall, p1 promoter (MCMV immediate-early promoter) region was eliminated from each spRRVe-P1-CDs and p2 promoter (EF1α promoter) without repeated nucleotide sequence was cloned therein, leading to the construction of the vectors spRRVe-P2-yCD and spRRVe-P2-CDs. At this time, CD4 gene demonstrating a weak drug sensitivity was excluded (FIG. 21).

<7-2> Virus Production

Virus was produced with the vectors spRRVe-P2-yCD, spRRVe-P2-CD2, spRRVe-P2-CD3, spRRVe-P2-CD5, spRRVe-P2-CD6, spRRVe-P2-CD7, and spRRVe-P2-CD8 or the combined vector spRRVe-P2-CD9 and sRRVgp-P1-TK constructed in Example <7-1> by the same manner as described in Example <1-2>.

<7-3> Investigation of Drug Sensitivity of spRRVe-P2-yCD/sRRVgp-P1-TK and spRRVe-P2-CDs/sRRVgp-P1-TK The drug sensitivity of the virus produced in Example <7-2> against GCV and 5-FC was investigated by the same manner as described in Example <3-5> except that the virus produced in Example <7-2> was co-transfected to infect stepwise from p1 to p9 and cell death was observed after treating GCV and 5-FC for 9 or 12 days, respectively.

As a result, as shown in FIGS. 22a~22f, cell death was observed in spRRVe-P2-CDs/sRRVgp-P1-TK until phage p8, unlike spRRVe-P1-CDs/sRRVgp-P1-TK. However, from p9, cell killing activity was rapidly reduced. In the meantime, cell killing activity of spRRVe-P2-CD6, spRRVe-P2-CD7, and spRRVe-P2-CD8 was always weaker than that of spRRVe-P2-CD2, the positive control. However, drug sensitivity against 5-FC was much improved, compared with that of spRRVe-P2-yCD (FIGS. 22a~22f).

<7-4> Investigation of Recombination in spRRVe-P2-yCD/sRRVgp-P1-TK and spRRVe-P2-CDs/sRRVgp-P1-TK The stability of the vector constructed in Example <7-1> was investigated by the same manner and under the same conditions as described in Example <6-4> except that 8 kinds of viruses produced in Example <7-2> were used for the infection.

As a result, as shown in FIG. 23, recombination was not observed in spRRVe-P2-CDs vectors except spRRVe-P2-CD5 until phase p4, while recombination was mainly observed in sRRVgp-P1-TK vector from phase p1 or p2 (FIG. 23).

<7-5> Analysis of the Recombination Pattern of sRRVgp-P1-TK

After PCR with the genomic DNA of the combined vectors spRRVe-P2-yCD/sRRVgp-P1-TK and spRRVe-P2-CDs/sRRVgp-P1-TK in Example <7-4>, the PCR product obtained from phase p3 and p4 recombinant bands of sRRVgp-P1-TK vector, which was smaller than expected, was recovered, followed by gene analysis.

As a result, as shown in FIG. 24, recombination characterized by gene loss was observed in between P1 and TK (FIG. 24).

<Example 8> Construction of sRRVgp-P2-TK Virus Vector System

<8-1> Virus Vector Construction

As a result of Example 7, frequency of recombination in spRRVe-P2-CDs was lower than in the vector using P1 control region. However, gene loss was still observed in P1 control region in sRRVgp-P1-TK vector. The present inventors constructed sRRVgp-P2-TK vector system by replacing P1 promoter region with P2 promoter region.

Overall, PCR was performed to attach EcoRI, NotI, and PmeI restriction enzyme sequences to P2 promoter (EcoRI-P2-NotI-PmeI-EcoRI). The PCR product was digested with EcoRI, and inserted under Pol gene of sRRVgp vector (Chungnam National University, Korea) constructed by the present inventors, leading to the construction of sRRVgp-P2 vector. HSV-TK gene was amplified by PCR so as to contain NotI and PmeI restriction enzyme sequences (NotI-HSV TK-PmeI). Then, the PCR product was digested with NotI and PmeI, followed by cloning in under P2 gene. As a result, the vector sRRVgp-P2-TK was constructed (FIG. 25).

<8-2> Virus Production

Virus was produced with the vector spRRVe-P2-CD2, the recombination free vectors spRRVe-P2-CD6 and spRRVe-P2-CD7 or the combined vector spRRVe-P2-CD8 and sRRVgp-P2-TK by the same manner as described in Example <1-2>.

<8-3> Investigation of Drug Sensitivity of spRRVe-P2-CDs/sRRVgp-P2-TK

The drug sensitivity of the virus produced in Example <8-2> against GCV and 5-FC was investigated by the same manner as described in Example <3-5> except that the virus produced in Example <8-2> was co-transfected to infect stepwise from p1 to p11 and cell death was observed after treating GCV and 5-FC for 5 or 7 days.

As a result, as shown in FIGS. 26a~26c, drug sensitivity of spRRVe-P2-CD6, spRRVe-P2-CD7, and spRRVe-P2-CD8 against 5-FC was as high as that of the positive control spRRVe-P2-CD2 until p11, except spRRVe-P2-yCD (FIGS. 26a~26c).

<8-4> Investigation of Recombination in spRRVe-P2-CDs/sRRVgp-P2-TK

The stability of the vector constructed in Example <8-1> was investigated by the same manner and under the same conditions as described in Example <6-4> except that 4 kinds of viruses produced in Example <8-2> were infected 7 times stepwise at 3 days intervals.

As a result, as shown in FIGS. 27a and 27b, recombination in spRRVe-P2-yCD vector was observed from p4, while recombination in spRRVe-P2-CD2 was observed from p7. In the meantime, recombination in spRRVe-P2-CD6 vector was observed from p6, and recombination in spRRVe-P2-CD7 and spRRVe-P2-CD8 was observed from p5. In particular, recombination in sRRVgp-P2-TK and spRRVe-P2-CD2 was observed particularly early (FIGS. 27a and 27b).

<8-5> Analysis of the Recombination Pattern of spRRVe-P2-CD6 and spRRVe-P2-CD8

PCR products of p7 of spRRVe-P2-CD6 and spRRVe-P2-CD8 confirmed to have recombination in Example <8-4> were collected. The PCR products were cloned in pGEM-T vector. Then, 19 clones proceed to gene analysis.

As a result, as shown in FIGS. 28a~29b, recombination was confirmed in between P2 and to the brink of 3'-LTR (FIGS. 28a~29b).

<Example 9> Additional Identification of 7 Kinds of CD Genes Optimized by Human Codon In the examples above, CD6, CD7, and CD8 genes confirmed to have excellent drug sensitivity, compared to yCD gene, were identified. To secure CD gene that has maximized drug dependent cell killing activity, the present inventors additionally identified 7 other CD genes (CD10~CD16) optimized by human codon.

7 kinds of CD genes, CD10~CD16, were the genes in which yeast CD was optimized by human codon. The 7 kinds of CD genes above were synthesized by Cosmogen Co., Ltd. The sequences of the CD10~CD16 genes are as shown in table 4.

TABLE 4

Sequences of CD genes optimized by human codon

| Sequences of genes optimized by human codon | Homology to yCD nucleotide sequence (%) | Homology to yCD protein sequence (%) |
|---|---|---|
| CD10 (SEQ. ID. NO: 25) ATGGTAACCGGAGGTATGGCATCCAAGTGGGAC CAAAAAGGAATGGACATAGCATATGAAGAAGCA GCCCTGGGCTACAAGGAGGGAGGGGTTCCGATT GGCGGTTGTCTTATAAATAATAAAGACGGTAGT GTTCTTGGCAGGGGTCACAACATGAGATTCCAA AAGGGGAGTGCTACACTTCACGGCGAAATAAGC ACCTTGGAAAACTGTGGTAGACTTGAGGGAAAA GTGTACAAGGACACGACCCTTTATACGACGCTG TCCCCTTGTGATATGTGCACCGGCGCTATCATC ATGTATGGAATACCACGATGCGTAGTGGGAGAG AATGTTAATTTCAAGAGTAAGGGCGAGAAGTAC CTTCAGACCAGGGGCACGAGGTAGTAGTAGTT GACGATGAGCGATGCAAGAAGATTATGAAACAA TTCATTGACGAGAGGCCGCAGGATTGGTTTGAA GACATCGGCGAATAG | 80 | 100 |
| CD11 (SEQ. ID. NO: 26) ATGGTGACAGGGGGTATGGCAAGCAAATGGGAT CAGAAGGGTATGGACATCGCATACGAGGAGGCG GCCTTGGGCTATAAGGAAGGCGGCGTACCTATA GGGGGTGCCTTATTAACAATAAGGACGGGAGC GTCCTGGGCAGAGGTCACAACATGAGGTTCCAA AAGGGTTCAGCAACCCTGCATGGCGAAATAAGC ACCCTTGAGAATTGTGGGAGGTTGGAGGGTAAG GTGTACAAGGATACCACGCTTTATACCACCTTG AGTCCTTGCGACATGTGCACAGGCGCTATAATC ATGTATGGAATACCGCGCTGTTGTTAGGAGAA AATGTAAACTTCAAGATAAAGGAGAAAATAC TTGCAAACGCGGGGACACGAAGTGGTAGTTGTC GATGATGAGCGGTGCAAAAAATCATGAAGCAG TTCATTGACGAACGCCCCCAAGACTGGTTCGAA GACATTGGGGAGTAG | 78 | 100 |
| CD12 (SEQ. ID. NO: 27) ATGGTAACGGGTGGGATGGCTAGCAAGTGGGAC CAGAAAGGCATGGATATAGCGTATGAAGAAGCG GCGTTGGGTTACAAAGAGGGCGGCGTTCCCATC GGTGGCTGCCTTATCAATAATAAAGACGGCTCC GTCCTTGGCCGGGGACACAATATGCGCTTCCAA AAGGGCAGCGCCACACTTCACGGTGAGATCTCC ACGCTGGAGAATTGTGGGCGACTTGAGGGGAAA GTCTACAAGGACACAACTTTGTACACAACACTT AGCCCGTGCGATATGTGTACGGGAGCCATAATC ATGTACGGCATCCCGCGCTGCGTGGTAGGAGAG AACGTAAATTTTAAGTCAAAAGGAGAAAAATAT | 79 | 100 |

TABLE 4-continued

Sequences of CD genes optimized by human codon

| Sequences of genes optimized by human codon | Homology to yCD nucleotide sequence (%) | Homology to yCD protein sequence (%) |
|---|---|---|
| CTTCAGACCAGGGGCCACGAGGTGGTTGTCGTG GACGACGAGAGATGTAAAAAGATCATGAAACAG TTTATTGATGAAAGACCACAGGATTGGTTTGAG GACATCGGTGAGTAG | | |
| CD13 (SEQ. ID. NO: 28) ATGGTTACAGGAGGTATGGCTTCAAAGTGGGAT CAAAAAGGGATGGACATCGCCTATGAAGAAGCA GCGTTGGGATACAAAGAAGGGGGGGTTCCCATA GGAGGTTGCCTTATCAACAATAAAGATGGAAGC GTTCTTGGGCGAGGGCACAATATGAGATTTCAA AAAGGTTCAGCCACTCTCCATGGAGAAATTTCA ACTCTCGAAAACTGTGGTCGCCTTGAGGGCAAG GTTTATAAGGATACCACCCTCTACACTACCCTG TCACCCTGCGACATGTGTACAGGTCAATTATA ATGTACGGAATCCCTCGGTGTGTGGTGGGGGAG AACGTGAATTTAAGTCCAAAGGTGAAAAATAT CTCCAAACTCGCGGGCATGAAGTCGTCGTTGTT GATGATGAGAGGTGTAAAAAGATTATGAAACAA TTCATAGACGAGAGGCCACAGGATTGGTTTGAG GACATAGGGGAGTAG | 78 | 100 |
| CD14 (SEQ. ID. NO: 29) ATGGTGACTGGGGGTATGGCTTCCAAATGGGAT CAGAAAGGAATGGATATAGCATACGAAGAAGCA GCTCTCGGGTACAAAGAGGGTGGAGTACCCATT GGGGGATGCCTCATCAACAACAAGGATGGGAGT GTCCTTGGGCGAGGTCACAATATGCGATTCCAG AAGGGGAGCGCGACGCTCCACGGGGAGATAAGT ACGCTGGAGAACTGCGGGAGGCTTGAAGGCAAG GTCTACAAAGATACCACACTCTACACGACCCTC AGCCCTTGCGACATGTGTACGGGTGCGATCATC ATGTATGGAATACCGCGATGCGTAGTAGGAGAG AACGTGAACTTCAAGTCCAAAAGCGAAAAGTAT CTCCAGACGCGCGGCCACGAAGTGGTAGTGGTA GACGACGAAAGGTGCAAGAAGATAATGAAGCAG TTTATCGACGAGAGGCCTCAGGACTGGTTCGAG GATATTGGCGAGTAG | 76 | 100 |
| CD15 (SEQ. ID. NO: 30) ATGGTTACTGGCGGCATGGCTTCTAAGTGGGAT CAGAAGGGCATGGATATAGCCTATGAAGAAGCA GCACTGGGATACAAAGAGGGAGGGGTACCAATT GGGGGATGTCTGATTAATAACAAAGACGGAAGT GTACTCGGTCGCGGGCATAATATGAGATTCCAA AAAGGCTCTGCAACGTTGCACGGCGAAATCAGC ACGCTCGAAATTGCGGGAGGCTGGAGGGAAAG GTTTACAAGGATACCACTCTCTATACCACACTG TCACCATGTGATATGTGTACGGGGCTATAATA ATGTATGGAATCCCCGCTGCGTCGTGGGCGAA AACGTCAACTTTAAGTCTAAGGGGGAAAAGTAT TTGCAAACGCGCGGTCATGAGGTCGTTGTAGTC GATGACGAGAGATGCAAAAAAATAATGAAGCAG TTTATTGACGAGAGACCTCAGGACTGGTTCGAA GACATCGGGGAGTAG | 77 | 100 |
| CD16 (SEQ. ID. NO: 31) ATGGTGACAGGAGGAATGGCCAGCAAGTGGGAT CAGAAGGGAATGGATATTGCCTACGAGGAGGCC GCCCTGGGCTACAAGGAGGGGGCGTGCCAATT GGCGGATGTCTGATTAACAACAAGGATGGGAGC GTGCTGGGAAGAGGACACAACATGAGATTTCAG AAGGGAAGCGCAACCTTGCAGGAAATTAGC ACCCTTGAGAACTGCGGGCGGCTTGAAGGCAAG GTCTATAAAGACACTACACTTTATACTACCTTG TCTCCATGTGATATGTGTACAGGCGCCATTATT ATGTACGGAATTCCTAGATGCGTCGTGGGAGAG AACGTGAACTTTAAGAGCAAGGGAGAGAAGTAC | 78 | 100 |

TABLE 4-continued

Sequences of CD genes optimized by human codon

| Sequences of genes optimized by human codon | Homology to yCD nucleotide sequence (%) | Homology to yCD protein sequence (%) |
|---|---|---|
| CTGCAGACAAGAGGACACGAGGTGGTGGTGGTG GATGATGAGAGATGTAAGAAGATCATGAAGCAG TTCATCGATGAGAGGCCCCAGGATTGGTTTGAG GACATCGGCGAGTGA | | |

<Example 10> Construction of spRRVe-P2-CDs Virus Vector System

<10-1> Virus Vector Construction

The CD genes optimized by human codon, newly identified in <Example 9>, were cloned in spRRVe-P2 vector, resulting in the construction of the vectors spRRVe-P2-CDs.

<10-2> Virus Production

Virus was produced by the same manner as described in Example <1-2> by using the combination of 7 kinds of spRRVe-P2-CDs constructed in Example <10-1> and sRRVgp-P2-TK vector.

<10-3> Investigation of Drug Sensitivity of spRRVe-P2-CDs/sRRVgp-P2-TK

The drug sensitivity of the virus produced in Example <10-2> against GCV and 5-FC was investigated by the same manner as described in Example <3-5> except that the virus produced in Example <10-2> was co-transfected to infect stepwise from p1 to p5 and cell death was observed after treating GCV and 5-FC for 6 or 8 days, respectively.

As a result, as shown in FIGS. 30*a*~30*c*, it was confirmed that CD6 gene had the most excellent drug sensitivity (FIGS. 30*a*~30*c*).

<Example 11> Construction of spRRVe-P2-TK, sRRVgp-P2-CD2, sRRVgp-P2-CD6, sRRVgp-P2-CD7, and sRRVgp-P2-CD8 Virus Vector System <11-1> Virus Vector Construction As serial infection phases were extended in Example <8-4>, even the vector containing P2 promoter, spRRVe-P2-CDs, displayed recombination action. To improve this problem, the combined vector, spRRVe-P2-TK/sRRVgp-P2-CDs, was prepared to construct a virus vector system.

Overall, the virus vector was constructed with same method.

1. spRRVe-P2-TK vector: PCR was performed using TK gene as a template with the primers HSV-TK-BamHI-F (5'-CGGGATCCATGGCTTCGTACCCCTGCCAT-3', SEQ. ID. NO: 11) and HSV-TK-SalI-R (5'-CGGTCGACTCAGTTAGCCTCCCCCATCTC-3', SEQ. ID. NO: 12). The PCR product was digested with the restriction enzymes BamHI and SalI, and then cloned in BamHI-SalI site of spRRVe-P2-mcs vector, leading to the construction of spRRVe-P2-TK vector (SEQ. ID. NO: 13) (FIGS. 31, 32, and 33*a*~33*r*).

2. sRRVgp-P2-yCD vector: PCR was performed using yCD gene as a template with the primers CD-NotI-F (5'-CGGCGGCCGCATGGTGACAGGGGGAATGGC-3', SEQ. ID. NO: 36) and CD-PmeI-R (5'-CGGTTTAAACCTACTCACCAATATCTTCAAA-3', SEQ. ID. NO: 37). The PCR product was digested with the restriction enzymes NotI and PmeI, and then cloned in NotI-PmeI site of sRRVgp-P2 vector, leading to the construction of sRRVgp-P2-yCD vector.

3. sRRVgp-P2-CD2 vector: PCR was performed using CD2 gene as a template with the primers CD2-NotI-F (5'-CGGCGGCCGCATGGTGACCGGCGGCATGGC-3', SEQ. ID. NO: 38) and CD2-PmeI-R (5'-CGGTTTAAACTTACTCGCCGATATCCTCGA-3', SEQ. ID. NO: 39). The PCR product was digested with the restriction enzymes NotI and PmeI, and then cloned in NotI-PmeI site of sRRVgp-P2 vector, leading to the construction of sRRVgp-P2-CD2 vector.

4. sRRVgp-P2-CD6 vector: PCR was performed using CD6 gene as a template with the primers CD6-NotI-F (5'-CGGCGGCCGCATGGTTACTGGAGGGATGGC-3', SEQ. ID. NO: 40) and CD6-PmeI-R (5'-CGGTTTAAACTCATTCGCCAATATCCTCGA-3', SEQ. ID. NO: 41). The PCR product was digested with the restriction enzymes NotI and PmeI, and then cloned in NotI-PmeI site of sRRVgp-P2 vector, leading to the construction of sRRVgp-P2-CD6 vector (SEQ. ID. NO: 14) (FIGS. 31, 34, and 35*a*~35*o*).

5. sRRVgp-P2-CD7 vector: PCR was performed using CD7 gene as a template with the primers CD7-NotI-F (5'-CGGCGGCCGCATGGTAACTGGTGGCATGGC-3', SEQ. ID. NO: 42) and CD7-PmeI-R (5'-CGGTTTAAACCTACTCTCCGATATCCTCAA-3', SEQ. ID. NO: 43). The PCR product was digested with the restriction enzymes NotI and PmeI, and then cloned in NotI-PmeI site of sRRVgp-P2 vector, leading to the construction of sRRVgp-P2-CD7 vector.

6. sRRVgp-P2-CD8 vector: PCR was performed using CD8 gene as a template with the primers CD8-NotI-F (5'-CGGCGGCCGCATGGTTACTGGGGGAATGG-3', SEQ. ID. NO: 44) and CD8-PmeI-R (5'-CGGTTTAAACTTATTCCCCGATGTCTTCGA-3', SEQ. ID. NO: 45). The PCR product was digested with the restriction enzymes NotI and PmeI, and then cloned in NotI-PmeI site of sRRVgp-P2 vector, leading to the construction of sRRVgp-P2-CD8 vector.

<11-2> Virus Production

Virus was produced by the same manner as described in Example <1-2> by using the combination of the vectors such as sRRVgp-P2-yCD, sRRVgp-P2-CD2, sRRVgp-P2-CD6, sRRVgp-P2-CD7, or sRRVgp-P2-CD8 constructed in Example <11-1> and spRRVe-P2-TK vector.

<11-3> Investigation of Recombination in spRRVe-P2-TK/sRRVgp-P2-CD (2,6,7,8)

The stability of the vectors constructed in Example <11-1> was investigated by the same manner and under the same conditions as described in Example <1-4> except that spRRVe-P2-TK/sRRVgp-P2-CD (2,6,7,8) were infected 7 times stepwise at 3 days intervals and polymerization was induced at 72° C. for 3 minutes.

As a result, as shown in FIGS. 36*a* and 36*b*, recombination was not observed in those vectors sRRVgp-P2-CD6, sRRVgp-P2-CD7, and sRRVgp-P2-CD8, until phase p7 (FIGS. 36*a* and 36*b*).

<11-4> Analysis of the Recombination Pattern of spRRVe-P2-TK/sRRVgp-P2-CDs

After PCR with the genomic DNA of the combined vectors spRRVe-P2-TK/sRRVgp-P2-yCD, spRRVe-P2-TK/ sRRVgp-P2-CD2, spRRVe-P2-TK/sRRVgp-P2-CD6, spRRVe-P2-TK/sRRVgp-P2-CD7, and spRRVe-P2-TK/sRRVgp-P2-CD8 in Example <11-3>, the PCR products obtained from phase p6 and p7 of spRRVe-P2-TK, sRRVgp-P2-yCD, and sRRVgp-P2-CD (2,6,7,8) vectors were recovered, followed by gene analysis.

As a result, as shown in FIGS. 36*a* and 36*b*, recombination was not observed in any of sRRVgp-P2-CD6, sRRVgp-P2-CD7, and sRRVgp-P2-CD8. These vectors had more excellent stability than the positive control vector sRRVgp-P2-CD2 (FIGS. 36*a* and 36*b*).

<11-5> Investigation of Drug Sensitivity of spRRVe-P2-TK/sRRVgp-P2-CDs

The drug sensitivity of the virus produced in Example <11-2> against GCV and 5-FC was investigated by the same manner as described in Example <3-5> except that the virus produced in Example <11-2> was co-transfected to infect stepwise from p1 to p9 and cell death was observed after treating GCV and 5-FC for 8 or 12 days, respetively.

As a result, as shown in FIGS. 37*a*~37*c*, cell death by sRRVgp-P2-CD6, sRRVgp-P2-CD7, sRRVgp-P2-CD8, and spRRVe-P2-TK was well observed until phase p7 (FIGS. 37*a*~37*c*).

The invention claimed is:

1. A replicating retrovirus vector system comprising:
   a first recombinant expression vector containing an MuLV Gag-Pol gene, a promoter, and one of a cytosine deaminase gene or a thymidine kinase gene; and
   a second recombinant expression vector containing a virus Env gene, a promoter, and the other of said thymidine kinase gene or cytosine deaminase gene,
   wherein the thymidine kinase gene or cytosine deaminase gene can activate a prodrug.

2. The replicating retrovirus vector system according to claim 1, wherein the promoter in said first recombinant expression vector or the promoter in said second recombinant expression vector is originated from one of those of cancer specific promoters selected from the group consisting of an MCMV immediate-early promoter, an EF1α promoter, a HCMV immediate-early promoter, a PGK promoter, and a TERT promoter.

3. The replicating retrovirus vector system according to claim 2, wherein the EF1α promoter is a polynucleotide comprising SEQ ID NO: 34.

4. The replicating retrovirus vector system according to claim 1, wherein the virus Env gene is selected from the group consisting of those Env genes of Gibbon ape Leukemia virus (GaLV), amphotropic MuLV, xenotropic MuLV, RD114, vesicular stomatitis virus (VSV), and measles virus (MV).

5. The replicating retrovirus vector system according to claim 4, wherein the GaLV Env gene is a polynucleotide comprising SEQ ID NO: 35.

6. The replicating retrovirus vector system according to claim 1, wherein the thymidine kinase is a polynucleotide comprising SEQ ID NO: 15.

7. The replicating retrovirus vector system according to claim 1, wherein the cytosine deaminase gene is human codon optimized.

8. The replicating retrovirus vector system according to claim 7, wherein the cytosine deaminase gene is a polynucleotide selected from the group consisting of SEQ ID NOs: 16-31.

9. The replicating retrovirus vector system according to claim 1, wherein the MuLV Gag-Pol gene is a polynucleotide having the fused nucleotide sequence comprising SEQ ID NO: 32 and SEQ ID NO: 33.

10. A recombinant retrovirus composition harboring the vector system of claim 1, comprising a retrovirus containing the first recombinant expression vector, and a second retrovirus containing the second recombinant expression vector.

11. A host cell transfected with the recombinant retrovirus composition of claim 10.

12. A method for treating cancer comprising:
   administering the recombinant retrovirus of claim 10 to a subject in need, and administering a prodrug to said subject,
whereby said prodrug is activated by the expressed thymidine kinase or cytosine deaminase.

13. The method of claim 12, wherein the cancer is selected from the group consisting of mucous carcinoma, round cell carcinoma, locally advanced tumor, metastatic cancer, Ewing sarcoma, cancer metastasis, lymphatic metastasis, squamous cell carcinoma, esophageal squamous cell carcinoma, oral carcinoma, multiple myeloma, acute lymphoblastic leukemia, acute nonlymphoid leukemia, chronic lymphocytic leukemia, chronic myeloid leukemia, hairy cell leukemia, effusion lymphoma, thymus lymphoma lung cancer, small cell lung cancer, cutaneous T cell lymphoma, Hodgkin's lymphoma, non-Hodgkin's lymphoma, adrenal cortical carcinoma, ACTH-producing tumor, non-small cell lung cancer, breast cancer, small cell carcinoma, ductal carcinoma, stomach cancer, colon cancer, colorectal cancer, polyp related to colorectal cancer formation, pancreatic cancer, liver cancer, bladder cancer, primary surface bladder tumor, invasive metastatic cell bladder carcinoma, muscle-invasive bladder cancer, prostate cancer, colon cancer, kidney cancer, hepatocarcinoma, esophageal cancer, ovarian carcinoma, uterine cervical cancer, endometrial cancer, choriocarcinoma, ovarian cancer, primary peritoneum neoplasm, uterine cervical carcinoma, vaginal cancer, pudendum cancer, uterine cancer, follicle solid tumor, testis cancer, penis cancer, renal cell carcinoma, brain cancer, head/neck cancer, neuroblastoma, brainstem glioma, glioma, metastatic tumor cell invasion in central nervous system, osteoma, osteosarcoma, malignant melanoma, human skin keratinocyte tumor progression, squamous cell carcinoma, thyroid cancer, retinoblastoma, neuroblastoma, mesothelioma, Wilm's tumor, gallbladder cancer, trophoblastic tumor, hemangiopericytoma, and Kaposi's sarcoma.

14. A method for preparing a replicating retrovirus vector system comprising:
1) preparing a first recombinant expression vector containing a MuLV Gag-Pol gene, a promoter, and a cytosine deaminase gene;
2) preparing a second recombinant expression vector containing a virus Env gene, a promoter, and a thymidine kinase gene; and
3) combining said first recombinant expression vector and said second recombinant expression vector.

15. A method for preparing a replicating retrovirus vector system comprising:
1) preparing a first recombinant retrovirus containing a MuLV Gag-Pol gene, a promoter, and thymidine kinase gene;
2) preparing a second recombinant retrovirus containing an Env gene, a promoter, and a cytosine deaminase gene; and
3) combining said first recombinant retrovirus and said second recombinant retrovirus.

* * * * *